US012715839B2

(12) United States Patent
Churchill

(10) Patent No.: US 12,715,839 B2
(45) Date of Patent: Aug. 25, 2026

(54) BRANCHED-CHAIN AMINO ACID DERIVATIVES TO TREAT DISEASE

(71) Applicant: INTRABIO LTD., London (GB)

(72) Inventor: Grant Charles Churchill, Oxford (GB)

(73) Assignee: INTRABIO LTD., London (GB)

( * ) Notice: Subject to any disclaimer, the term of this patent is extended or adjusted under 35 U.S.C. 154(b) by 325 days.

(21) Appl. No.: 18/539,781

(22) Filed: Dec. 14, 2023

(65) Prior Publication Data

US 2024/0208895 A1 Jun. 27, 2024

Related U.S. Application Data

(63) Continuation-in-part of application No. PCT/IB2022/055513, filed on Jun. 14, 2022.

(60) Provisional application No. 63/210,362, filed on Jun. 14, 2021.

(51) Int. Cl.

| | |
|---|---|
| ***C07C 235/12*** | (2006.01) |
| ***A61K 31/223*** | (2006.01) |
| ***A61P 25/00*** | (2006.01) |
| ***C07C 233/47*** | (2006.01) |
| ***C07C 233/52*** | (2006.01) |

(52) U.S. Cl.

CPC .......... *C07C 235/12* (2013.01); *A61K 31/223* (2013.01); *A61P 25/00* (2018.01); *C07C 233/47* (2013.01); *C07C 233/52* (2013.01); *C07C 2601/02* (2017.05); *C07C 2601/04* (2017.05)

(58) Field of Classification Search

CPC ... C07C 235/12; C07C 233/47; C07C 233/52; C07C 2601/02; C07C 2601/04; A61K 31/223; A61P 25/00

See application file for complete search history.

(56) References Cited

U.S. PATENT DOCUMENTS 8,202,525 B2 6/2012 Crain et al.
9,155,719 B2 10/2015 Rekik
9,283,181 B2 3/2016 Calias et al.
9,296,723 B2 3/2016 Curtin et al.
10,905,670 B2 2/2021 Factor et al.
10,950,670 B2 3/2021 Luo
11,083,718 B2 8/2021 Strupp
11,400,067 B2 8/2022 Strupp
11,471,434 B2 10/2022 Strupp et al.
11,660,279 B2 5/2023 Factor et al.
11,690,830 B2 7/2023 Strupp
11,793,782 B2 10/2023 Factor
11,998,518 B2 6/2024 Factor et al.
12,144,792 B2 11/2024 Strupp
12,145,899 B2 11/2024 Mann
12,329,733 B2 6/2025 Factor et al.
2002/0095135 A1 7/2002 Meeker et al.
2004/0127501 A1 7/2004 Chen et al.
2006/0063827 A1 3/2006 Yu et al.
2006/0128717 A1 6/2006 Sun et al.
2006/0235022 A1 10/2006 Sun
2006/0235055 A1 10/2006 Kyle et al.
2006/0241117 A1 10/2006 Sun
2007/0027159 A1 2/2007 Kyle et al.
2007/0032500 A1 2/2007 Sun et al.
2007/0276041 A1 11/2007 Oonuki et al.
2008/0214649 A1 9/2008 Yu et al.
2009/0318555 A1 12/2009 Fabre et al.
2013/0123239 A1 5/2013 Kurose
2013/0142888 A1 6/2013 Rekik (Continued)

FOREIGN PATENT DOCUMENTS

CN 103079550 A 5/2013
CN 103814046 A 5/2014

(Continued)

OTHER PUBLICATIONS

Angelini, C., et al., "Major intra-familial phenotypic heterogeneity and incomplete penetrance due to a CACNA1A pathogenic variant," Eur J Med Genet 62(6):103530, Elsevier, Netherlands (Aug. 2018).
Ashizawa, T., and Xia, G., "Ataxia," Continuum (Minneap Minn) 22(4) Movement Disorders):1208-1226, Wolters Kluwer, United States (Aug. 2016).
Beaudin, M., et al., "Systematic review of autosomal recessive ataxias and proposal for a classification," Cerebellum Ataxias 4:3, BioMed Central, United Kingdom (Feb. 2017).
Bird, T.D., "Hereditary Ataxia Overview," in *GeneReviews® (Internet)*, Adam, M.P., Ardinger H.H,, Pagon, R.A., et al., eds., pp. 1993-2020, University of Washington, Seattle, United States, Oct. 1998 (Updated Jul. 2019).

(Continued)

*Primary Examiner* — Ali Soroush
(74) *Attorney, Agent, or Firm* — Sterne, Kessler, Goldstein & Fox P.L.L.C.

(57) ABSTRACT

The present disclosure provides compounds represented by Formula I:

I

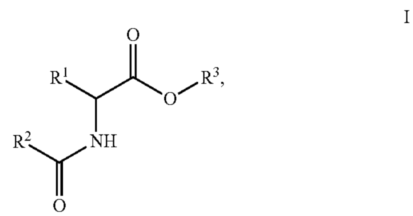

and the pharmaceutically acceptable salts and solvates thereof, wherein $R^1$, $R^2$, and $R^3$ are as defined as set forth in the specification. The present disclosure also provides compounds having Formula I for use to treat or prevent the progression of a lysosomal storage disorder or a neurodegenerative disease in a subject, provide neuroprotection in a subject having a lysosomal storage disorder, treat or prevent a migraine, and the symptoms associated therewith, in a subject, or improve mobility and/or cognitive function in a subject.

8 Claims, 12 Drawing Sheets

(56) References Cited

U.S. PATENT DOCUMENTS

| | | | |
|---|---|---|---|
| 2013/0317036 | A1 | 11/2013 | Rekik |
| 2014/0080885 | A1 | 3/2014 | Pennypacker et al. |
| 2014/0350056 | A1 | 11/2014 | Yu |
| 2019/0046486 | A1 | 2/2019 | De Rienzo et al. |
| 2019/0083438 | A1 | 3/2019 | Factor et al. |
| 2019/0201359 | A1 | 7/2019 | Strupp |
| 2020/0179320 | A1 | 6/2020 | Strupp |
| 2020/0253905 | A1 | 8/2020 | Strupp et al. |
| 2020/0338034 | A1 | 10/2020 | Factor |
| 2021/0106548 | A1 | 4/2021 | Factor et al. |
| 2021/0196659 | A1 | 7/2021 | Factor |
| 2021/0361632 | A1 | 11/2021 | Strupp |
| 2022/0024858 | A1 | 1/2022 | Mann |
| 2022/0142959 | A1 | 5/2022 | Factor et al. |
| 2022/0331278 | A1 | 10/2022 | Strupp |
| 2022/0362189 | A1 | 11/2022 | Factor et al. |
| 2023/0051742 | A1 | 2/2023 | Strupp |
| 2023/0201150 | A1 | 6/2023 | Strupp |
| 2023/0210799 | A1 | 7/2023 | Strupp |
| 2023/0346732 | A1 | 11/2023 | Factor et al. |
| 2024/0189267 | A1 | 6/2024 | Strupp |
| 2024/0197663 | A1 | 6/2024 | Strupp |
| 2025/0129011 | A1 | 4/2025 | Mann |

FOREIGN PATENT DOCUMENTS

| | | | | |
|---|---|---|---|---|
| EP | 0226304 | A1 | | 6/1987 |
| EP | 0288447 | A1 | | 10/1988 |
| FR | 2905600 | A1 | | 3/2008 |
| JP | H08103242 | A | * | 4/1996 |
| JP | 2009269856 | A | | 11/2009 |
| JP | 2014503596 | A | | 2/2014 |
| JP | 2016513084 | A | | 5/2016 |
| RU | 2012151575 | A | | 7/2014 |
| RU | 2680413 | C1 | | 2/2019 |
| WO | WO-9526325 | A2 | | 10/1995 |
| WO | WO-9621464 | A1 | | 7/1996 |
| WO | WO-2005079300 | A2 | | 9/2005 |
| WO | WO-2006036634 | A2 | | 4/2006 |
| WO | WO-2006097527 | A1 | | 9/2006 |
| WO | WO-2006101940 | A2 | | 9/2006 |
| WO | WO-2008032222 | A2 | | 3/2008 |
| WO | WO-2008101693 | A2 | | 8/2008 |
| WO | WO-2008101693 | A3 | | 11/2008 |
| WO | WO-2009079790 | A1 | | 7/2009 |
| WO | WO-2010128504 | A2 | | 11/2010 |
| WO | WO-2011019393 | A2 | | 2/2011 |
| WO | WO-2011097148 | A2 | | 8/2011 |
| WO | WO-2011151685 | A1 | | 12/2011 |
| WO | WO-2012064892 | A1 | | 5/2012 |
| WO | WO-2012085650 | A1 | | 6/2012 |
| WO | WO-2012106343 | A2 | | 8/2012 |
| WO | WO-2013095275 | A1 | | 6/2013 |
| WO | WO-2013106643 | A2 | | 7/2013 |
| WO | WO-2013170113 | A1 | | 11/2013 |
| WO | WO-2013170115 | A1 | | 11/2013 |
| WO | WO-2013182274 | A1 | | 12/2013 |
| WO | WO-2013182652 | A1 | | 12/2013 |
| WO | WO-2014122184 | A1 | | 8/2014 |
| WO | WO-2015065891 | A1 | | 5/2015 |
| WO | WO-2017015660 | A1 | | 1/2017 |
| WO | WO-2017049470 | A1 | | 3/2017 |
| WO | WO-2017050259 | A1 | | 3/2017 |
| WO | WO-2017182802 | A1 | | 10/2017 |
| WO | WO-2018007864 | A1 | | 1/2018 |
| WO | WO-2018029657 | A1 | | 2/2018 |
| WO | WO-2018029658 | A1 | | 2/2018 |
| WO | WO-2018132759 | A1 | | 7/2018 |
| WO | WO-2018229738 | A1 | | 12/2018 |
| WO | WO-2019078915 | A1 | | 4/2019 |
| WO | WO-2019079536 | A1 | | 4/2019 |
| WO | WO-2019159110 | A1 | | 8/2019 |
| WO | WO-2019224171 | A1 | | 11/2019 |
| WO | WO-2020052620 | A1 | | 3/2020 |
| WO | WO-2020084435 | A1 | | 4/2020 |
| WO | WO-2020115715 | A1 | | 6/2020 |
| WO | WO-2020146263 | A1 | | 7/2020 |
| WO | WO-2020178721 | A1 | | 9/2020 |
| WO | WO-2020200335 | A1 | | 10/2020 |
| WO | WO-2020261230 | A1 | | 12/2020 |
| WO | WO-2021048431 | A1 | | 3/2021 |
| WO | WO-2021144720 | A1 | | 7/2021 |
| WO | WO-2021234642 | A1 | | 11/2021 |
| WO | WO-2022264037 | A1 | | 12/2022 |
| WO | WO-2023196841 | A2 | | 10/2023 |
| WO | WO-2025175092 | A1 | | 8/2025 |
| WO | WO-2025264957 | A2 | | 12/2025 |

OTHER PUBLICATIONS

Cheng, K.K., et al., "Highly stabilized curcumin nanoparticles tested in an in vitro blood-brain barrier model and in Alzheimer's disease Tg2576 mice," AAPS J 15(2):324-336, American Association of Pharmaceutical Scientists, United States (Apr. 2013).

Choi, K.D., and Choi, J.H., "Episodic Ataxias: Clinical and Genetic Features," J Mov Disord 9(3):129-135, Korean Movement Disorder Society, Korea (Sep. 2016).

Denier, C., et al., "High prevalence of CACNA1A truncations and broader clinical spectrum in episodic ataxia type 2," Neurology 52(9):1816-1821, Wolters Kluwer, United States (Jun. 1999).

Feil, K., et al., "Update on the Pharmacotherapy of Cerebellar Ataxia and Nystagmus," Cerebellum 15(1):38-42, Springer, United States (Feb. 2016).

Gandini, J., et al., "The neurological update: therapies for cerebellar ataxias in 2020," J Neurol 267(4):1211-1220, Springer Nature, Germany (Apr. 2020).

Griggs, R.C., et al., "Hereditary paroxysmal ataxia: response to acetazolamide," Neurology 28(12):1259-1264, Wolters Kluwer, United States (Dec. 1978).

Guterman, E.L., et al., "Pearls & Oy-sters: Episodic ataxia type 2: Case report and review of the literature," Neurology 86(23):e239-241, Wolters Kluwer, United States (Jun. 2016).

Hanson, L.R., and Frey, W.H., 2nd., "Intranasal delivery bypasses the blood-brain barrier to target therapeutic agents to the central nervous system and treat neurodegenerative disease," BMC Neurosci 9(Suppl 3):S5, BioMed Central, United Kingdom (Dec. 2008).

Ilg, W., "Consensus paper: management of degenerative cerebellar disorders," Cerebellum 13(2):248-268, Springer, United States (Apr. 2014).

Imbrici, P., et al., "Late-onset episodic ataxia type 2 due to an in-frame insertion in CACNA1A," Neurology 65(6):944-946, Wolters Kluwer, United States (Sep. 2005).

Patterson, M.C., et al., "Oral Miglustat in Niemann-Pick type C (NPC) Disease: 1-year Interim Analysis," 11th International Congress of Human Genetics—Brisbane, Australia (Aug. 6-10, 2006) Final Program and Abstract Book, Abstract 1513, p. 267, Human Genetics Society of Australasia, Australia (Aug. 2006).

Isaacs, D.A., et al., "Case report of novel CACNA1A gene mutation causing episodic ataxia type 2," SAGE Open Med Case Rep 5:1-3, SAGE Publications, United Kingdom (May 2017).

Jen, J., et al., "Clinical spectrum of episodic ataxia type 2," Neurology 62(1):17-22, Wolters Kluwer, United States (Jan. 2004).

Jen, J.C., et al., "Primary episodic ataxias: diagnosis, pathogenesis and treatment," Brain 130(Pt 10):2484-2493, Oxford University Press, United Kingdom (Oct. 2007).

Jen, J.C., and Wan, J., "Episodic ataxias," Handb Clin Neurol 155:205-215, Elsevier, Netherlands (2018).

Kabanov, A. V., and Batrakova, E.V., "New technologies for drug delivery across the blood brain barrier," Curr Pharm Des 10(12):1355-1363, Bentham Science Publishers, United Arab Emirates (2004).

Kalla, R., and Strupp, M., "Aminopyridines and Acetyl-DL-leucine: New Therapies in Cerebellar Disorders," Curr Neuropharmacol 17(1):7-13, Bentham Science Publishers, United Arab Emirates (Jan. 2019).

Kim, J.M., et al., "Episodic Ataxia Type 2 due to a Deletion Mutation in the CACNA1A Gene in a Korean Family," Journal of Clinical Neurology 2(4):268-271, Korean Neurological Association, Korea (Dec. 2006).

(56) References Cited

OTHER PUBLICATIONS

Kipfer, S., and Strupp, M., "The Clinical Spectrum of Autosomal-Dominant Episodic Ataxias," Mov Disord Clin Pract 1(4):285-290, Wiley, United States (Jul. 2014).
Lahde, A., et al. "Production of L-Leucine Nanoparticles under Various Conditions Using an Aerosol Flow Reactor Method," Journal of Nanomaterials 2008: Article 680897, Hindawi Publishing Corporation, United Kingdom (Jun. 2008).
Maksemous, N., et al., "Next-generation sequencing identifies novel CACNA1A gene mutations in episodic ataxia type 2," Mol Genet Genomic Med 4(2):211-222, Wiley, United States (Jan. 2016).
Mantuano, E., et al., "Identification of novel and recurrent CACNA1A gene mutations in fifteen patients with episodic ataxia type 2," J Neurol Sci 291(1-2):30-36, Elsevier, Netherlands (Apr. 2010).
Ophoff, R.A., et al., "Familial hemiplegic migraine and episodic ataxia type-2 are caused by mutations in the Ca2+ channel gene CACNL1A4," Cell 87(3):543-552, Cell Press, United States (Nov. 1996).
Patel, M.M., and Patel, B.M., "Crossing the Blood-Brain Barrier: Recent Advances in Drug Delivery to the Brain," CNS Drugs 31(2):109-133, Springer Nature, Germany (Feb. 2017).
Penkava, J., et al., "A novel pathogenic CACNA1A variant causing episodic ataxia type 2 (EA2) spectrum phenotype in four family members and a novel combined therapy," J Neurol 267(Suppl 1):181-184, Springer Nature, Germany (Dec. 2020).
Riant, F., et al., "Ataxies épisodiques génétiques [Hereditary episodic ataxia]," Rev Neurol 167(5):401-407, Elsevier, France (May 2011).
Richards, S., et al., "Standards and guidelines for the interpretation of sequence variants: a joint consensus recommendation of the American College of Medical Genetics and Genomics and the Association for Molecular Pathology," Genet Med 17(5):405-424, Elsevier, United States (May 2015).
Schniepp, R., et al., "Acetyl-DL-leucine improves gait variability in patients with cerebellar ataxia-a case series," Cerebellum Ataxias 3:8, BioMed Central, United Kingdom (Apr. 2016).
Sintas, C., et al., "Mutation Spectrum in the CACNA1A Gene in 49 Patients with Episodic Ataxia," Sci Rep 7(1):2514, Nature Publishing Group, United Kingdom (May 2017).
Strupp, M., et al., "Treatment of episodic ataxia type 2 with the potassium channel blocker 4-aminopyridine," Neurology 62(9):1623-1625, Wolters Kluwer, United States (May 2004).
Strupp, M., et al., "A randomized trial of 4-aminopyridine in EA2 and related familial episodic ataxias," Neurology 77(3):269-275, Wolters Kluwer, United States (Jul. 2011).
Strupp, M., et al., "Fampridine and acetazolamide for the treatment of episodic ataxia type 2 (EAT2TREAT): a randomised, double-blind, placebo-controlled, three-period crossover trial (2331)," Neurology 94(15_supplement): Abstract 2331, Wolters Kluwer, United States (Apr. 2020).
Abdulkhaleq, L.A., et al., "The Crucial roles of Inflammatory Mediators in Inflammation: A Review," Veterinary World 11(5):627-635, Veterinary World, India (May 2018).
Abel, L.A., et al., "Saccades in Adult Niemann-pick Disease Type C Reflect Frontal, Brainstem, and Biochemical Deficits," Neurology 72(12):1083-1086, Lippincott Williams & Wilkins, United States (Mar. 2009).
Oxbridge Solutions Limited, "Acetylation of drugs," GPnotebook, published on Jan. 1, 2018, accessed at https://gpnotebook.com/pages/surgery/acetylation-of-drugs, accessed on Feb. 26, 2025, 2 Pages.
Aerts, J.M.F.G., et al., "Biomarkers in the Diagnosis of Lysosomal Storage Disorders: Proteins, Lipids, and Inhibodies," Journal of Inherited Metabolic Disease 34(3):605-619, Wiley, United States (Jun. 2011).
Akita, H., et al., "Creation of a Thermostable NADP+-dependent D-amino Acid Dehydrogenase from Ureibacillus Thermosphaericus Strain A1 Meso-diaminopimelate Dehydrogenase by Site-directed Mutagenesis," Biotechnology Letters 34(9):1693-1699, Kluwer Academic Publishers, Netherlands (Sep. 2012).
Akita, H., et al., "Spectrophotometric Assay of D-isoleucine Using an Artificially Created D-amino Acid Dehydrogenase," Biotechnology Letters 36(11):2245-2248, Kluwer Academic Publishers, Netherlands (Nov. 2014).
Almanov, G.A., et al., Structure of Free Radicals in Irradiated Acetyl-L-leucine Single Crystals at 77 K, Journal of Structural Chemistry 29(2):216-220, Plenum Publishing Corporation, United States (Mar.-Apr. 1988).
Almanov, G.A., et al., "Structure of Free Radicals in Irradiated Acetyl-L-leucine Single Crystals," Khimia Vysokikh Energii 20(5):430-435, Nauka, Union of Soviet Socialist Republics (Sep.-Oct. 1986).
Amor, S., et al., "Inflammation in Neurodegenerative Diseases—an Update," Immunology 142(2):151-166, Blackwell Scientific Publications, United Kingdom (Jun. 2014).
Antonenko, L.M., "The Second Congress International Academy of Dizziness," Neurological Journal 20(4):51-53, Federal State Autonomous Institution "National Medical Research Center for Children's Health" of the Ministry of Health of the Russian Federation, Russia (Dec. 2015).
Arbuthnott, K., and Frank, J., "Trail Making Test, Part B as a Measure of Executive Control: Validation Using a Set-switching Paradigm," Journal of Clinical and Experimental Neuropsychology 22(4):518-528, Taylor and Francis Ltd., United Kingdom (Aug. 2000).
August, R.A., et al., "Stereospecific Synthesis of (2S,4R)-[5,5,5-2H3]-leucine," Tetrahedron Letters 33:4617-4620, Elsevier, Netherlands (Aug. 1992).
Baci, D., et al., "Acetyl-L-Carnitine Downregulates Invasion (CXCR4/CXCL12, MMP-9) and Angiogenesis (VEGF, CXCL8) Pathways in Prostate Cancer Cells: Rationale for Prevention and Interception Strategies," Journal of Experimental & Clinical Cancer Research 38(1):464, pp. 1-17, BioMed Central, United Kingdom (Nov. 2019).
Barclay, L.L., et al., "The String Test: an Early Behavioral Change in Thiamine Deficiency," Pharmacology, Biochemistry, and Behavior 14(2):153-157, Elsevier, United States (Feb. 1981).
Battisti, C., et al., "Adult Onset Niemann-pick Type C Disease: A Clinical, Neuroimaging and Molecular Genetic Study," Movement Disorders 18(11):1405-1409, Wiley, United States (Nov. 2003).
Beck, A.T., et al., "An Inventory for Measuring Depression," Archives of General Psychiatry 4:561-571, American Medical Association, United States (Jun. 1961).
Becker-Bense, S., et al., "P37. Effects of Acetyl-dl-leucine on the Cerebral Activation Pattern in Cerebellar Ataxia (FDG-PET Study)," Clinical Neurophysiology 126(8):e115, 1 page, Elsevier, (Aug. 2015).
Belarbi, K., et al., "TNF-a Protein Synthesis Inhibitor Restores Neuronal Function and Reverses Cognitive Deficits Induced by Chronic Neuroinflammation," Journal of Neuroinflammation 9:23, pp. 1-13, BioMed Central, United Kingdom (Jan. 2012).
Belikov, V.G., Pharmaceutical Chemistry: Manual, 4th edition, pp. 27-29, MEDpress-inform, Moscow, Russia (2007).
Benussi, A., et al., "Phenotypic Heterogeneity of Niemann-pick Disease Type C in Monozygotic Twins," Journal of Neurology 262(3):642-647, Springer Science+Business Media, United States (Mar. 2015).
Beyer, L., et al., "Clinical Routine FDG-PET Imaging of Suspected Progressive Supranuclear Palsy and Corticobasal Degeneration: A Gatekeeper for Subsequent Tau-PET Imaging?" Frontiers in Neurology 9:483, pp. 1-9, Frontiers Research Foundation, Switzerland (Jun. 2018).
Bingham, A.L., et al., "Over one Hundred Solvates of Sulfathiazole," Chemical Communications, pp. 603-604, The Royal Society of Chemistry, United Kingdom (2001).
Boland, B., et al., "Macroautophagy is Not Directly Involved in the Metabolism of Amyloid Precursor Protein," The Journal of Biological Chemistry 285(48):37415-37426, American Society for Biochemistry and Molecular Biology, United States (Nov. 2010).
Brandt, T., et al., "Plasticity of the Vestibular System: Central Compensation and Sensory Substitution for Vestibular Deficits," Advances in Neurology 73:297-309, Lippincott Williams & Wilkins, United States (1997).
Waring, M.J., "Defining optimum lipophilicity and molecular weight ranges for drug candidates—Molecular weight dependent lower

(56) References Cited

OTHER PUBLICATIONS logD limits based on permeability," Bioorg Med Chem Lett 19(10):2844-2851, Elsevier Ltd., United Kingdom (May 2009).
Bremova, T., et al., "Vestibular Function in Patients With Niemann-pick Type C Disease," Journal of Neurology 263(11):2260-2270, Springer Science+Business Media, United States (Nov. 2016).
Bremova-Ertl, A., et al., "EPR1131 Acetyl-Leucine Slows Disease Progression in Lysosomal Storage Disorders," European Journal of Neurology 27(1):181, XP009522922, (May 2020).
Bremova-Ertl, T., et al., "Clinical, Ocular Motor, and Imaging Profile of Niemann-pick Type C Heterozygosity," Neurology 94(16):e1702-e1715, Lippincott Williams & Wilkins, United States (Apr. 2020).
Bremova-Ertl, T., et al., "Oculomotor and Vestibular Findings in Gaucher Disease Type 3 and Their Correlation with Neurological Findings," Frontiers in Neurology 8:711, pp. 1-19, Frontiers Research Foundation, Switzerland (Jan. 2018).
Brendel, M., et al., "[18F]-THK5351 PET Correlates with Topology and Symptom Severity in Progressive Supranuclear Palsy," Frontiers in Aging Neuroscience 9:440, pp. 1-12, Frontiers Media, Switzerland (Jan. 2018).
Caira, M.R., et al., "Preparation and Crystal Characterization of a Polymorph, a Monohydrate, and an Ethyl Acetate Solvate of the Antifungal Fluconazole," Journal of Pharmaceutical Sciences 93(3):601-611, Elsevier, United States (Mar. 2004).
Cardellicchio, C., et al., "Synthesis of a-amino Acid Derivatives by Copper(I)-catalyzed Conjugate Addition of Grignard Reagents to Methyl Acetamidoacrylate," Tetrahedron Letters 26(36):4387-4390, Pergamon Press Ltd, United Kingdom (May 1985).
Chakrabarti, S., et al., "Upregulation of Suppressor of Cytokine Signaling 3 in Microglia by Cinnamic Acid," Current Alzheimer Research 15(10):894-904, Bentham Science Publishers, United Arab Emirates (2018).
Champion, H., et al., "Dietary Modifications in Patients Receiving Miglustat," Journal of Inherited Metabolic Disease 33 (Suppl 3):S379-83, Wiley, United States (Dec. 2010).
Chatterjee, B., et al., "Selective a-Deuteration of Amines and Amino Acids Using $D_2O$," Organic Letters 18(22):5892-5895, American Chemical Society, United States (Nov. 2016).
Chen, W-W., et al., "Role of Neuroinflammation in Neurodegenerative Diseases (Review)," Molecular Medicine Reports 13(4):3391-3396, D. A. Spandidos, Greece (Apr. 2016).
Cherry, J.D., et al., "Neuroinflammation and M2 Microglia: the Good, the Bad, and the Inflamed," Journal of Neuroinflammation 11:98, pp. 1-15, BioMed Central, United Kingdom (Jun. 2014).
Chida, J., et al., "An Efficient Extraction Method for Quantitation of Adenosine Triphosphate in Mammalian Tissues and Cells," Analytica Chimica Acta 727:8-12, Elsevier, Netherlands (May 2012).
Coccia, M., et al., "IL-1β Mediates Chronic Intestinal Inflammation by Promoting the Accumulation of IL-17A Secreting Innate Lymphoid Cells and CD4(+) Th17 Cells," The Journal of Experimental Medicine 209(9):1595-609, Rockefeller University Press, United States (Aug. 2012).
Cortina-Borja, M., et al., "Annual Severity Increment Score as a Tool for Stratifying Patients with Niemann-Pick disease type C and for Recruitment to Clinical Trials," Orphanet Journal of Rare Diseases 13(1):143, BioMed Central, United Kingdom (Aug. 2018).
Cupidi, C., et al., "Role of Niemann-Pick Type C Disease Mutations in Dementia," Journal of Alzheimer's Disease 55(3):1249-1259, SAGE Publications, United States (2017).
Davies, S.G., et al., "Asymmetric Conjugate Reductions with Samarium Diiodide: Asymmetric Synthesis of (2S,3R)- and (2S,3S)-[2-2H,3-2H]-leucine-(S)-phenylalanine Dipeptides and (2S,3R)- [2-(2)H,3-2H]-phenylalanine Methyl Ester," Organic Biomolecular Chemistry 3(8):1435-1447, Royal Society of Chemistry, United Kingdom (Apr. 2005).
Debray, F-G., et al., "Disorders of Mitochondrial Function," Current Opinion in Pediatrics 20(4):471-482, Lippincott Williams and Wilkins, United States (Aug. 2008).
Dieringer, N., "'Vestibular Compensation': Neural Plasticity and Its Relations to Functional Recovery After Labyrinthine Lesions in Frogs and Other Vertebrates," Progress in Neurobiology 46(2-3):97-129, Elsevier, Netherlands (Jun. 1995).
Disabato, D.J., et al., "Neuroinflammation: the Devil Is in the Details," Journal of Neurochemistry 139 Suppl 2(Suppl 2):136-153, Wiley on behalf of the International Society for Neurochemistry, United Kingdom (Oct. 2016).
Douglass, A., et al., "Behavioral Variant Frontotemporal Dementia Performance on a Range of Saccadic Tasks," Journal of Alzheimer's Disease 65(1):231-242, SAGE Publications, United States (2018).
Dyck, L.E., et al., "Effects of Deuterium Substitution on the Catabolismof Beta- Phenylethylamine: an in Vivo Study," Journal of Neurochemistry 46(2):399-404, Wiley, United Kingdom (Feb. 1986).
Dyson, G., et al., "The Mechanism of Action of Medicinal Substances," in *Chemistry of Synthetic Drugs*, pp. 12-19, Mir Publishers, Moscow, Union of Soviet Socialist Republics (1964).
Ehrensperger, M.M., et al., "Early Detection of Alzheimer's Disease With a Total Score of the German CERAD," Journal of the International Neuropsychological Society 16(5):910-920, Cambridge University Press, United Kingdom (Sep. 2010).
English language translation of Office Action for Russian Patent Application No. 2021119633, dated May 22, 2023, Federal Service for Intellectual Property, Moscow, Russia, 6 pages.
Fang, J., et al., "Dose Staggering as a Strategy to Reduce Drug—drug Interactions Due to Reversible Enzyme Inhibition Between Orally Administered Drugs With High First Pass Effect: A Computer Simulation Study," Biopharmaceutics & Drug Disposition 21(7):249-259, Wiley, United Kingdom (Oct. 2000).
Final Office Action for U.S. Appl. No. 17/247,757, mailed on May 5, 2023, 17 pages.
Fletcher, M.D., et al., "Three Approaches to the Synthesis of L-leucine Selectively Labelled with Carbon-13 or Deuterium in Either Diastereotopic Methyl Group ," Journal of the Chemical Society 43-52, 10 pages, Royal Society of Chemistry, United Kingdom (Jan. 2000).
Frank-Cannon, T.C., et al., "Does Neuroinflammation Fan the Flame in Neurodegenerative Diseases?" Molecular Neurodegeneration 4:47, pp. 1-13, BioMed Central, United Kingdom (Nov. 2009).
Frankola, K.A., et al., "Targeting TNF-a to Elucidate and Ameliorate Neuroinflammation in Neurodegenerative Diseases," CNS & Neurological Disorders Drug Targets 10(3):391-403, Bentham Science Publishers, United Arab Emirates (May 2011), 25 pages.
Giese, A.K., et al., "A Novel, Highly Sensitive and Specific Biomarker for Niemann-pick Type C1 Disease," Orphanet Journal of Rare Diseases 10:78, 8 pages, BioMed Central, United Kingdom (Jun. 2015).
Ginger, M.L., et al., "The Biosynthetic Incorporation of the Intact Leucine Skeleton Into Sterol by the Trypanosomatid Leishmania Mexicana," The Journal of Biological Chemistry 276(15):11674-11682, Elsevier Inc, United States (Apr. 2001).
Gray, A.J., et al., "Olfactory Identification is Impaired in Clinic-based Patients With Vascular Dementia and Senile Dementia of Alzheimer Type," International Journal of Geriatric Psychiatry 16(5):513-517, Wiley, United Kingdom (May 2001).
Greer, W.L., et al., "Mutations in NPC1 Highlight a Conserved NPC1-specific Cysteine-rich Domain," American Journal of Human Genetics 65(5):1252-1260, Cell Press, United States (Nov. 1999).
Gu, Y., et al., "Role of TNF in Mast Cell Neuroinflammation and Pain," Journal of Biological Regulators and Homeostatic Agents 29(4):787-791, Biolife, Italy (Oct.-Dec. 2015).
Günther, L., et al., "N-Acetyl-L-Leucine Accelerates Vestibular Compensation after Unilateral Labyrinthectomy by Action in the Cerebellum and Thalamus," PLoS One, 10(3): e0120891, 18 pages, Plos One, United States (Mar. 2015).
Habbas, S., et al., "Neuroinflammatory TNFa Impairs Memory via Astrocyte Signaling," Cell 163(7):1730-1741, Cell Press, United States (Dec. 2015).
Hammond, N., et al., "The Complexity of a Monogenic Neurodegenerative Disease: More Than Two Decades of Therapeutic Driven Research Into Niemann-pick Type C Disease," Biochimica et Biophysica

(56) References Cited

OTHER PUBLICATIONS

Acta—Molecular and Cell Biology of Lipids 1864(8):1109-1123, Elsevier, Netherlands (Aug. 2019).
Harris, R.A., et al., "Overview of the Molecular and Biochemical Basis of Branched-chain Amino Acid Catabolism," The Journal of Nutrition 135(6 Suppl):1527S-1530S, Elsevier, United States (Jun. 2005).
Harris, R.A., et al., "Physiological Covalent Regulation of Rat Liver Branched-chain Alpha-ketoacid Dehydrogenase," Archives of Biochemistry and Biophysics 243(2):542-555, Academic Press, United States (Dec. 1985).
Harzer, K., et al., "Niemann-pick Disease Type C: New Aspects in a Long Published Family—Partial Manifestations in Heterozygotes," JIMD Reports 12:25-29, Springer, Germany (May 2013).
Havla, J., et al., "Retinal Axonal Degeneration in Niemann-pick Type C Disease," Journal of Neurology 267(7):2070-2082, Springer Science+Business Media, United States (Jul. 2020).
Heitz, C., et al., "Cognitive Impairment Profile in Adult Patients With Niemann Pick Type C Disease," Orphanet Journal of Rare Diseases 12(1):166, pp. 1-10, BioMed Central, United Kingdom (Oct. 2017).
Heron, B., et al., "Miglustat Therapy in the French Cohort of Paediatric Patients with Niemann-Pick Disease Type C," Orphanet Journal of Rare Diseases 7:36, pp. 1-14, BioMed Central, United Kingdom (Jun. 2012).
Hill, R.K., et al., "Synthesis of (2S,4S)- and (2S,4R)-[5,5,5-$^2H_3$] Leucine from (R)-pulegone[1]," Canadian Journal of Chemistry 72(1):110-113, NRC Research Press, Canada (Jan. 1994).
Homer, R.J., et al., "The Use of Cystathionine Gamma-synthase in the Production of Alpha and Chiral Beta Deuterated Amino Acids," Analytical Biochemistry 215(2):211-215, Elsevier, United States (Dec. 1993).
Hong, H., et al., "Pathophysiological Role of Neuroinflammation in Neurodegenerative Diseases and Psychiatric Disorders," International Neurourology Journal 20(Suppl 1):S2-S7, Korean Continence Society, Korea (May 2016).
Hoyles, K., and Sharma, J.C., "Olfactory Loss as a Supporting Feature in the Diagnosis of Parkinson's Disease: A Pragmatic Approach," Journal of Neurology 260(12):2951-2958, Springer Science+Business Media, United States (Dec. 2013).
Huang, H., et al., "Effects of Acetylleucine on the Recovery of Motor Balance and Discharge Activity of Neurons in the Medial Vestibular Nucleus in Rats after Labyrinthine Injury," Collection of Abstracts of the 21st National Congress and Academic Conference of the Chinese Physiological Society, Abstract 243, p. 66, Chinese Physiological Society, China (Oct. 2002).
Huang, J-Y., et al., "Neuroimaging Findings in a Brain with Niemann-pick Type C Disease, " Journal of the Formosan Medical Association 110(8):537-542, Formosan Medical Association, Singapore (Aug. 2011).
Hummel, T., et al., "'Sniffin' Sticks : Olfactory Performance Assessed by the Combined Testing of Odor Identification, Odor Discrimination and Olfactory Threshold," Chemical Senses 22(1):39-52, Oxford University Press, United Kingdom (Feb. 1997).
Inacio, A.R., et al., "Endogenous IFN-β Signaling Exerts Anti-inflammatory Actions in Experimentally Induced Focal Cerebral Ischemia," Journal of Neuroinflammation 12:211, pp. 1-18, BioMed Central, United Kingdom (Nov. 2015).
International Search Report and Written Opinion for Application No. PCT/IB2019/060525, mailed on Feb. 3, 2020, 14 pages.
International Search Report and Written Opinion for Application No. PCT/IB2020/056096, mailed on Sep. 29, 2020, 11 pages.
International Search Report and Written Opinion for Application No. PCT/IB2021/050236, mailed on Apr. 12, 2021, 10 pages.
International Search Report and Written Opinion of International Application No. PCT/IB2020/051767, mailed on Jul. 30, 2020, 19 pages.
Jeyakumar, M., et al., "Central Nervous System Inflammation is a Hallmark of Pathogenesis in Mouse Models of GM1 and GM2 Gangliosidosis," Brain 126(Pt 4):974-987, Oxford University Press, United Kingdom (Apr. 2003).
Jeyakumar, M., et al., "Delayed Symptom Onset and Increased Life Expectancy in Sandhoff Disease Mice Treated With N-butyldeoxynojirimycin," Proceedings of the National Academy of Sciences of the United States of America 96(11):6388-6393, National Academy of Sciences, United States (May 1999).
Jha, M.K., et al., "Pyruvate Dehydrogenase Kinases in the Nervous System: Their Principal Functions in Neuronal-glial Metabolic Interaction and Neuro-metabolic Disorders," Current Neuropharmacology 10(4):393-403, Bentham Science Publishers, United Arab Emirates (Dec. 2012).
Johnen, A., et al., "Distinguishing Neurocognitive Deficits in Adult Patients With NP-C From Early Onset Alzheimer's Dementia," Orphanet Journal of Rare Diseases 13(1):91, 10 pages, BioMed Central, United Kingdom (Jun. 2018).
Josephs, K.A., et al., "Heterozygous Niemann-Pick Disease type C Presenting with Tremor," Neurology 63(11):2189-2190, Lippincott Williams & Wilkins, United States (Dec. 2004).
Karve, I.P., et al., "Ablation of Type-1 IFN Signaling in Hematopoietic Cells Confers Protection Following Traumatic Brain Injury," eNeuro 3(1):ENEURO.0128-15, Society for Neuroscience, United States (Feb. 2016).
Kato, M., et al., "Structural Basis for Inactivation of the Human Pyruvate Dehydrogenase Complex by Phosphorylation: Role of Disordered Phosphorylation Loops," Structure 16(12):1849-1859, Cell Press, United States (Dec. 2008).
Kelly, N.M., et al., "Chemo-enzymatic Synthesis of Isotopically Labelled L-valine, L-isoleucine and Allo-isoleucine, " Tetrahedron Letters 37(9):1517-1520, Elsevier, United Kingdom (Feb. 1996).
Kelly, N.M., et al., "Methods for the Synthesis of L-Leucine Selectively Labelled with Carbon-13 or Deuterium in either Diastereotopic Methyl Group," Tetrahedron Letters 36:8315-8318, Elsevier, United Kingdom (Nov. 1995).
Kelly, N.M., et al., "Syntheses of Amino Acids Incorporating Stable Isotopes," Nat Prod Rep 14:205-219, Royal Society of Chemistry, United Kingdom (Jan. 1997).
Kennedy, B.E., et al., "Pre-symptomatic Activation of Antioxidant Responses and Alterations in Glucose and Pyruvate Metabolism in Niemann-pick Type C1-deficient Murine Brain," PloS One 8(12):e82685, pp. 1-18, Public Library of Science, United States (Dec. 2013).
Kennedy, B.E., et al., "Presymptomatic Alterations in Amino Acid Metabolism and DNA Methylation in the Cerebellum of a Murine Model of Niemann-pick Type C Disease," The American Journal of Pathology 186(6):1582-1597, Elsevier, United States (Jun. 2016).
Khelimsky, A.M., et al., *Clinic Picture, Diagnosis and Treatment of Cranio-Brain Injuries*, pp. 22-24 (2003), 8 pages.
Kimball,S.R., et al., "Leucine Regulates Translation of Specific mRNAs in L6 Myoblasts through mTOR-mediated Changes in Availability of eIF4E and Phosphorylation of Ribosomal Protein S6," The Journal of Biological Chemistry 274(17):11647-11652, American Society for Biochemistry and Molecular Biology, United States (Apr. 1999).
Kinney, C.R., and Adams, R., "Dideuteriovaline and Dideuterioleucine," Journal of the American Chemical Society 59(5):897-898, American Chemical Society, United States (May 1937).
Kirkegaard, T., et al., "Heat Shock Protein-based Therapy as a Potential Candidate for Treating the Sphingolipidoses," Science Translational Medicine 8(355):355ra118, American Association for the Advancement of Science, United States (Sep. 2016).
Klionsky, D.J., and Emr, S.D., "Autophagy as a Regulated Pathway of Cellular Degradation," Science 290(5497):1717-1721, American Association for the Advancement of Science, United States (Dec. 2000).
Kluenemann, H.H., et al., "Parkinsonism Syndrome in Heterozygotes for Niemann-Pick C1," Journal of the Neurological Sciences, 335(1-2):219-220, Elsevier, Netherlands (Dec. 2013).
Kresojevic, N., et al., "Mutations in Niemann Pick Type C Gene Are Risk Factor for Alzheimer's Disease," Medical Hypotheses 83:559-562, Elsevier, United States (Nov. 2014).

(56) References Cited

OTHER PUBLICATIONS

Kumar, A., et al., "Niemann-Pick Disease Type C: Unique 2-Deoxy-2[18F] Fluoro-D-Glucose PET Abnormality," Pediatric Neurology, 44(1): 57-60, Elsevier, Netherlands (Jan. 2011).
Kummerer, K., "Pharmaceuticals in the Environment, " Annual Review of Environment and Resources 35:57-75, Annual Reviews, United States (Aug. 2010).
Lappalainen, U., et al., "Interleukin-1beta Causes Pulmonary Inflammation, Emphysema, and Airway Remodeling in the Adult Murine Lung," American Journal of Respiratory Cell and Molecular Biology 32(4):311-318, American Thoracic Society, United States (Apr. 2005).
Lee, J.H., et al., "Anti-inflammatory and Anti-genotoxic Activity of Branched Chain Amino Acids (BCAA) in Lipopolysaccharide (LPS) Stimulated Raw 264.7 Macrophages," Food Science and Biotechnology 26(5):1371-1377, Korean Society of Food Science and Technology, Korea (Aug. 2017).
Liang, H., and Ward, W.F., "PGC-1alpha: A Key Regulator of Energy Metabolism," Advances in Physiology Education 30(4):145-151, American Physiological Society, United States (Dec. 2006).
Liu, S.Q., et al., Leucine Alters Immunoglobulin a Secretion and Inflammatory Cytokine Expression Induced by Lipopolysaccharide via the Nuclear Factor-?b Pathway in Intestine of Chicken Embryos, Animal: An International Journal of Animal Bioscience 12(9):1903-1911, Elsevier, United Kingdom (Sep. 2018).
Lloyd-Evans, E., and Platt, F.M., "Lipids on Trial: the Search for the Offending Metabolite in Niemann-Pick type C Disease," Traffic 11(4):419-428, John Wiley & Sons, United Kingdom (Apr. 2010).
Lobato, J.B., et al., "Biomarkers in Lysosomal Storage Diseases," Diseases 4(4):40, 17 pages, MDPI AG, Switzerland (Dec. 2016).
Luppa, M., et al., "Age-related predictors of institutionalization: results of the German study on ageing, cognition and dementia in primary care patients (AgeCoDe)," Social Psychiatry and Psychiatric Epidemiology 47(2):263-270, Springer Science+Business Media, United States (Feb. 2012).
Miyanoiri, Y., et al., "Differential Isotope-labeling for Leu and Val Residues in a Protein by *E. coli* Cellular Expression Using Stereo-specifically Methyl Labeled Amino Acids," Journal of Biomolecular NMR 57(3):237-249, Springer, Netherlands (Nov. 2013).
Moss, G.P., "Basic Terminology of Stereochemistry," Pure and Applied Chemistry 68(12):2193-2222, IUPAC, United Kingdom (1996).
Murphy, M.P., and Hartley, R.C., "Mitochondria as a Therapeutic Target for Common Pathologies," Nature Reviews Drug Discovery 17(12):865-886, Nature Pub. Group, United Kingdom (Dec. 2018).
Nagamori, S., et al., "Structure-activity Relations of Leucine Derivatives Reveal Critical Moieties for Cellular Uptake and Activation of mTORC1-mediated Signaling," Amino Acids 48(4):1045-1058, Springer-Verlag, Austria (Apr. 2016).
Nakajima, N., et al., "Enzymatic Conversion of Racemic Methionine to the L-enantiomer," Journal of the Chemical Society 13:947-948, Royal Society of Chemistry, United Kingdom (1990).
Neuzil, E., et al., "N-acetyl-DL-leucine, a Symptomatic Drug for Vertigo," Bulletin-societe De Pharmacie De Bordeaux 141(1-4):15-38, La Société, France (2002).
Neville, D.C., et al., "Analysis of Fluorescently Labeled Glycosphingolipid-derived Oligosaccharides Following Ceramide Glycanase Digestion and Anthranilic Acid Labeling," Analytical Biochemistry 331(2):275-282, Academic Press, United States (Aug. 2004).
Niyazov, D.M., et al., "Primary Mitochondrial Disease and Secondary Mitochondrial Dysfunction: Importance of Distinction for Diagnosis and Treatment," Molecular Syndromology 7(3):122-137, S. Karger, Switzerland (Jul. 2016).
Non-Final Office Action for U.S. Appl. No. 17/247,757, mailed on Oct. 4, 2023, 16 pages.
Non-Final Office Action for U.S. Appl. No. 17/247,757, mailed on Oct. 6, 2022, 14 pages.
Notice of Allowance for U.S. Appl. No. 17/247,757, mailed on Apr. 10, 2024, 13 pages.
Oba, M., et al., "Stereoselective Deuterium-labelling of Diastereotopic Methyl and Methylene Protons of L-leucine, " Tetrahedron Letters 39:1595-1598, Elsevier, Netherlands (Mar. 1998).
Oba, M., et al., "Synthesis of (13)C/D Doubly Labeled L-leucines: Probes for Conformational Analysis of the Leucine Side-chain," The Journal of Organic Chemistry 66(17):5919-5922, American Chemical Society, United States (Aug. 2001).
Oba, M., et al., "Synthesis of L-threo- and L-erythro-[1-$^{13}$C, 2,3-$^{2}H_2$] Amino Acids: Novel Probes for Conformational Analysis of Peptide Side Chains" Journal of the Chemical Society 12:1603-1609, Royal Society of Chemistry, United Kingdom (1995).
Olichney, J.M., et al., "Anosmia is Very Common in the Lewy Body Variant of Alzheimer's Disease," Journal of Neurology, Neurosurgery, and Psychiatry 76(10):1342-1347, BMJ Publishing Group, United Kingdom (Oct. 2005).
Orasji, S.S.S., et al., "Olfactory Dysfunction in Behavioral Variant Frontotemporal Dementia," Clinical Neurology and Neurosurgery 141:106-110, Elsevier, Netherlands (Feb. 2016).
Pankiv, S., et al., "P62/SQSTM1 Binds Directly to Atg8/LC3 to Facilitate Degradation of Ubiquitinated Protein Aggregates by Autophagy," The Journal of Biological Chemistry 282(33):24131-24145, American Society for Biochemistry and Molecular Biology, United States (Aug. 2007).
Patterson, M., et al., "Niemann-Pick Disease Type C," in GeneReviews® [Internet], Adam, M.P., et al., eds., 2 pages, University of Washington, Seattle, United States (Dec. 10, 2020).
Patterson, M.C., et al., "Disease and Patient Characteristics in NP-C Patients: Findings From an International Disease Registry," Orphanet Journal of Rare Diseases 8:12, 10 pages, BioMed Central, United Kingdom (Jan. 2013).
Patterson, M.C., et al., "Long-term Miglustat Therapy in Children With Niemann-Pick Disease Type C," Journal of Child Neurology 25(3): 300-305, Sage Publications, United States (Mar. 2010).
Patterson, M.C., et al., "Miglustat for treatment of Niemann-Pick C disease: a Randomised Controlled Study," The Lancet. Neurology 6(9):765-772, Lancet Pub. Group, United Kingdom (Sep. 2007).
Patterson, M.C., et al., "Recommendations for the Detection and Diagnosis of Niemann-Pick Disease Type C: An update," Neurology: Clinical Practice 7:499-511, Lippincott Williams and Wilkins, United States (Dec. 2017).
Patterson, M.C., et al., "Recommendations for the Diagnosis and Management of Niemann-Pick Disease Type C: An update," Molecular Genetics and Metabolism 106(3):330-344, Academic Press, United States (Jul. 2012).
Wang, G., et al., "Intestinal OCTN2- and MCT1-targeted drug delivery to improve oral bioavailability," Asian J Pharm Sci 15(2):158-173, Shenyang Pharmaceutical University, China (Mar. 2020).
Vanier, M.T., et al., "Niemann-Pick disease type C," Orphanet Journal of Rare Diseases 5:16, pp. 1-18, BioMed Central, United Kingdom (Jun. 2010).
Pelz, J.O., et al., "Failure to Confirm Benefit of Acetyl-dl-leucine in Degenerative Cerebellar Ataxia: A Case Series," Journal of Neurology 262(5):1373-1375, Springer-Verlag, Germany (2015).
Pentchev, P.G., et al., "A Lysosomal Storage Disorder in Mice Characterized by a Dual Deficiency of Sphingomyelinase and Glucocerebrosidase," Biochimica Et Biophysica Acta 619(3):669-679, Elsevier Pub. Co, Netherlands (Sep. 1980).
Pineda, M., et al., "Miglustat in Patients with Niemann-Pick Disease Type C (NP-C): a Multicenter Observational Retrospective Cohort Study," Molecular Genetics and Metabolism 98(3):243-249, Academic Press, United States (Nov. 2009).
Platt, F., and Strupp, M., "An Anecdotal Report by an Oxford Basic Neuroscientist: Effects of Acetyl-DL-leucine on Cognitive Function and Mobility in the Elderly," Journal of Neurology 263(6):1239-1240, Springer-Verlag, Germany (Jun. 2016).
Platt, F.M., "Emptying the Stores: Lysosomal Diseases and Therapeutic Strategies," Nature Reviews Drug Discovery 17(2):133-150, Nature Pub. Group, United Kingdom (Feb. 2018).
Platt, F.M., et al., "The Cell Biology of Disease: Lysosomal Storage Disorders: the Cellular Impact of Lysosomal Dysfunction," The Journal of Cell Biology 199(5):723-734, Rockefeller University Press, United States (Nov. 2012).

(56) References Cited

OTHER PUBLICATIONS

Pliss, L., et al., "Cerebral Developmental Abnormalities in a Mouse With Systemic Pyruvate Dehydrogenase Deficiency," PloS One 8(6):e67473, pp. 1-14, Public Library of Science, United States (Jun. 2013).
Postuma, R.B., et al., "Advances in Markers of Prodromal Parkinson Disease," Nature Reviews Neurology 12(11):622-634, Nature Publishing Group, United Kingdom (Oct. 2016).
Pretegiani, E., and Optican, M.L., "Eye Movements in Parkinson's Disease and Inherited Parkinsonian Syndromes," Frontiers in Neurology 8:592, 7 pages, Frontiers Research Foundation, Switzerland (Nov. 2017).
Priestman, D.A., et al., "N-butyldeoxynojirimycin Causes Weight Loss as a Result of Appetite Suppression in Lean and Obese Mice," Diabetes, Obesity and Metabolism 10(2):159-166, Wiley-Blackwell, United Kingdom (Feb. 2008).
Probert, F., et al., "NMR Analysis Reveals Significant Differences in the Plasma Metabolic Profiles of Niemann Pick C1 Patients, Heterozygous Carriers, and Healthy Controls," Scientific Reports 7(1):6320, Nature Publishing Group, United Kingdom (Jul. 2017).
Pubchem, "Acetylleucine," CID 1995, accessed at https://pubchem.ncbi.nlm.nih.gov/compound/1995#section= 2D-Structure, 3 pages.
Ray, K.K., "Interleukin-1 Revisited: Further Insights Into Its Role in Atherosclerosis and as a Potential Therapeutic Target for Treatment," Journal of the American College of Cardiology 63(17):1735-1738, Elsevier Biomedical, United States (May 2014).
Ren, K., and Torres, R., "Role of Interleukin-1beta during Pain and Inflammation," Brain Research Reviews 60(1):57-64, Elsevier B.V., Netherlands (2009).
Reunert, J., et al., "Niemann-Pick Type C-2 Disease: Identification by Analysis of Plasma Cholestane-3β, 5a, 6β-Triol and Further Insight into the Clinical Phenotype," JIMD Reports 23:17-26, Wiley, United States (Mar. 2015).
Rose, J.E., et al., "Stereospecific Synthesis of a-Deuteriated a-Amino Acids: Regiospecific Deuteriation of Chiral 3-Isopropyl-2,5-Dimethoxy-3,6-Dihydropyrazines," Journal of the Chemical Society 2:157-165, Royal Society of Chemistry, United Kingdom (1995).
Royall, D.R., et al., "CLOX: an Executive Clock Drawing Task," Journal of Neurology, Neurosurgery, and Psychiatry 64(5):588-594, BMJ Publishing Group, United Kingdom (May 1998).
Rozenbaum, H., "How to Evaluate the Risk-benefit Ratio of the Low-dose Hormone Replacement Therapy?" The Journal of Steroid Biochemistry and Molecular Biology 102(1-5):256-260, Pergamon, United Kingdom (Dec. 2006).
Ruiz-Rodado, V., et al., "1h NMR-linked Metabolomics Analysis of Liver From a Mouse Model of NP-C1 Disease," Journal of Proteome Research 15(10):3511-3527, American Chemical Society, United States (Oct. 2016).
Sanchez-Cubillo, I., et al., "Construct Validity of the Trail Making Test: Role of Task-switching, Working Memory, Inhibition/interference Control, and Visuomotor Abilities," Journal of the International Neuropsychological Society, 15(3):438-450, Cambridge University Press, United Kingdom (May 2009).
Sandhoff, L., and Harzer, K., "Gangliosides and Gangliosidoses: Principles of Molecular and Metabolic Pathogenesis," The Journal of Neuroscience 33(25):10195-10208, Society for Neuroscience, United States (Jun. 2013).
Sango, K., et al., "Mouse Models of Tay-sachs and Sandhoff Diseases Differ in Neurologic Phenotype and Ganglioside Metabolism," Nature Genetics 11(2):170-176, Nature Pub. Co, United States (Oct. 1995).
Sarkar, C., et al., "Impaired Autophagy Flux is Associated With Neuronal Cell Death After Traumatic Brain Injury," Autophagy 10(12):2208-2222, Taylor & Francis, United States (2014).
Sarkar, C., et al., "N-acetyl-L-leucine Treatment Attenuates Neuronal Cell Death and Suppresses Neuroinflammation After Traumatic Brain Injury in Mice," bioRxiv, pp. 1-20, Retrieved from the Internet:[https://www.biorxiv.org/content/10.1101/759894v1.full.pdf], (Sep. 8, 2019).
Sarkar, C., et al., "PLA2G4A/cPLA2-Mediated Lysosomal Membrane Damage Leads to Inhibition of Autophagy and Neurodegeneration After Brain Trauma," Autophagy 16(3):466-485, Taylor & Francis, United States (Mar. 2020).
Scaglione, C., et al., "REM Sleep behaviour Disorder in Parkinson's Disease: A Questionnaire-based Study," Neurological Sciences 25(6):316-321, Springer-Verlag Italia, Italy (Feb. 2005).
Schneider, E., et al., "EyeSeeCam: An Eye Movement-Driven Head Camera for the Examination of Natural Visual Exploration," Basic and Clinical Aspects of Vertigo and Dizziness: Annals of the New York Academy of Sciences, 1164: 461-7, New York Academy of Sciences, United States (May 2009).
Schneider, S., "Do Heterozygous Mutations of Niemann-Pick Type C Predispose to Late-onset Neurodegeneration: A Review of the Literature," Journal of Neurology 268(6):2055-2064, Springer-Verlag, Germany (Jun. 2021).
Wiederschain, G.Y., "The Metabolic and Molecular Bases of Inherited Disease," Biochemistry (Moscow) 67(5):611-612, Pleiades Publishing, Ltd., Russia (May 2002).
Sevin, M., et al., "The Adult Form of Niemann-Pick Disease Type C," Brain 130:120-133, Oxford University Press, United Kingdom (Jan. 2007).
Shah, S.A., et al., "Enantiomeric Conversion of Racemic Amino Acid Mixtures via an Oxidase-Aminotransferase Coupled System," Tetrahedron Letters 35:29-32, Elsevier, United Kingdom (Jan. 1994).
Shao, L., and Hewitt, M.C., "The Kinetic Isotope Effect in the Search for Deuterated Drugs," Drug News & Perspectives 23(6)398-404, Thomson Reuters, United States (Jul.-Aug. 2010).
Shibanuma, M., et al., "Inhibition by N-acetyl-L-cysteine of Interleukin-6 mRNA Induction and Activation of NF Kappa B by Tumor Necrosis Factor Alpha in a Mouse Fibroblastic Cell Line, Balb/3T3," FEBS Letters 353(1):62-66, John Wiley & Sons Ltd, United Kingdom (Oct. 1994).
Sidransky, E., et al., "Multicenter Analysis of Glucocerebrosidase Mutations in Parkinson's Disease," The New England Journal of Medicine 361(17):1651-1661, Massachusetts Medical Society, United States (Oct. 2009).
Simonaro, C.M., "Lysosomes, Lysosomal Storage Diseases, and Inflammation," Journal of Inborn Errors of Metabolism & Screening 4:1-8, Latin American Society of Inborn Errors of Metabolism and Newborn Screening, Uruguay (2016).
Son, S.M., et al., "Leucine Signals to mTORC1 Via Its Metabolite Acetyl-Coenzyme A," Cell Metabolism 29(1):192-201.e7, Cell Press, United States (Jan. 2019).
Stein, L.R., and Imai, S-I., "The Dynamic Regulation of NAD Metabolism in Mitochondria," Trends in Endocrinology and Metabolism 23(9):420-428, Elsevier Science Pub. Co, United States (Sep. 2012).
Stiasny-Kolster, K., et al., "Diagnostic value of the REM sleep behavior disorder screening questionnaire in Parkinson's disease," Sleep Medicine 16(1):186-189, Elsevier, Netherlands (Jan. 2015).
Stiasny-Kolster, K., et al., "The REM Sleep Behavior Disorder Screening Questionnaire—A New Diagnostic Instrument," Movement Disorders 22(16):2386-2393, Wiley, United States (Dec. 2007).
Strupp, M., et al., "Effects of Acetyl-dl-leucine in Patients with Cerebellar Ataxia: A Case Series," Journal of Neurology, 260(10):2556-2561, Springer-Verlag, Germany (2013).
Te Vruchte, D., et al., "Relative Acidic Compartment Volume as a Lysosomal Storage Disorder-associated Biomarker," The Journal of Clinical Investigation 124(3):1320-1328, American Society for Clinical Investigation, United States (Mar. 2014).
The Definition of "Disease Prevention", accessed from Free Dictionary Web, Retrieved from Internet URL: https://web.archive.org/web/20150910204016/https://medical-dictionary.thefreedictionary.com/Prevention+(medical), 2 Pages, (Sep. 2018).
Tighilet, B., et al., "Comparative Analysis of Pharmacological Treatments With N-acetyl-dl-leucine (Tanganil) and Its Two Isomers (N-acetyl-L-leucine and N-acetyl-D-leucine) on Vestibular Compensation: Behavioral Investigation in the Cat," European Journal of Pharmacology 769:342-349, Elsevier Science, Netherlands (Dec. 2015).

(56) References Cited

OTHER PUBLICATIONS

Timmins, G.S., "Deuterated Drugs: Where Are We Now?" Expert Opinion on Therapeutic Patents 24(10):1067-1075, Taylor & Francis, United Kingdom (Oct. 2014).
Tuttolomondo, A., et al., "Studies of Selective TNF Inhibitors in the Treatment of Brain Injury from Stroke and Trauma: a Review of the Evidence to Date," Drug Design, Development and Therapy 8:2221-2238, Dove Press Limited, New Zealand (Nov. 2014).
Upson, D.A., and Hruby, V.J., "A General Method for the Preparation of Alpha-labeled Amino Acids," The Journal of Organic Chemistry 42(13):2329-2330, American Chemical Society, United States (Jun. 1977).
Van Tonder, E.C., et al., "Preparation and Physicochemical Characterization of 5 Niclosamide Solvates and 1 Hemisolvate," AAPS PharmSciTech 5(1):E12, pp. 1-10, Springer, United States (Feb. 2004).
Vibert, N., and Vidal, P.P., "In Vitro Effects of Acetyl-dl-leucine(Tanganil) on Central Vestibular Neurons and Vestibulo-ocular Networks of the Guinea-pig," The European Journal of Neuroscience 13(4):735-748, Wiley-Blackwell, France (Feb. 2001).
Williams, I.M., et al., "Improved Neuroprotection Using Miglustat, Curcumin and Ibuprofen as a Triple Combination Therapy in Niemann-pick Disease Type C1 Mice," Neurobiology of Disease 67:9-17, Academic Press, United States (Jul. 2014).
Written Opinion of International Preliminary Examining Authority of International Application No. PCT/IB2021/050236, European Patent Office, Netherlands, mailed on Dec. 17, 2021, 7 pages.
Xu, H., and Ren, D., "Lysosomal Physiology," Annual Review of Physiology 77:57-80, Annual Reviews, United States (2015).
Yamauchi, N., and Endoh, S., "Improved Isotopic Deuterium Labeling at the Diastereotopic Methyl Group of Leucine: a Synthetic Route to (4S)- and (4R)-[5-$^2H_1$] Leucine," Bioscience, Biotechnology, and Biochemistry 70(1):276-278, Oxford University Press, United Kingdom (Jan. 2006).
Yanagisawa, H., et al., "L-leucine and SPNS1 Coordinately Ameliorate Dysfunction of Autophagy in Mouse and Human Niemann-Pick type C disease," Scientific Reports 7(1):15944, Nature Publishing Group, United Kingdom (Nov. 2017).
Yanjanin, N.M., et al., "Linear Clinical Progression, Independent of Age of Onset, in Niemann-pick Disease, Type C," American Journal of Medical Genetics Neuropsychiatric Genetics 153B(1):132-140, Wiley-Blackwell, United States (Jan. 2010).
Yu, W., et al., "Neurodegeneration in Heterozygous Niemann-Pick type Cl (NPC1) Mouse: Implication of Heterozygous NPC1 Mutations Being a Risk for Tauopathy," The Journal of Biological Chemistry 280(29): 27296-27302, American Society for Biochemistry and Molecular Biology, United States (Jul. 2005).
Yuan, S.S., and Ajami, A.M., "Trideuteromethyl Labeled Leucine and Valine," Hua Xue—Chemistry 49(4):257-260, Zhonggguo Huaxuehui, Taiwan (Dec. 1991).
Yudkoff, M., "Brain Metabolism of Branched-chain Amino Acids," Glia 21(1):92-98, Wiley-Liss, United States (Sep. 1997).
European Medicines Agency, "Zavesca," European Public Assessment Report—Product Information, accessed at ec.europa.eu/health/documents/community-register/2010/2010060278532/anx_78532_en.pdf, accessed on Apr. 16, 2025, 25 pages (Jun. 2010).
Zech, M., et al., "Niemann-Pick C Disease Gene Mutations and Age-Related Neurodegenerative Disorders," PLoS One 8(12):e82879, Public Library of Science, United States (Dec. 2013).
Zwergal A., et al., "Sequential [(18)F]FDG µPET Whole-brain Imaging of Central Vestibular Compensation: A Model of Deafferentation-induced Brain Plasticity," Brain Structure and Function 221(1):159-170, Springer-Verlag, Germany (2016).
Armstrong, C., "AAN/AHS Update Recommendations for Migraine Prevention in Adults," American Family Physician 87(8):584-585, American Academy of General Practice, United States (2013).
Bartleson, J.D. and Cutrer F. M., "Migraine Update Diagnosis and Treatment," Minnesota Medicine 93(5):36-41, Minnesota Medical Assn, United States (May 2010).
Buchfuhrer, M.J., "Strategies for the Treatment of Restless Legs Syndrome," Neurotherapeutics 9(4):776-790, Springer, United States (Oct. 2012).
Bose, P. and Goadsby, P.J., "The Migraine Postdrome," Current Opinion in Neurology 29(3):299-301, Lippincott Williams & Wilkins, United Kingdom (Jun. 2016).
Buzzi, M.G., et al., "Prodromes and the Early Phase of the Migraine Attack: Therapeutic Relevance," Functional neurology 20(4):179-183, CIC Edizioni Internazionali, Italy (Oct.-Dec. 2005).
Colman, I., et al., "Parenteral Dexamethasonefor Acute Severe Migraine Headache: Meta-analysis of Randomised Controlled Trials for Preventing Recurrence," BMJ (Clinical research ed.) 336(7657):1359-1361, British Medical Association, United Kingdom (Jun. 2008).
Derry, S., et al., "Diclofenac with or without an Antiemetic for Acute Migraine Headaches in Adults," The Cochrane Database of Systematic Reviews 2013(4):CD008783, Wiley, United Kingdom (Apr. 2013), 43 Pages.
Ferber-Viart, C., et al., "Effects of Acetyl-dl-leucine in Vestibular Patients: A Clinical Study Following Neurotomy and Labyrinthectomy," Audiology and Neuro-otology 14(1):17-25, Karger, Switzerland (2009).
Gilmore, B. and Michael, M., "Treatment of Acute Migraine Headache," American family physician, 83(3):271-280, American Academy of General Practice, United States (2011).
Headache Classification Subcommittee of the International Headache Society, *The International Classification of Headache Disorders: 2nd edition*, Cephalalgia 24(Suppl 1):150 pages, Sage, United Kingdom (2004).
Kelman, L., "The Postdrome of the Acute Migraine Attack," Cephalalgia: An International Journal of Headache 26(2):214-220, Blackwell Publishing Ltd, United Kingdom (Feb. 2006).
Kirthi, V., et al., "Aspirin with or without an Antiemetic For Acute Migraine Headaches in Adults," The Cochrane database of systematic reviews 2013(4):CD008041, Wiley, United Kingdom (2010).
Lempert, T., et al., "Vestibular Migraine: Diagnostic Criteria," Journal of Vestibular Research: Equilibrium & Orientation 22(4):167-172, SAGE Publications, United States (2012).
Ory, D.S., et al., "Intrathecal 2-hydroxypropyl-β-cyclodextrin Decreases Neurological Disease Progression in Niemann-Pick Disease, Type C1: a Non-randomised, Open-label, Phase 1-2 Trial," Lancet 390(10104):1758-1768, Elsevier, United Kingdom (Oct. 2017).
Rabbie, R., et al., "Ibuprofen with or without an Antiemetic for Acute Migraine Headaches in Adults," The Cochrane database of systematic reviews 6:(10):CD008039, Wiley, United Kingdom (Oct. 2010).
Rae-Grant., [edited by] Lynn, J.D., et al., "The 5-Minute Neurology Consult, 2nd Edition," Lippincott Williams & Wilkins, Philadelphia, p. 26 (2004).
Rossi, P., et al., "Prodromes and Predictors of Migraine Attack," Functional Neurology 20(4):185-191, CIC Edizioni Internazionali, Italy (Oct.-Dec. 2005).
Wheeler, S., and Sillence, D.J., "Niemann-Pick type C Disease: Cellular Pathology and Pharmacotherapy," Journal of Neurochemistry 153(6):674-692, Wiley on behalf of the International Society for Neurochemistry, United Kingdom (Jun. 2020).
Tepper, S.J. and Tepper D.E., "Breaking the Cycle of Medication Overuse Headache," Cleveland Clinic Journal of Medicine, 77(4):236-242, Cleveland Clinic Educational Foundation, United States (2010).
Domitrz, I., et al., "Changes in Serum Amino Acids in Migraine Patients without and with Aura and their Possible Usefulness in the Study of Migraine Pathogenesis," CNS and Neurological Disorders Drug Targets, 14(3):345-349, Bentham Science Publishers, United Arab Emirates (2015).
Salzman, B., et al., "Gait and Balance Disorders in Older Adults," American Family Physician 82(1):61-68, American Academy of General Practice, United States (Jul. 2010).
Jahn, K., et al., "Dizziness and Unstable Gait in Old Age: Etiology, Diagnosis and Treatment," German Medical Journal International 112(23):387-393, German Doctors Publishing House, Germany (Jun. 2015).
Abe, et al., "Medium-Chain Triglycerides in Combination with Leucine and Vitamin D Increase Muscle Strength and Function in

(56) References Cited

OTHER PUBLICATIONS

Frail Elderly Adults in a Randomized Controlled Trial" The Journal of Nutrition 146(5):1017-1026, Elsevier, United States (May 2016).
Iwasaki, S., and Yamasobaet, T., "Dizziness and Imbalance in the Elderly: Age-related Decline in the Vestibular System," Aging and Disease 6(1):38-47, JKL International, United States (Feb. 2014).
Davis, O.B., et al., "NPC1-mTORC1 Signaling Couples Cholesterol Sensing to Organelle Homeostasis and Is a Targetable Pathway in Niemann-Pick Type C," Developmental Cell 56(3):260-276, Cell Press, United States (Feb. 2021).
Churchill, G.C., et al., "Acetylation Turns Leucine Into a Drug by Membrane Transporter Switching," Scientific Reports 11(1):15812, pp. 1-10, Nature Publishing Group, United Kingdom (Aug. 2021).
Auer, I.A., et al., "Paired Helical Filament Tau (PHFtau) in Niemann-pick Type C Disease is Similar to PHFtau in Alzheimer's Disease," Acta Neuropathologica 90(6):547-551, Springer Verlag, Germany (1995).
Nixon, R.A., "Niemann-Pick Type C Disease and Alzheimer's Disease: The APP-endosome Connection Fattens Up," The American Journal of Pathology 164(3):757-761, Elsevier, United States (Mar. 2004).
Castellano, B.M., et al., "Lysosomal Cholesterol Activates Mtorc1 via an Slc38a9-niemann-pick C1 Signaling Complex," Science 355(6331):1306-1311, American Association for the Advancement of Science, United States (Mar. 2017).
English Translation of Decision of Refusal issued in related Japanese Application No. 2021-164793, dated Apr. 25, 2023, 3 pages.
English Translation of Notice of Reason for Refusal issued in related Japanese Application No. 2021-164793, dated Sep. 29, 2022, 4 pages.
English Translation of Notice of Final Rejection issued in related Korean Application No. KR 10-2022-7021012, dated Apr. 3, 2023, 4 pages.
Communication from the European Patent Office issued in related EP Application No. 19174007.5, mailed Nov. 26, 2019, 5 pages.
English Translation of The Second Office Action issued in related Chinese Application No. CN 201780059708.6, dated Dec. 15, 2021, 4 pages.
English Translation of The First Office Action issued in related Chinese Application No. CN 201780059708.6, dated Jul. 29, 2021, 5 pages.
English Translation of Search Report issued by the Registered Search Organization in related Japanese Application No. JP 2019-507819, dated Apr. 2, 2021, 14 pages.
English Translation of Written Opinion issued in related Japanese Application No. JP 2019-507819, dated Aug. 11, 2021, 5 pages.
English Translation of Notice of Reasons for Refusal issued in related Application No. JP 2019-507819, dated Apr. 27, 2021, 4 pages.
Lukas, J., et al., "Enzyme Enhancers for the Treatment of Fabry and Pompe Disease," Molecular Therapy 23(3):456-464, Cell Press, United States (Mar. 2015).
Reagan-Shaw, S., et al., "Dose translation from animal to human studies revisited," FASEB journal 22(3):659-661, Federation of American Societies for Experimental Biology, United States (Mar. 2008).
Bremova, T., "Niemann-pick Type C: Effects of a Therapy With Acetyl-dl-leucine and Vestibular Function," Disseration for Graduate School Systemic Neurosciences Der Ludwig-maximilians-universitat Munchen. Presented Orally to the Public on Sep. 19, 2016 (2016), 93 Pages.
English Translation of Japanese Office Action in Counterpart Application No. 2019-507811 dated Apr. 27, 2021, 4 pages.
English Translation of Search Report in Chinese Application No. 201780062740X, dated Aug. 14, 2021, 1 page.
Search Report in Russian Application No. 2019106493, dated Oct. 26, 2020 with English Translation.
Olesen, J., et al., "The International Classification of Headache Disorders, 3rd Edition (Beta Version)," Cephalalgia 33(9):629-808, Sage, United Kingdom (Jul. 2013).
English language Translation of Pertinent Portion of Office Action for Japanese Patent Application No. 2020-519196, dated Apr. 26, 2022, 5 pages.
Dos Santos, A.B., et al., "Treatment of Sleeping Disorders Should Be Considered in Clinical Management of Parkinson's Disease," Frontiers in Aging Neuroscience 6:273, Frontiers Research Foundation, Switzerland (Oct. 2014).
Murofushi, T., "Migraine Associated Vertigo," Equilibrium Research 70(3): 172-175, Japan Society for Equilibrium Research, Japan (2011).
Kurokawa, K., et al., "Migraine and Vertigo: Introduction to Migrainous Vertigo," Journal of Clinical and Experimental Medicine 255(7):757-761, Springer, Switzerland (2015).
Fernandez, M., et al., "Pharmacological agents for the prevention of vestibular migraine," The Cochrane Database of Systematic Reviews 2015(6):CD010600, Wiley, United Kingdom (Jun. 2015).
Velazquez-Perez, L., et al., "Lisuride Reduces Involuntary Periodic Leg Movements in Spinocerebellar Ataxia Type 2 Patients," Cerebellum (London, England) 11(4):1051-1056, Springer, United States (Dec. 2012).
Porter, V.R., et al., "Sleep, Cognition and Dementia," Current Psychiatry Reports 17(12):1-11, Current Science, United States (Oct. 2015).
Suzuki, K., et al., "Sleep Disturbances in Neurodegenerative Diseases," Nihon Naika Gakkai zasshi. The Journal of the Japanese Society of Internal Medicine 106(2):309-318, Nihon Naika Gakkai, Japan (Feb. 2017).
English Translation of Office Action for Japanese Patent Application No. 2020-521938, mailed on Apr. 1, 2022, 3 Pages.
Abe, S., et al., "Medium-Chain Triglycerides in Combination with Leucine and Vitamin D Benefit Cognition in Frail Elderly Adults: A Randomized Controlled Trial," Journal of Nutritional Science and Vitaminology 63(2):133-140, University of Tokyo Press, Japan (2017).
Dehay, B., et al., "Lysosomal Impairment in Parkinson's Disease," Movement Disorders 28(6):725-732, Wiley-Liss, United States (Jun. 2013).
Xu, J., et al., "Cholesterol Trafficking Is Required for mTOR Activation in Endothelial Cells," Proceedings of the National Academy of Sciences of the United States of America 107(10):4764-4769, National Academy of Sciences, United States (Mar. 2010).
Oldendorf, W.H., "Stereospecificity of Blood-brain Barrier Permeability to Amino Acids," The American Journal of Physiology 224(4):967-969, American Physiological Society, United States (Apr. 1973).
Shemesh, A., et al., "Suppression of mTORC1 Activation in Acid—Glucosidase-deficient Cells and Mice Is Ameliorated by Leucine Supplementation," American Journal of Physiology. Regulatory, Integrative and Comparative Physiology 307(10):R1251-R1259, American Physiological Society, United States (Nov. 2014).
Ropper, A.H. and Samuels, M.A., "Adam's and Victor's Principles of Neurology," 9th Edition, Chapter 10, McGraw Hill Education, New York (2009).
Brueggemann, A., et al., "Effects of Acetyl-DL-Leucine on Ataxia and Downbeat-Nystagmus in Six Patients With Ataxia Telangiectasia," Journal of Child Neurology 37(1):20-27, Sage, United States (Jan. 2022).
Haripriya, G.R., et al., "Incidence and Treatment Outcomes of Post Traumatic BPPV in Traumatic Brain Injury Patients," Indian J Otolaryngol Head Neck Surg 70(3):337-341, Springer, India (Apr. 2018).
Ananieva, E.A., et al., "Leucine Metabolism in T Cell Activation: mTOR Signaling and Beyond," Advances in Nutrition 7(4):798S-805S, American Society for Nutrition, United States (Jul. 2016).
Benard, P., et al., "Autoradiography in brain of Macaca fascicularis monkeys after injection of acetyl-DL-leucine [2-14C] (Tanganil), " Eur J Drug Metab Pharmacokinet 26(1-2):71-76, Springer Paris, France (Jan.-Jun. 2001).
Birnbaum, S.M., et al., "Specificity of amino acid acylases," J Biol Chem 194(1):455-470, Elsevier Inc., United States (Jan. 1952).
Bloch, K., and Rittenberg, D., "The metabolism of acetylamino acids," J Biol Chem 169(3):467-476, Elsevier Inc., United States (Aug. 1947).

(56) References Cited

OTHER PUBLICATIONS

Brandsch, M., et al., "The intestinal H+/peptide symporter PEPT1: structure-affinity relationships, " Eur J Pharm Sci 21(1):53-60, Elsevier, Netherlands (Jan. 2004).
Broer, S., and Fairweather, S.J., "Amino Acid Transport Across the Mammalian Intestine," Compr Physiol 9(1):343-373, John Wiley and Sons Inc., United States (Jan. 1, 2019).
Camenisch, G., et al., "Review of theoretical passive drug absorption models: historical background, recent developments and limitations," Pharm Acta Helv 71(5):309-327, Elsevier, Netherlands (Nov. 1996).
Cheng, Y., and Prusoff, W.H., "Relationship between the inhibition constant (K1) and the concentration of inhibitor which causes 50 per cent inhibition (I50) of an enzymatic reaction," Biochem Pharmacol 22(23):3099-3108, Elsevier Inc., United States (Dec. 1973).
Churchill, G.C., et al., "Unexpected differences in the pharmacokinetics of N-acetyl-DL-leucine enantiomers after oral dosing and their clinical relevance," PLoS One 15(2):e0229585, Public Library of Science, United States (Feb. 2020).
Del Amo, E.M., et al., "Pharmacokinetic role of L-type amino acid transporters LAT1 and LAT2," Eur J Pharm Sci 35(3):161-174, Elsevier, Netherlands (Oct. 2008).
Enerson, B.E., and Drewes, L.R., "Molecular features, regulation, and function of monocarboxylate transporters: implications for drug delivery," J Pharm Sci 92(8):1531-1544, John Wiley & Sons, United States (Aug. 2003).
Eriksson, T., et al., "Clinical pharmacology of thalidomide," Eur J Clin Pharmacol 57(5):365-376, Springer Verlag, Germany (Aug. 2001).
Fagan, T., "The Lactic Acid Shuttle—It May Change How We Image the Brian," Alzforum.org, Jul. 3, 2004, accessed at https://www.alzforum.org/news/research-news/lactic-acid-shuttle-it-may-change-how-we-image-brain, accessed on Jan. 30, 2024, 4 pages.
Fagerberg, L., et al., "Analysis of the human tissue-specific expression by genome-wide integration of transcriptomics and antibody-based proteomics," Mol Cell Proteomics 13(2):397-406, Elsevier BV, United States (Feb. 2014).
Feil, K., et al., "Effects of acetyl-DL-leucine on cerebellar ataxia (ALCAT trial): study protocol for a multicenter, multinational, randomized, double-blind, placebo-controlled, crossover phase III trial," BMC Neurol 17(1):7, BioMed Central Ltd., United Kingdom (Jan. 2017).
Fields, T., et al., "A master protocol to investigate a novel therapy acetyl-L-leucine for three ultra-rare neurodegenerative diseases: Niemann-Pick type C, the GM2 gangliosidoses, and ataxia telangiectasia," Trials 22(1):84, BioMed Central, United Kingdom (Jan. 2021).
Gleeson, M.P., et al., "Probing the links between in vitro potency, ADMET and physicochemical parameters," Nat Rev Drug Discov 10(3):197-208, Nature Publishing Group, United Kingdom (Mar. 2011).
Gregori-Puigjane, E., et al., "Identifying mechanism-of-action targets for drugs and probes," Proc Natl Acad Sci USA 109(28):11178-11183, National Academy of Sciences, United States (Jul. 2012).
Halestrap, A.P., and Wilson, M.C., "The monocarboxylate transporter family—role and regulation," IUBMB Life 64(2):109-119, Wiley-Blackwell, United States (Feb. 2012).
Hashimoto, T., et al., "Lactate sensitive transcription factor network in L6 cells: activation of MCT1 and mitochondrial biogenesis," FASEB J 21(10):2602-2612, John Wiley & Sons, United States (Aug. 2007).
Im, H.A., et al., "N-acetyl-L-tyrosine as a tyrosine source during total parenteral nutrition in adult rats," Pediatr Res 19(6):514-518, Lippincott Williams and Wilkins Ltd., United States (Jun. 1985).
International Search Report and Written Opinion for International Application No. PCT/IB2022/055513, European Patent Office, Netherlands, mailed on Sep. 20, 2022, 14 pages.
International Transporter Consortium, et al., "Membrane transporters in drug development," Nat Rev Drug Discov 9(3):215-236, Nature Publishing Group, United Kingdom (Mar. 2010).
Izyumov, D.S., et al., "'Wages of fear': transient threefold decrease in intracellular ATP level imposes apoptosis," Biochim Biophys Acta 1658(1-2):141-147, Elsevier, Netherlands (Jul. 2004).
Jha, M.K., et al., "Metabolic Connection of Inflammatory Pain: Pivotal Role of a Pyruvate Dehydrogenase Kinase-Pyruvate Dehydrogenase-Lactic Acid Axis, " J Neurosci 35(42):14353-14369, Society for Neuroscience, United States (Oct. 2015).
Kalogeropoulou, D., et al., "Leucine, when ingested with glucose, synergistically stimulates insulin secretion and lowers blood glucose," Metabolism 57(12):1747-1752, Elsevier, Netherlands (Dec. 2008).
Kanai, Y., et al., "Expression cloning and characterization of a transporter for large neutral amino acids activated by the heavy chain of 4F2 antigen (CD98)," J Biol Chem 273(37):23629-23632, Elsevier Inc., United States (Sep. 1998).
Kaya, E., et al., "Acetyl-leucine slows disease progression in lysosomal storage disorders," Brain Commun 3(1):fcaa148, Oxford University Press, United States (Dec. 2020).
Kaya, E., et al., "Beneficial Effects of Acetyl-DL-Leucine (ADLL) in a Mouse Model of Sandhoff Disease," J Clin Med 9(4):1050, MDPI AG, Switzerland (Apr. 2020).
Kennedy, B.E., et al., "Adaptations of energy metabolism associated with increased levels of mitochondrial cholesterol in Niemann-Pick type C1-deficient cells," J Biol Chem 289(23):16278-16289, Elsevier Inc., United States (Jun. 2014).
Keogh, J.P., "Membrane transporters in drug development," Adv Pharmacol 63:1-42, Academic Press Inc., United States (2012).
Koepsell, H. and Endou, H., "The SLC22 drug transporter family," Pflugers Arch 447(5):666-676, Springer Verlag, Germany (Feb. 2004).
Krehbiel, C.R., and Matthews, J.C., "Absorption of Amino Acids and Peptides" in Amino Acids in Animal Nutrition, D'Mello, J.P.F., ed., pp. 41-70, CABI Publishing, United Kingdom (2003).
Leeson, P.D., and Springthorpe, B., "The influence of drug-like concepts on decision-making in medicinal chemistry," Nat Rev Drug Discov 6(11):881-890, Nature Publishing Group, United Kingdom (Nov. 2007).
Lin, L., et al., "SLC transporters as therapeutic targets: emerging opportunities," Nat Rev Drug Discov 14(8):543-560, Nature Publishing Group, United Kingdom (Aug. 2015).
Lipinski, C.A., "Drug-like properties and the causes of poor solubility and poor permeability," J Pharmacol Toxicol Methods 44(1):235-249, Elsevier Inc., United States (Jul.-Aug. 2000).
Missner, A., and Pohl, P., "110 years of the Meyer-Overton rule: predicting membrane permeability of gases and other small compounds," Chemphyschem 10(9-10):1405-1414, Wiley-VCH Verlag, Germany (Jul. 2009).
Neuhauser, M., et al., "Utilization of N-acetyl-L-tyrosine and glycyl-L-tyrosine during long-term parenteral nutrition in the growing rat," Am J Clin Nutr 42(4):585-596, American Society for Nutrition, United States (Oct. 1985).
Neuhoff, S., et al., "pH-Dependent passive and active transport of acidic drugs across Caco-2 cell monolayers," Eur J Pharm Sci 25(2-3):211-220, Elsevier, Netherlands (Jun. 2005).
Newington, J.T., et al., "Reevaluating Metabolism in Alzheimer's Disease from the Perspective of the Astrocyte-Neuron Lactate Shuttle Model," J Neurodegener Dis 2013:234572, S. Karger AG, Switzerland (2013).
Nicklin, P., et al., "Bidirectional transport of amino acids regulates mTOR and autophagy," Cell 136(3):521-534, Cell Press, United States (Feb. 2009).
Nigam, S.K., et al., "The organic anion transporter (OAT) family: a systems biology perspective," Physiol Rev 95(1):83-123, American Psychlogical Society, United States (Jan. 2015).
Olah, J., et al., "Increased glucose metabolism and ATP level in brain tissue of Huntington's disease transgenic mice, " FEBS J 275(19):4740-4755, Wiley-Blackwell Publishing Ltd., United States (Oct. 2008).
Patet, C., et al., "Cerebral Lactate Metabolism After Traumatic Brain Injury," Curr Neurol Neurosci Rep 16(4):31, Current Medicine Group, United States (Apr. 2016).

(56) References Cited

OTHER PUBLICATIONS

Pochini, L., et al., "Membrane transporters for the special amino acid glutamine: structure/function relationships and relevance to human health," Front Chem 2:61, Frontiers Media S.A., Switerland (Aug. 2014).
Pubchem, "Cyclopentyl (2S)-2-(hexanoylamino)-4-methylpentatnoate," PubChem CID 143660433, accessed at https://pubchem.ncbi.nlm.nih.gov/compound/143660433, accessed on Jan. 30, 2024, 8 pages.
Puri, S., and Juvale, K., "Monocarboxylate transporter 1 and 4 inhibitors as potential therapeutics for treating solid tumours: A review with structure-activity relationship insights," Eur J Med Chem 199:112393, Elsevier Masson, France (Aug. 2020).
Rubio-Aliaga, I., and Daniel, H., "Peptide transporters and their roles in physiological processes and drug disposition," Xenobiotica 38(7-8):1022-1042, Informa Healthcare, United Kingdom (Jul. 2008).
Sala, N., et al., "Cerebral extracellular lactate increase is predominantly nonischemic in patients with severe traumatic brain injury," J Cereb Blood Flow Metab 33(11):1815-1822, SAGE Publications, United States (Nov. 2013).
Sawada, K., et al., "Recognition of L-amino acid ester compounds by rat peptide transporters PEPT1 and PEPT2," J Pharmacol Exp Ther 291(2):705-709, American Society for Pharmacology and Experimental Therapeutics, United States (Nov. 1999).
Scalise, M., et al., "The Human SLC7A5 (LAT1): The Intriguing Histidine/Large Neutral Amino Acid Transporter and Its Relevance to Human Health," Front Chem 6:243, Frontiers Media S.A., Switzerland (Jun. 2018).
Schoser, B., et al., "Treatment of restless legs syndrome with acetyl-DL-leucine—accidental findings and a small case series," Neurology 26(694):EPO2251, Lippincott Williams and Wilkins Ltd., United States (Mar. 2021).
Sheffner, A.L., et al., "Metabolic studies with acetylcysteine," Biochem Pharmacol 15(10):1523-1535, Elsevier Inc., United States (Oct. 1966).
Smith, Q.R., et al., "Kinetics of neutral amino acid transport across the blood-brain barrier," J Neurochem 49(5):1651-1658, Wiley-Blackwell Publishing Ltd., United Kingdom (Nov. 1987).
Soares-Da-Silva, P., and Serrao, M.P., "High- and low-affinity transport of L-leucine and L-DOPA by the hetero amino acid exchangers LAT1 and LAT2 in LLC-PK1 renal cells," Am J Physiol Renal Physiol 287(2):F252-F261, American Physiological Society, United States (Aug. 2004).
Strupp, M., et al., "Prophylactic treatment of migraine with and without aura with acetyl-DL-leucine: a case series," J Neurol 266(2):525-529, Springer Science + Business Media, Germany (Feb. 2019).
Sugano, K., et al., "Coexistence of passive and carrier-mediated processes in drug transport," Nat Rev Drug Discov 9(8):597-614, Nature Publishing Group, United Kingdom (Aug. 2010).
Sun, S., et al., "Lactic Acid: No Longer an Inert and End-Product of Glycolysis," Physiology (Bethesda) 32(6):453-463, American Physiological Society, United States (Nov. 2017).
Thompson, B.R., et al., "Pharmacokinetics of gemcitabine and its amino acid ester prodrug following intravenous and oral administrations in mice," Biochem Pharmacol 180:114127, Elsevier Inc., United States (Oct. 2020).
Van De Waterbeemd, H., et al., "Estimation of blood-brain barrier crossing of drugs using molecular size and shape, and H-bonding descriptors," J Drug Target 6(2):151-165, Informa Healthcare, United Kingdom (1998).
Vruchte, E., et al., "Effects of N-Acetyl-Leucine and its enantiomers in Niemann-Pick disease type C cells," BioRxiv.org, accessed at https://www.biorxiv.org/content/10.1101/82622v1, accessed on Jan. 30, 2024, 13 pages.
Walter, A., and Gutknecht, J., "Monocarboxylic acid permeation through lipid bilayer membranes," J Membr Biol 77(3):255-264, Springer New York, United States (1984).
Platt, F.M., et al., "Lysosomal storage diseases," Nature Reviews Disease Primers 4(1):27, pp. 1-25, Nature Publishing Group, United Kingdom (Oct. 2018).
Strupp, M., et al., "Episodic ataxia type 2," Neurotherapeutics 4(2):267-273, Elsevier, United States (Apr. 2007).
Las Heras, M., et al., "Understanding the phenotypic variability in Niemann-Pick disease type C (NPC): a need for precision medicine," NPJ Genome Medicine 8(1):21, Nature Publishing Group, United Kingdom (Aug. 2023).
Bremova-Ertl, T., et al., "Trial of N-Acetyl-l-Leucine in Niemann-Pick Disease Type C," New England Journal of Medicine 390(5):421-431, Massachusetts Medical Society, United States (Feb. 2024).
Fields, T., et al., "N-acetyl-L-leucine for Niemann-Pick type C: a multinational double-blind randomized placebo-controlled crossover study," Trials 24(1):361, BioMed Central, United Kingdom (May 2023).
Mengel, E., et al., "Clinical disease progression and biomarkers in Niemann-Pick disease type C: a prospective cohort study," Orphanet Journal of Rare Diseases 15(1):328, BioMed Central, United Kingdom (Nov. 2020).
Schmitz-Hubsch, T., "Scale for the assessment and rating of ataxia: development of a new clinical scale," Neurology 66(11):1717-1720, Lippincott Williams & Wilkins, United States (Jun. 2006).
U.S. Food and Drug Administration, AQNEURSA™ (levacetylleucine) for oral suspension Approval Label and Prescribing Information, IntraBio Ltd., revised Sep. 2024, 15 pages.
U.S. Food and Drug Administration, MIPLYFFA (arimoclomol) capsules, for oral use, Approval Label and Prescribing Information, Zevra Therapeutics, Inc., revised Oct. 2025, accessed at https://zevra.com/documents/MIPLYFFA-Prescribing-Information.pdf, accessed on Jan. 29, 2025, 16 pages.
Li, B., et al., "Identification and functional characterization of de novo variant in the SYNGAP1 gene causing intellectual disability," Frontiers in Genetics 14:1270175, pp. 1-7, Frontiers Research Foundation, Switzerland (Oct. 2023).
International Search Report and Written Opinion for International Application No. PCT/US2025/015918, Commissioner for Patents, United States, mailed on Apr. 2, 2025, 16 pages.
Sodhi, D.K., and Hagerman, R., "Fragile X Premutation: Medications, Therapy and Lifestyle Advice," Pharmacogenomics and Personalized Medicine 14:1689-1699, Dove Medical Press, New Zealand (Dec. 2021).
International Search Report and Written Opinion for International Application No. PCT/US2025/034430, European Patent Office, Netherlands, mailed on Jan. 30, 2026, 33 pages.
Palacios, N., et al., "Circulating plasma metabolites and cognitive function in a Puerto Rican cohort," Journal of Alzheimer's Disease, 76: 1267-80, IOS Press, Netherlands (May 2020).
Colaco, A., et al., "Mechanistic convergence and shared therapeutics agents in Niemann-Pick disease," Journal of Inherited Metabolic Disease, 43:574-85, Wiley, United States (Jan. 2020).
Sindelar, M., et al., "Untargeted metabolite profiling of cerebrospinal fluid uncovers biomarkers for severity of late infantile neuronal ceroid lipofuscinosis (CLN2, Batten disease)," Scientific Reports, 8:15229, Nature Published Group, United Kingdom (Oct. 2018).
Amador, M., et al., "Targeted versus untarged omics—the CAFSA story, " Journal of Inherited Metabolic Disease, 41:447-56, Wiley, United States (Feb. 2018).
Kalla, R., et al., "Update on the pharmacotherapy of cerebellar and central vestibular disorders," Journal of Neurology, 263:S24-29, Science+Business Media, United States (2016).
Williams, G., "A searchable cross-platform gene expression database reveals connections between drug treatments and disease," Genomics, 13:23, Elsevier, Netherlands (2012).
Bremova, T., et al., "Acetyl-dl-leucine in Niemann-Pick type C," Neurology, 85:1368-75, Wolters Kluwer, United States (2015).
Huhtiniemi, T., et al., "Structure-based design of pseudopeptidic inhibitors for SIRT1 and SIRT2," Journal of Medicinal Chemistry, 54, 6456-68, American Chemical Society, United States (2011).
Saberi-Karimian, M., et al., "The Effect of N-Acetyl-DL-Leucine on Neurological Symptoms in a Patient with Ataxia-Telangiectasia: a Case Study," Cerebellum 22(1):96-101, Springer, United States (Feb. 2023).

(56) References Cited

OTHER PUBLICATIONS

Pedroso, J.L., et al., "Acute cerebellar ataxia: differential diagnosis and clinical approach," Arquivos de Neuro-Psiquiatria 77(3):184-193, Brazilian Academy of Neurology, Brazil (Mar. 2019).
Tomimitsu H., and Mizusawa H., "[Episodic ataxia type 2]," Clinical Calcium 11(11):1456-1459, Abstract only, Iyaku (Medicine & Drug) Journal Co., Ltd, Japan (Nov. 2001).

* cited by examiner

| Property | | L-leucine | N-acetyl-L-leucine | Drug-like |
|---|---|---|---|---|
| Mass (Da) | | 131 | 173 | < 500 |
| Log P | | 1.59 | 0.49 | < 5 |
| Log D | | 1.59 | -2.54 | 0.5-3.5 |
| Solubility (mg/mL) | pH 7 | 9 | 428 | 16 |
| | pH 2 | 65 | 4 | 16 |
| Polar surface area | | 63 | 66 | < 70 |
| H bond donor | | 2 | 2 | < 5 |
| H bond acceptor | | 3 | 3 | < 10 |

pKa

N-acetyl-D,L-[$^2H_{10}$]leucine

L-[$^2H_{10}$]leucine

BRANCHED-CHAIN AMINO ACID DERIVATIVES TO TREAT DISEASE

BACKGROUND OF THE INVENTION

Field of Invention

The present disclosure provides DL-, D-, and L-N-acyl branched-chain amino acid analogs, and pharmaceutically acceptable salts and solvates thereof, and DL-, D-, and L-N-acyl branched-chain amino acid alkyl ester analogs, and pharmaceutically acceptable salts and solvates thereof. The present disclosure also provides methods of treating or delaying the progression of a lysosomal storage disorder, methods of providing neuroprotection in a subject having a lysosomal storage disorder, methods of treating or delaying the progression of a neurodegenerative disease in a subject, treating or delaying the progression of a neurodegenerative disease associated with defects in lysosomal storage in a subject, treating or preventing a migraine in a subject, and the symptoms associated therewith, treating or preventing restless legs syndrome, and the symptoms associated therewith, treating or preventing vertigo, and the symptoms associated therewith, or improving mobility and/or cognitive function in a subject, comprising administering N-acyl branched-chain amino acid analogs, and pharmaceutically acceptable salts and solvates thereof, or N-acyl branched-chain amino acid alkyl ester analogs, and pharmaceutically acceptable salts and solvates thereof, to the subject.

Background

Neurodegenerative diseases affect neurons, and the degenerative process can involve the progressive loss of neuronal structure, the progressive loss of neuronal function, or progressive neuron cell death. Neurodegenerative diseases are frequently associated with defects in lysosomal storage. This includes both the neurodegenerative lysosomal storage disorders and many common neurodegenerative diseases, such as Alzheimer's disease and Parkinson's disease, where links to lysosomal defects have been suggested. Therapeutic agents that are broadly neuroprotective would apply to neurodegenerative diseases generally, including those caused by an underlying lysosomal storage disorder and those caused by other processes.

Lysosomal storage disorders (LSDs) are a group of inherited metabolic diseases caused by defects in lysosomal homeostasis. LSDs encompass over 70 diseases, with a collective clinical frequency of 1:5000 live births. These diseases can be classified into two main groups: primary storage disorders resulting from a direct deficiency in degradation pathways (typically lysosomal enzyme deficiency disorders) and secondary storage disorders which are caused by malfunctioning downstream lysosomal proteins. Distinct LSDs that result from the inactivation of different lysosomal proteins often share similar pathologies. In most cases, multiple organs and tissues are involved. Region-specific neurodegeneration is featured in the majority of these diseases.

Migraines are characterized by recurrent moderate to severe headaches. Typically, the headaches affect one half of the head, are pulsating in nature, and last from 2 to 72 hours. Symptoms of migraine include nausea, vomiting, and sensitivity to light, sound or smell. The pain is often accentuated by physical activity. About 15% of the world's population is affected by migraines.

The changes that occur with ageing can lead to problems with a person's ability to move around. Mobility problems may include unsteadiness while walking, difficulty getting in and out of a chair, or falls. Muscle weakness, joint problems, pain, disease and neurological (brain and nervous system) difficulties—common conditions in older people—can all contribute to mobility problems. Sometimes several mild problems occur at one time and combine to seriously affect mobility.

In addition to potential mobility problems, all ageing humans will develop some degree of decline in cognitive capacity, symptoms often including forgetfulness, decreased ability to maintain focus, decreased problem-solving capacity and/or reduced spatial awareness. Symptoms can progress into more serious conditions, such as dementia and depression, or even Alzheimer's disease.

Many factors are believed to contribute to age-related cognitive decline, including oxidative stress and free radical damage, declining hormone levels (like estrogen, testosterone, DHEA and pregnenolone), inner arterial lining (endothelium) dysfunction, insulin resistance, excess body weight, suboptimal nutrition, loneliness, lack of social network and high stress, among other things.

Current therapeutic approaches to treat neurodegenerative diseases, LSDs, and migraines, and to improve mobility and/or cognitive function are limited. For example, some LSDs have been responsive to bone marrow transplantation or enzyme replacement therapy. Some benefit has also been reported in a clinical trial of substrate reduction therapy (SRT) using an inhibitor of glycosphingolipid (GSL) biosynthesis: the imino sugar drug, miglustat. Patterson, et al., *Rev Neurol* (*separata*) 43:8 (2006). Benefit has also been reported using acetyl-DL-leucine in case studies of patients with cerebellar ataxia (showing improved gait variability) and Niemann-Pick Type C (NPC) (showing improvement in ataxia). See Schniepp, R., et al., *Cerebellum & Ataxias* 3:8 (2016); Bremova, T., et al., *Neurology* 85:1368 (2015).

There exists a need for improved treatments of LSDs. There is also a need for improved treatments of neurodegenerative diseases, neurodegenerative diseases associated with defects in lysosomal storage, migraines, restless legs syndrome, and vertigo. There is also a need for improved treatments for improving mobility and/or cognitive function.

BRIEF SUMMARY OF THE INVENTION

In one aspect, the disclosure provides N-acyl branched-chain amino acid analogs, and the pharmaceutically acceptable salts and solvates thereof, and N-acyl branched-chain amino acid alkyl ester analogs, and the pharmaceutically acceptable salts and solvates thereof, represented by any one of Formulae I-III, below, collectively referred to herein as "Compounds of the Disclosure."

In another aspect, the disclosure provides a method of treating or delaying the progression of a LSD the method comprising administering to a subject in need thereof a therapeutically effective amount of a Compound of the Disclosure.

In another aspect, the disclosure provides a method of providing neuroprotection in a subject having a LSD, the method comprising administering to a subject in need thereof a therapeutically effective amount of a Compound of the Disclosure.

In another aspect, the disclosure provides a method of treating or delaying the progression of a neurodegenerative disease or a neurodegenerative disease associated with defects in lysosomal storage, the method comprising administering to a subject in need thereof a therapeutically effective amount of a Compound of the Disclosure.

In another aspect, the disclosure provides a method of treating or preventing a migraine, and the symptoms associated therewith, the method comprising administering to a subject in need thereof a therapeutically effective amount of a Compound of the Disclosure.

In another aspect, the disclosure provides a method of improving mobility and/or cognitive function, the method comprising administering to a subject in need thereof a therapeutically effective amount of a Compound of the Disclosure.

In another aspect, the disclosure provides a method of treating or preventing restless legs syndrome, and the symptoms associated therewith, the method comprising administering to a subject in need thereof a therapeutically effective amount of a Compound of the Disclosure.

In another aspect, the disclosure provides a method of treating or preventing vertigo, and the symptoms associated therewith, the method comprising administering to a subject in need thereof a therapeutically effective amount of a Compound of the Disclosure.

In another aspect, the present disclosure provides a pharmaceutical composition comprising a Compound of the Disclosure and an excipient and/or pharmaceutically acceptable carrier.

In another aspect, the present disclosure provides a pharmaceutical composition comprising a Compound of the Disclosure and an excipient and/or pharmaceutically acceptable carrier for use in treating or delaying the progression of a LSD in a subject.

In another aspect, the present disclosure provides a pharmaceutical composition comprising a Compound of the Disclosure and an excipient and/or pharmaceutically acceptable carrier for use in providing neuroprotection in a subject having a LSD.

In another aspect, the present disclosure provides a pharmaceutical composition comprising a Compound of the Disclosure and an excipient and/or pharmaceutically acceptable carrier for use in treating or delaying the progression of a neurodegenerative disease or a neurodegenerative disease associated with defects in lysosomal storage in a subject.

In another aspect, the present disclosure provides a pharmaceutical composition comprising a Compound of the Disclosure and an excipient and/or pharmaceutically acceptable carrier for use in treating or preventing a migraine, and the symptoms associated therewith, in a subject.

In another aspect, the present disclosure provides a pharmaceutical composition comprising a Compound of the Disclosure and an excipient and/or pharmaceutically acceptable carrier for use in improving mobility and/or cognitive function in a subject.

In another aspect, the disclosure provides a pharmaceutical composition comprising a Compound of the Disclosure and an excipient and/or pharmaceutically acceptable carrier for use in treating or preventing restless legs syndrome, and the symptoms associated therewith, in a subject.

In another aspect, the disclosure provides a pharmaceutical composition comprising a Compound of the Disclosure and an excipient and/or pharmaceutically acceptable carrier for use in treating or preventing vertigo, and the symptoms associated therewith, in a subject.

In another aspect, the present disclosure provides a Compound of the Disclosure for use in treating or delaying the progression of a LSD in a subject.

In another aspect, the present disclosure provides a Compound of the Disclosure for use in providing neuroprotection in a subject having a LSD.

In another aspect, the present disclosure provides a Compound of the Disclosure for use in treating or delaying the progression of a neurodegenerative disease or a neurodegenerative disease associated with defects in lysosomal storage in a subject.

In another aspect, the present disclosure provides a Compound of the Disclosure for use in treating or preventing a migraine, and the symptoms associated therewith, in a subject.

In another aspect, the present disclosure provides a Compound of the Disclosure for use in improving mobility and/or cognitive function in a subject.

In another aspect, the present disclosure provides a Compound of the Disclosure for use in treating or preventing restless legs syndrome, and the symptoms associated therewith, in a subject.

In another aspect, the present disclosure provides a Compound of the Disclosure for use in treating or preventing vertigo, and the symptoms associated therewith, in a subject.

In another aspect, the present disclosure provides a use of a Compound of the Disclosure for the manufacture of a medicament for treating or delaying the progression of a LSD in a subject.

In another aspect, the present disclosure provides a use of a Compound of the Disclosure for the manufacture of a medicament for providing neuroprotection in a subject having a LSD.

In another aspect, the present disclosure provides a use of a Compound of the Disclosure for the manufacture of a medicament for treating or delaying the progression of a neurodegenerative disease or a neurodegenerative disease associated with defects in lysosomal storage in a subject.

In another aspect, the present disclosure provides a use of a Compound of the Disclosure for the manufacture of a medicament for treating or preventing a migraine, and the symptoms associated therewith, in a subject.

In another aspect, the present disclosure provides a use of a Compound of the Disclosure for the manufacture of a medicament for improving mobility and/or cognitive function in a subject.

In another aspect, the present disclosure provides a use of a Compound of the Disclosure for the manufacture of a medicament for treating or preventing restless legs syndrome, and the symptoms associated therewith, in a subject.

In another aspect, the present disclosure provides a use of a Compound of the Disclosure for the manufacture of a medicament for treating or preventing vertigo, and the symptoms associated therewith, in a subject.

In another aspect, the present disclosure provides kits comprising a Compound of the Disclosure, and, optionally, a package insert containing directions for use in the treatment of a LSD, a neurodegenerative disease, or a neurodegenerative disease associated with defects in lysosomal storage in a subject.

In another aspect, the present disclosure provides kits comprising a Compound of the Disclosure, and, optionally, a package insert containing directions for use in treating or preventing a migraine, and the symptoms associated therewith, in a subject.

In another aspect, the present disclosure provides kits comprising a Compound of the Disclosure, and, optionally, a package insert containing directions for use in improving mobility and/or cognitive function in a subject.

In another aspect, the present disclosure provides kits comprising a Compound of the Disclosure, and, optionally, a package insert containing directions for use in treating or preventing restless legs syndrome, and the symptoms associated therewith, in a subject.

In another aspect, the present disclosure provides kits comprising a Compound of the Disclosure, and, optionally, a package insert containing directions for use in treating or preventing vertigo, and the symptoms associated therewith, in a subject.

In another embodiment, the disclosure provides procedures of personalized medicine for subjects having a LSD or a neurodegenerative disease, and encompasses the selection of treatment options with the highest likelihood of successful outcome for individual LSD or neurodegenerative subjects.

In another embodiment, the disclosure provides procedures of personalized medicine for subjects having a migraine, and the symptoms associated therewith, and encompasses the selection of treatment options with the highest likelihood of successful outcome for treating or preventing a migraine, and the symptoms associated therewith, in a subject.

In another embodiment, the disclosure provides procedures of personalized medicine for subjects in need of improving mobility and/or cognitive function, and encompasses the selection of treatment options with the highest likelihood of successful outcome for improving mobility and/or cognitive function in a subject.

In another aspect, the present disclosure provides methods of preparing Compounds of the Disclosure.

Additional embodiments and advantages of the disclosure will be set forth, in part, in the description that follows, and will flow from the description, or can be learned by practice of the disclosure. The embodiments and advantages of the disclosure will be realized and attained by means of the elements and combinations particularly pointed out in the appended claims.

It is to be understood that both the foregoing summary and the following detailed description are exemplary and explanatory only, and are not restrictive of the invention as claimed.

BRIEF DESCRIPTION OF THE DRAWINGS

FIG. 1(*b*) is a scheme illustrating the effect of N-acetylation on the $pK_a$ of the nitrogen atom.

FIG. 1(*c*) is an illustration showing speciation curves for the protonation states of L-leucine (top) and N-acetyl-L-leucine (bottom). The gross charge distribution of a molecule as a function of pH is also shown. The dominant species is indicated in several tissues relevant to drug absorption and distribution.

FIG. 1(*d*) is an illustration showing the charge at pH 7 with the $pK_a$ of the amino and carboxylic acid groups labelled.

FIG. 1(*e*) is an illustration showing mechanisms of absorption illustrated by crossing a membrane by passive diffusion or carrier-mediated uptake.

FIG. 2(*b*) is a line graph showing the concentration-response curves for the uptake of N-acetyl-L-leucine by PepT1. DMSO (0.5%) was the solvent control (SC) and the known inhibitor for the positive control (PC) was losartan (200 μM). Data were fit to either the Michaelis-Menten equation for uptake or the Hill equation for inhibition using the solvent control to define the top and the positive control inhibitor to define the bottom. Symbols represent the mean±SEM, n=3.

FIG. 2(*c*) is a line graph showing the concentration-inhibition curves for the inhibition of uptake of known substrate gabapentin (10 μM) for LAT1. DMSO (0.5%) was the solvent control (SC) and the known inhibitor for the positive control (PC) was JPH203 (10 μM). Data were fit to either the Michaelis-Menten equation for uptake or the Hill equation for inhibition using the solvent control to define the top and the positive control inhibitor to define the bottom. Symbols represent the mean±SEM, n=3.

FIG. 2(*d*) is a line graph showing the concentration-inhibition curves for the inhibition of uptake of known substrate dipeptide Gly-Sar (50 μM) for PepT1. DMSO (0.5%) was the solvent control (SC) and the known inhibitor for the positive control (PC) was losartan (200 μM). Data were fit to either the Michaelis-Menten equation for uptake or the Hill equation for inhibition using the solvent control to define the top and the positive control inhibitor to define the bottom. Symbols represent the mean±SEM, n=3.

FIG. 3(*b*) is a line graph showing the concentration-response curves for the uptake of N-acetyl-L-leucine by OAT3. DMSO (0.5%) was the solvent control (SC) and the known inhibitor diclofenac (100 μM) was the positive control (PC). Data were fit to either the Michalis-Menten equation for uptake or the Hill equation for inhibition using the solvent control to define the top and the positive control inhibitor to define the bottom. Symbols represent the mean±SEM, n=3.

FIG. 3(*c*) is a line graph showing the concentration-inhibition curves for the inhibition of uptake of known substrate chlorothiazide for OAT1 (3 μM). DMSO (0.5%) was the solvent control (SC) and the known inhibitor diclofenac (100 μM) was the positive control (PC). Data were fit to either the Michalis-Menten equation for uptake or the Hill equation for inhibition using the solvent control to define the top and the positive control inhibitor to define the bottom. Symbols represent the mean±SEM, n=3.

FIG. 3(*d*) is a line graph showing the concentration-inhibition curves for the inhibition of uptake of known substrate estrone-3-sulfate for OAT3 (2 μM). DMSO (0.5%) was the solvent control (SC) and the known inhibitor diclofenac (100 μM) was the positive control (PC). Data were fit to either the Michalis-Menten equation for uptake or the Hill equation for inhibition using the solvent control to define the top and the positive control inhibitor to define the bottom. Symbols represent the mean±SEM, n=3.

FIG. 4(*b*) is a line graph showing concentration-response curves for the uptake of N-acetyl-D-leucine for MCT1. DMSO (0.5%) was the solvent control (SC) and the known inhibitor phloretin (500 μM) was the positive control (PC).

FIG. 4(*c*) is a line graph showing concentration-inhibition curves for the inhibition of uptake of the known substrate 2-thiophene glyoxylate (500 μM) for MCT1. DMSO (0.5%) was the solvent control (SC) and the known inhibitor phloretin (500 μM) was the positive control (PC).

FIG. 4(*d*) is a line graph showing concentration-inhibition curves for the inhibition of uptake of the known substrate 2-thiophene glyoxylate (500 μM) for MCT1. DMSO (0.5%) was the solvent control (SC) and the known inhibitor phloretin (500 μM) was the positive control (PC).

FIG. 4(*e*) is an illustration showing the chemical structure of deuterated N-acetyl-DL-leucine incubated with cellular fraction S9 from liver to determine metabolism using liquid chromatography and mass spectrometry.

FIG. 4(*f*) is a line graph showing the time courses for loss of deuterated N-acetyl-DL-leucine and appearance of deuterated L-leucine for extracts derived from human livers.

FIG. 4(*g*) is a line graph showing time courses for loss of deuterated N-acetyl-D,L-leucine and appearance of deuterated L-leucine for extracts derived from mouse livers.

FIG. 4(*h*) is a line graph showing concentration versus initial velocities relationship for metabolism, which yielded $K_m$ values of 216 and 69 μM and $V_{max}$ values of 6.8 and 2.6 μmol/min/mg for human and mouse, respectively. Data were fit to the Michalis-Menten equation for transporter uptake and metabolism or the Hill equation for transporter inhibition using the solvent control to define the top and the positive control inhibitor to define the bottom. Symbols represent the mean±SEM, n=3.

DETAILED DESCRIPTION OF THE INVENTION

Figures 1A, 1B:
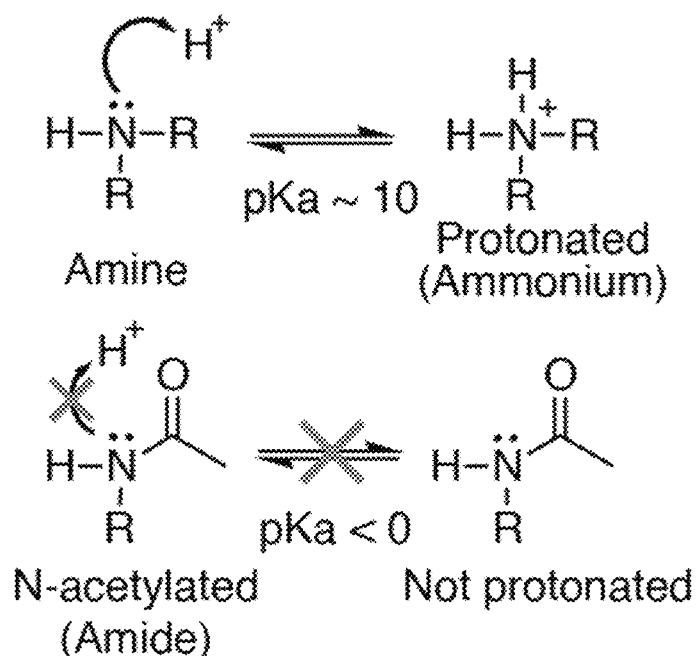
FIG. 1(*a*) is a table of physiochemical drug-like properties comparing the properties of L-leucine and N-acetyl-L-leucine relating to oral bioavailability.
Figure 1C:
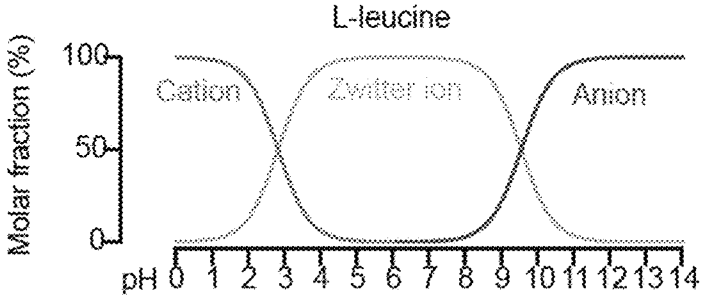
Figure 1C:
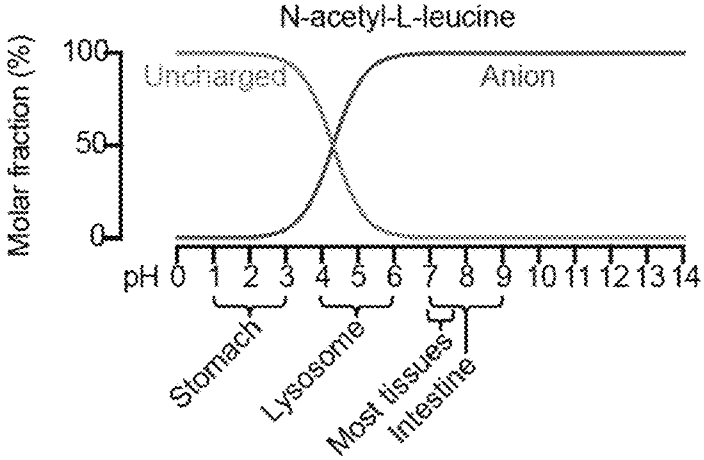
Figure 1D:
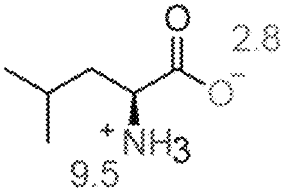
Figure 1D:
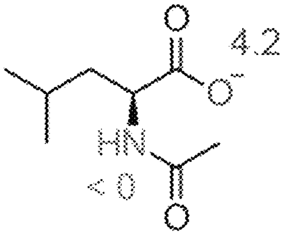
Figure 1E:
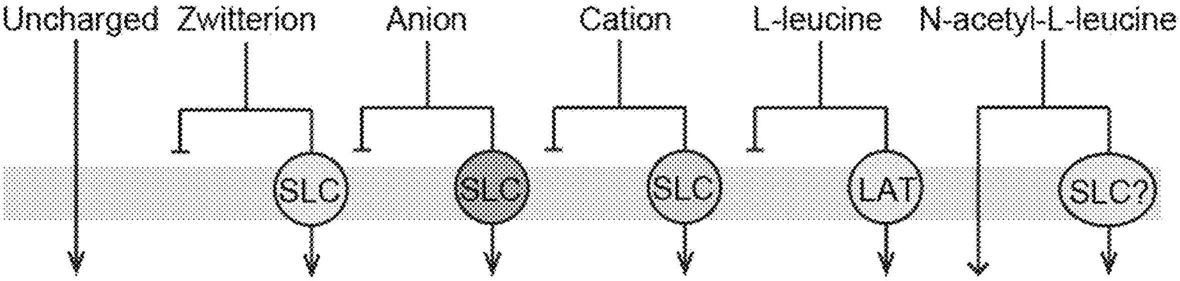
Figure 2A:
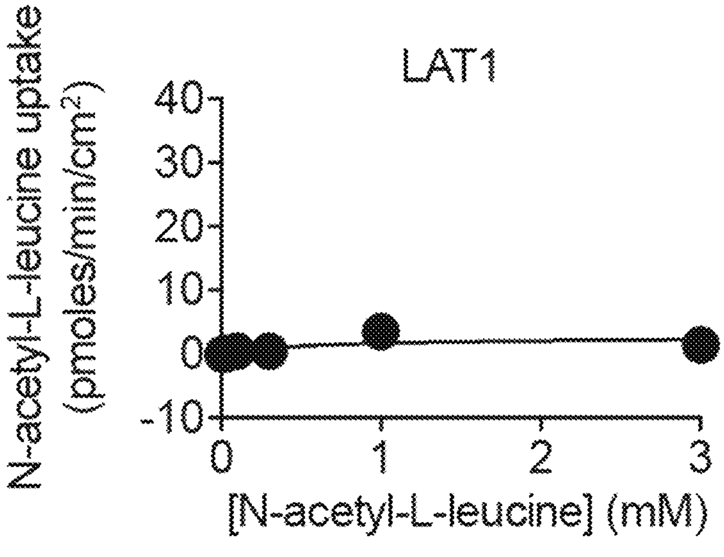
FIG. 2(*a*) is a line graph showing the concentration-response curves for the uptake of N-acetyl-L-leucine by LAT1. DMSO (0.5%) was the solvent control (SC) and the known inhibitor for the positive control (PC) was JPH203 (10 μM). Data were fit to either the Michaelis-Menten equation for uptake or the Hill equation for inhibition using the solvent control to define the top and the positive control inhibitor to define the bottom. Symbols represent the mean±SEM, n=3.
Figure 2B:
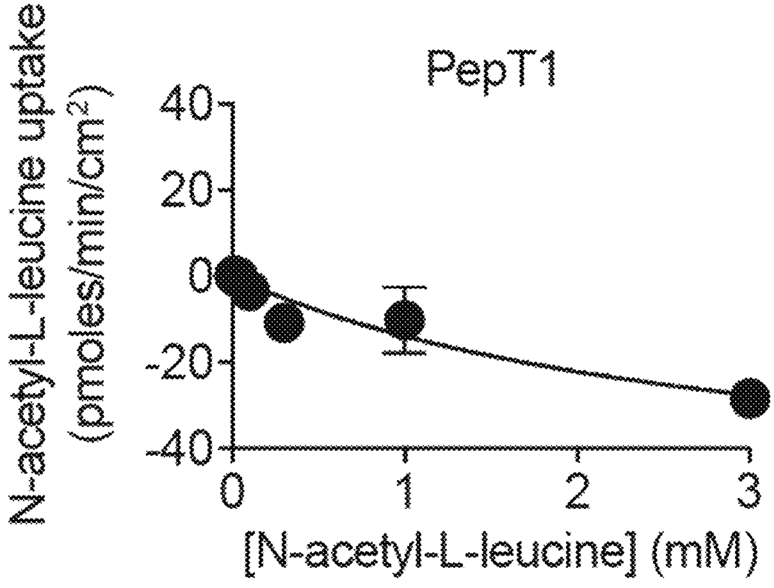
Figure 2C:
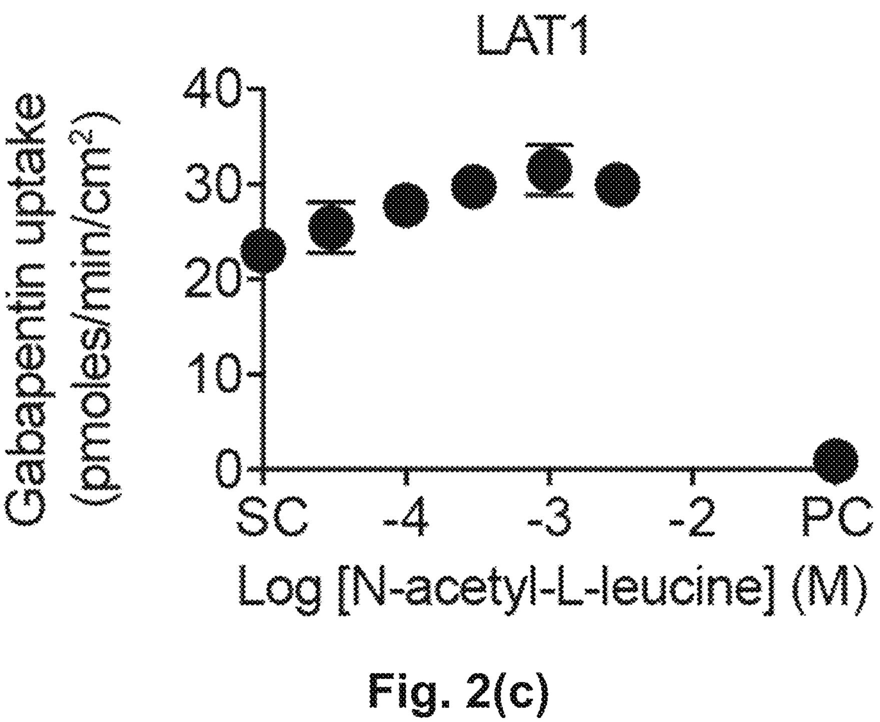
Figure 2D:
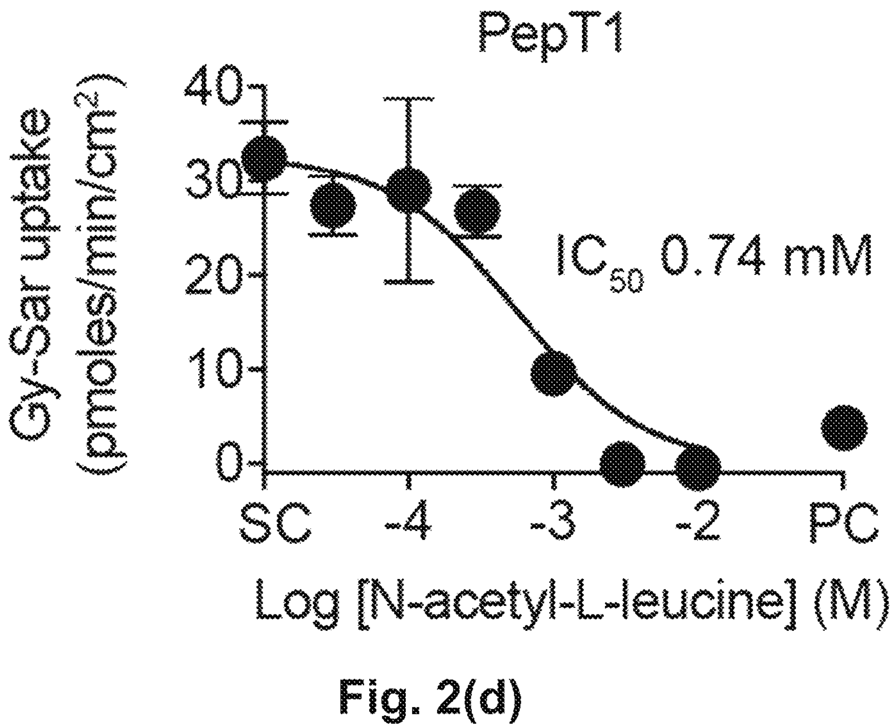
Figure 3A:
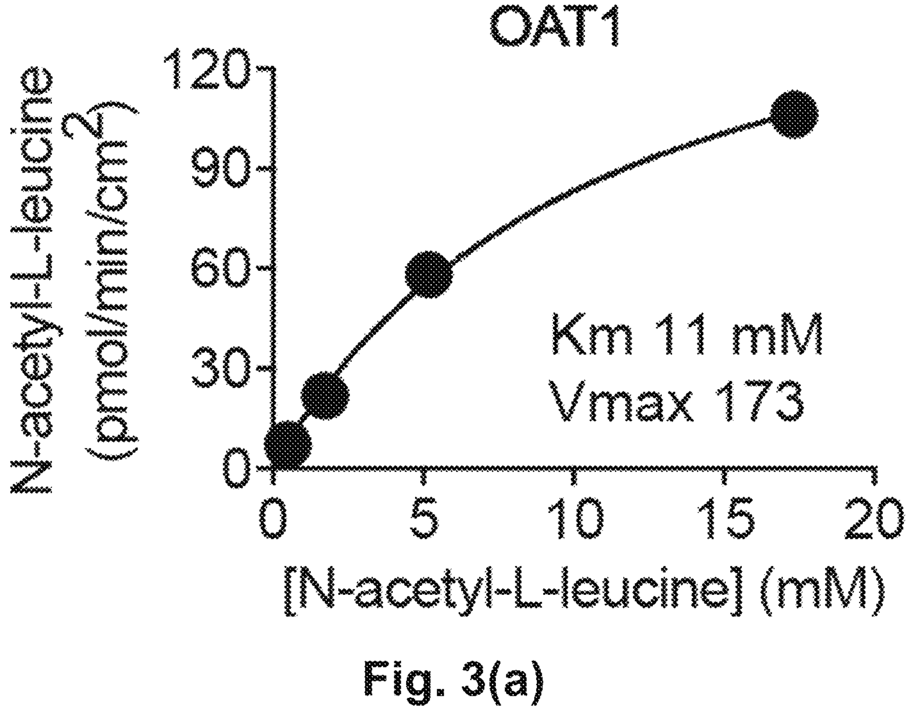
FIG. 3(*a*) is a line graph showing the concentration-response curves for the uptake of N-acetyl-L-leucine by OAT1. DMSO (0.5%) was the solvent control (SC) and the known inhibitor diclofenac (100 μM) was the positive control (PC). Data were fit to either the Michalis-Menten equation for uptake or the Hill equation for inhibition using the solvent control to define the top and the positive control inhibitor to define the bottom. Symbols represent the mean±SEM, n=3.
Figure 3B:
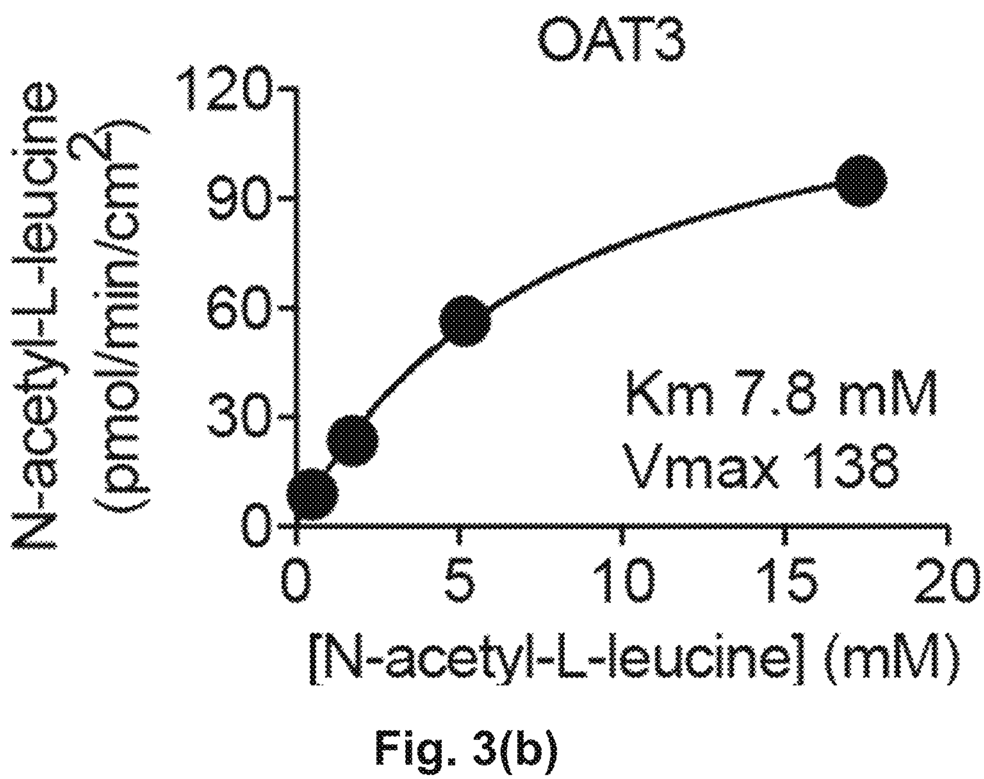
Figure 3C:
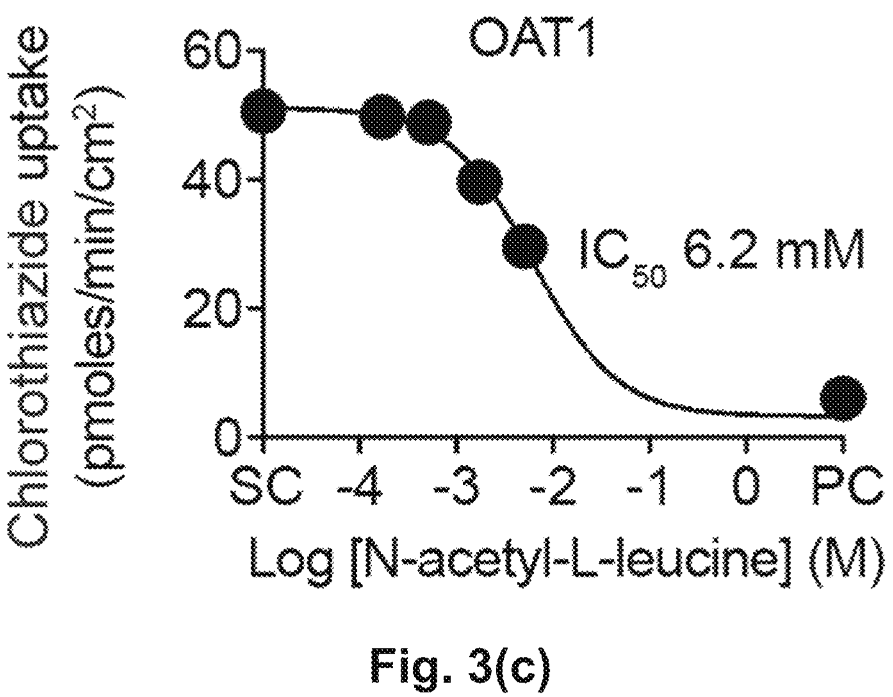
Figure 3D:
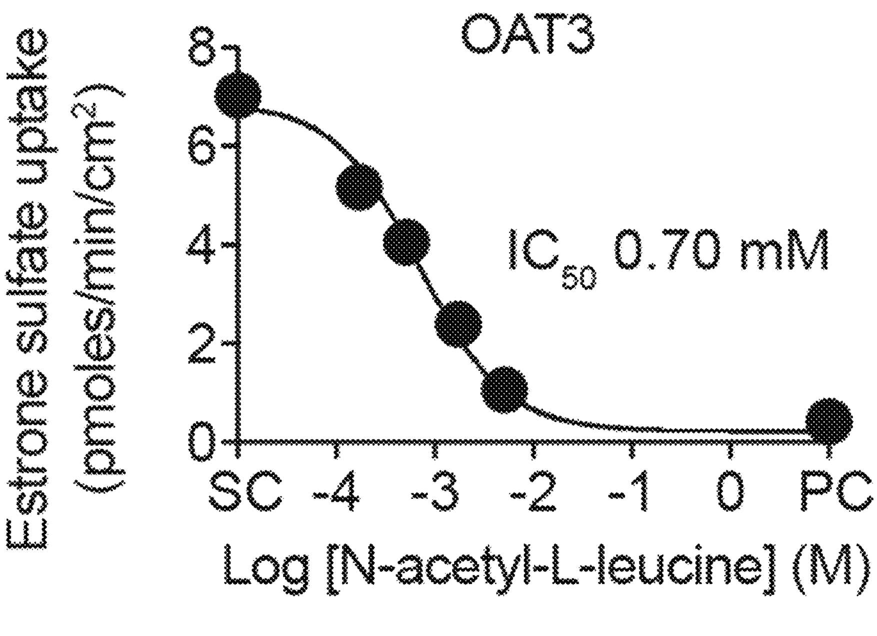
Figure 4A:
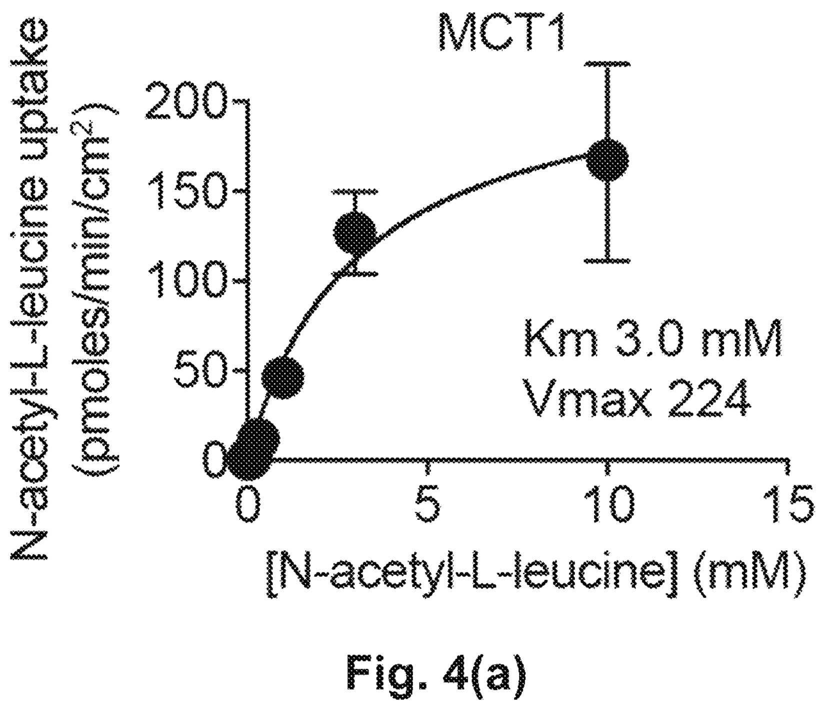
FIG. 4(*a*) is a line graph showing concentration-response curves for the uptake of N-acetyl-L-leucine for the monocarboxylate transporter (MCT1). DMSO (0.5%) was the solvent control (SC) and the known inhibitor phloretin (500 μM) was the positive control (PC).
Figure 4B:
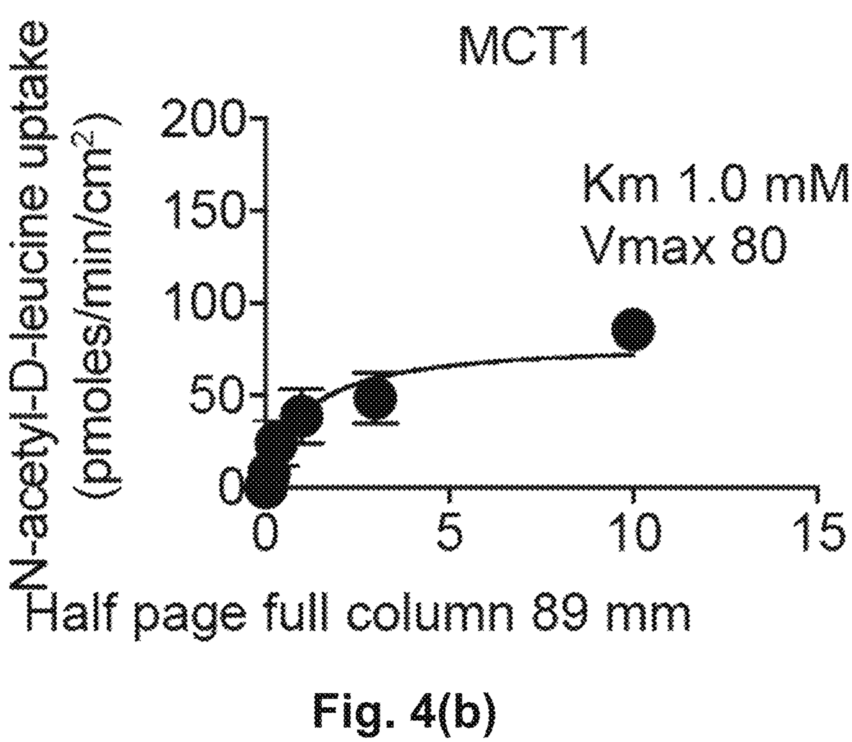
Figure 4C:
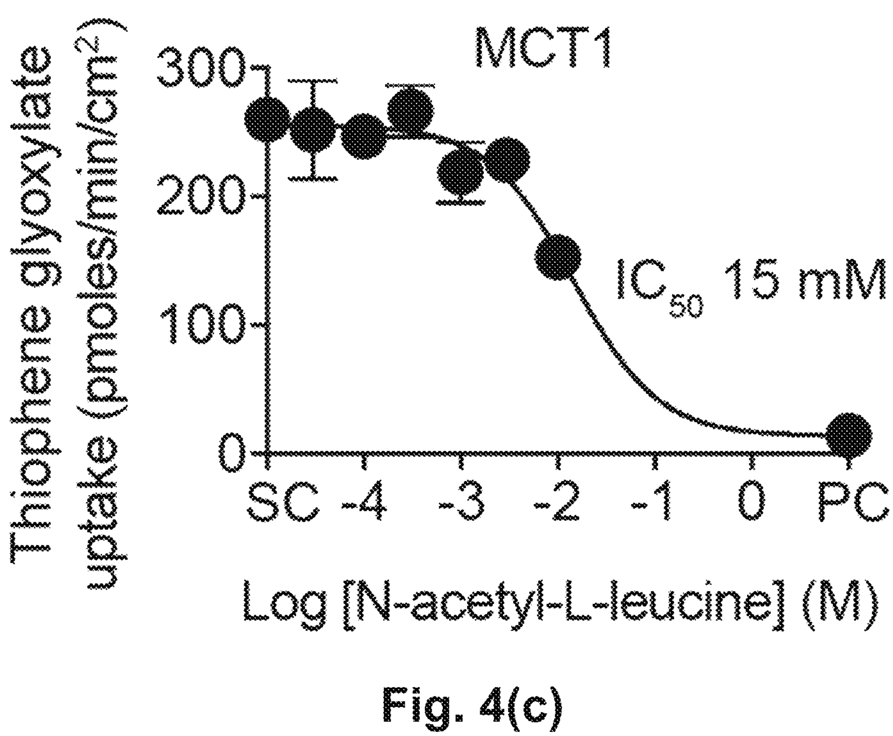
Figure 4D:
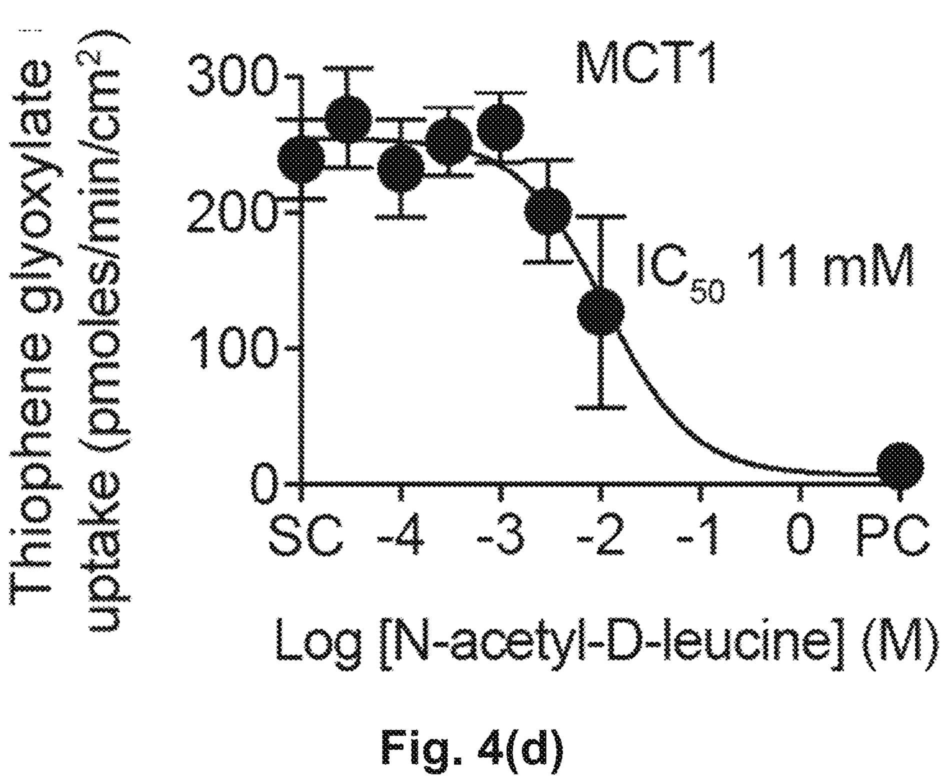
Figure 4E:
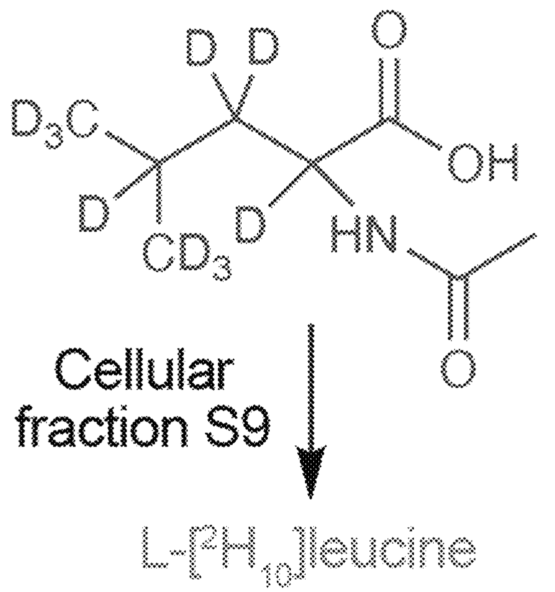
Figure 4F:
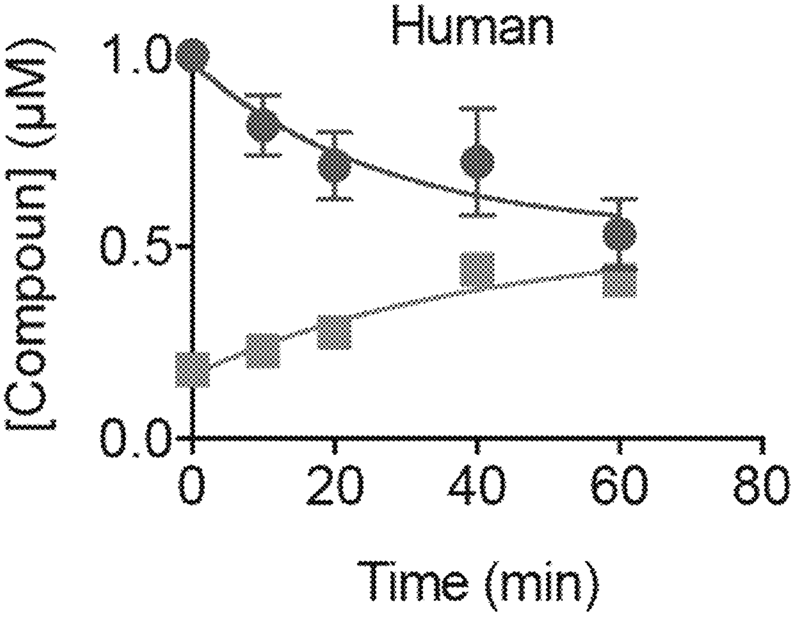
Figure 4G:
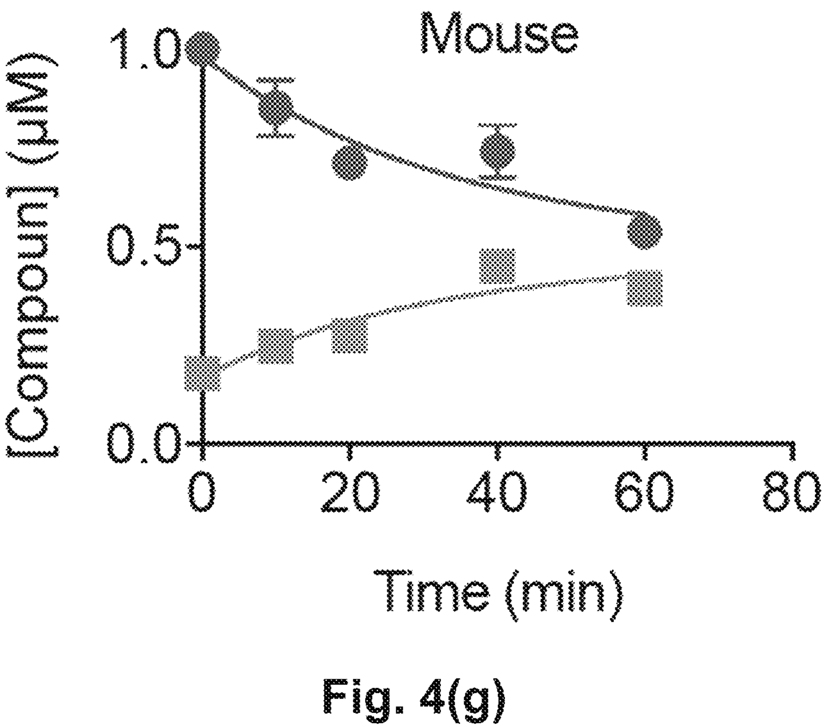
Figure 4H:
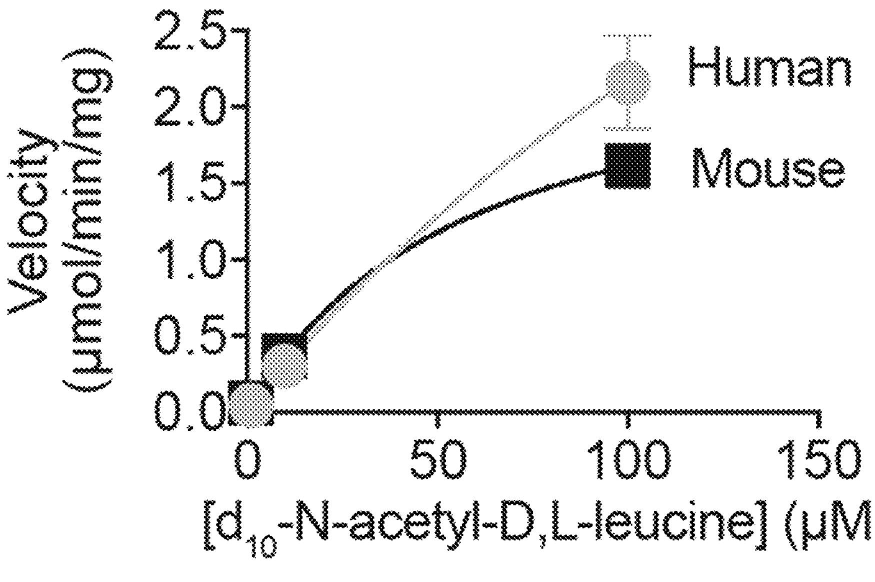

Compounds of the Disclosure are prodrugs that are metabolized to release branched-chain amino acids, e.g., leucine, isoleucine, or valine. Without wishing to be bound by any particular theory, Compounds of the Disclosure are taken up and distributed by anionic transports, primarily monocarboxylate transporter 1 (MCT1). These compounds are subsequently trapped in cells and metabolized, e.g., deacylated, to release the branched-chain amino acid. The increased intracellular concentration of the branched-chain amino acid activates mTORC1 (mechanistic target of rapamycin complex 1) and other cellular processes.

Compounds of the Disclosure can be used to treat or delay the progression of a disease, disorder, or condition in a subject, e.g., treat a LSD, provide neuroprotection in a subject having a LSD, treat or delay the progression of a neurodegenerative disease, treat or delay the progression a neurodegenerative disease associated with defects in lysosomal storage in a subject, treat or prevent a migraine, and the symptoms associated therewith, in a subject, treat or prevent restless legs syndrome, and the symptoms associated therewith, in a subject, treat or prevent vertigo, and the symptoms associated therewith, in a subject, or for improving mobility and/or cognitive function in a subject.

In one embodiment, Compounds of the Disclosure are compounds having Formula I:

I

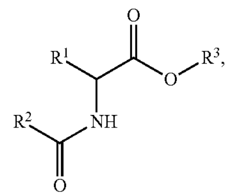

or a pharmaceutically acceptable salt or solvate thereof, wherein:

$R^1$ is selected from the group consisting of:

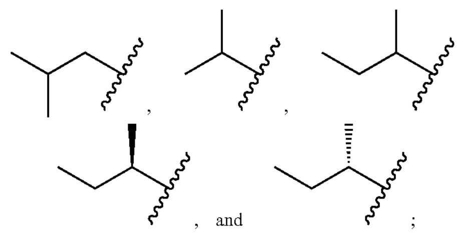

$R^2$ is selected from the group consisting of $C_2$-$C_6$ alkyl and $C_3$-$C_6$ cycloalkyl; and $R^3$ is selected from the group consisting of hydrogen, $C_1$-$C_6$ alkyl, and $C_3$-$C_6$ cycloalkyl.

In another embodiment, Compounds of the Disclosure are optically inactive compounds having Formula I, or a pharmaceutically acceptable salt or solvate thereof, i.e., the compound is racemic.

In another embodiment, Compounds of the Disclosure are optically active compounds having Formula I, or a pharmaceutically acceptable salt or solvate thereof.

In another embodiment, Compounds of the Disclosure are compounds having Formula II:

II

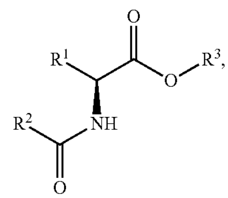

or a pharmaceutically acceptable salt or solvate thereof, wherein $R^1$, $R^2$, and $R^3$ are as defined in connection with Formula I.

In another embodiment, Compounds of the Disclosure are compounds having Formula III:

III

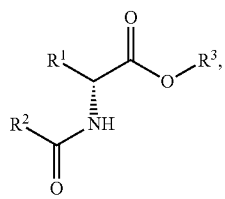

or a pharmaceutically acceptable salt or solvate thereof, wherein $R^1$, $R^2$, and $R^3$ are as defined in connection with Formula I.

In another embodiment, Compounds of the Disclosure are compounds having any one of Formulae I-III, or a pharmaceutically acceptable salt or solvate thereof, having an enantiomeric excess (ee) of about 50% or more. In another embodiment, the ee is about 55% or more, about 60% or more, about 65% or more, about 70% or more, about 75% or more, about 80% or more, about 85% or more, about 90% or more, about 95% or more, about 98% or more, or about 99% or more. In another embodiment, the ee is about 100%.

In another embodiment, Compounds of the Disclosure are compounds having any one of Formulae I-III, or a pharmaceutically acceptable salt or solvate thereof, wherein $R^1$ is:

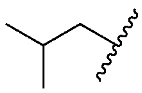

In another embodiment, Compounds of the Disclosure are compounds having any one of Formulae I-III, or a pharmaceutically acceptable salt or solvate thereof, wherein $R^1$ is:

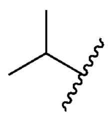

In another embodiment, Compounds of the Disclosure are compounds having any one of Formulae I-III, or a pharmaceutically acceptable salt or solvate thereof, wherein $R^1$ is:

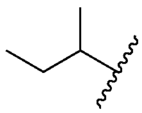

In another embodiment, Compounds of the Disclosure are compounds having any one of Formulae I-III, or a pharmaceutically acceptable salt or solvate thereof, wherein $R^1$ is:

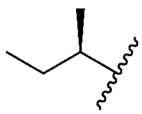

In another embodiment, Compounds of the Disclosure are compounds having any one of Formulae I-III, or a pharmaceutically acceptable salt or solvate thereof, wherein $R^1$ is:

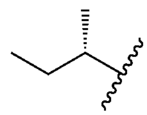

In another embodiment, Compounds of the Disclosure are compounds having any one of Formulae I-III, or a pharmaceutically acceptable salt or solvate thereof, wherein $R^2$ is selected from the group consisting of ethyl, propyl, iso-propyl, butyl, iso-butyl, sec-butyl, and tert-butyl.

In another embodiment, Compounds of the Disclosure are compounds having any one of Formulae I-III, or a pharmaceutically acceptable salt or solvate thereof, wherein $R^2$ is selected from the group consisting of cyclopropyl, cyclobutyl, cyclopentyl, and cyclohexyl.

In another embodiment, Compounds of the Disclosure are compounds having any one of Formulae I-III, or a pharmaceutically acceptable salt or solvate thereof, wherein $R^3$ is selected from the group consisting of methyl, ethyl, propyl, iso-propyl, butyl, iso-butyl, sec-butyl, and tert-butyl.

In another embodiment, Compounds of the Disclosure are compounds having any one of Formulae I-III, or a pharmaceutically acceptable salt or solvate thereof, wherein $R^3$ is selected from the group consisting of cyclopropyl, cyclobutyl, cyclopentyl, and cyclohexyl.

In another embodiment, Compounds of the Disclosure are compounds having any one of Formulae I-III, or a pharmaceutically acceptable salt or solvate thereof, wherein $R^3$ is hydrogen.

In another embodiment, Compounds of the Disclosure are compounds of Formula I, or a pharmaceutically acceptable salt or solvate thereof, wherein $R^1$, $R^2$, and $R^3$ are as defined in Table 1.

TABLE 1

| Cpd. No. | $R^1$ | $R^2$ | $R^3$ |
|---|---|---|---|
| 1 | 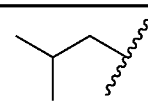 | ethyl | hydrogen |
| 2 | 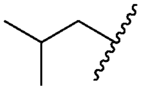 [SMILES: *CC(C)C] | propyl | hydrogen |
| 3 | 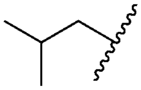 [SMILES: *CC(C)C] | iso-propyl | hydrogen |
| 4 | 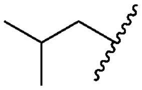 [SMILES: *CC(C)C] | cyclopropyl | hydrogen |
| 5 | 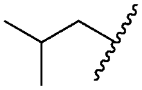 [SMILES: *CC(C)C] | cyclobutyl | hydrogen |
| 6 | 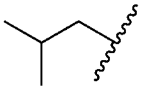 [SMILES: *CC(C)C] | ethyl | methyl |
| 7 | 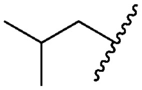 [SMILES: *CC(C)C] | propyl | methyl |

TABLE 1-continued

| Cpd. No. | $R^1$ | $R^2$ | $R^3$ |
|---|---|---|---|
| 8 | 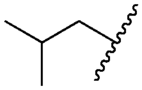 [SMILES: *CC(C)C] | iso-propyl | methyl |
| 9 | 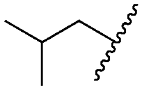 [SMILES: *CC(C)C] | cyclopropyl | methyl |
| 10 | 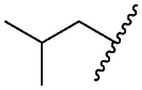 [SMILES: *CC(C)C] | cyclobutyl | methyl |
| 11 | 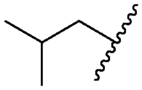 [SMILES: *CC(C)C] | ethyl | ethyl |
| 12 | 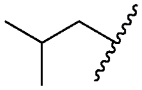 [SMILES: *CC(C)C] | propyl | ethyl |
| 13 | 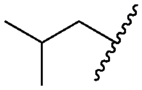 [SMILES: *CC(C)C] | iso-propyl | ethyl |
| 14 | 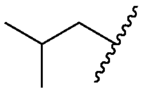 [SMILES: *CC(C)C] | cyclopropyl | ethyl |
| 15 | 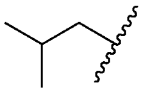 [SMILES: *CC(C)C] | cyclobutyl | ethyl |
| 16 | 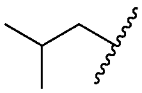 [SMILES: *CC(C)C] | ethyl | propyl |
| 17 | 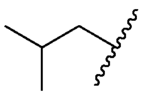 [SMILES: *CC(C)C] | propyl | propyl |
| 18 | 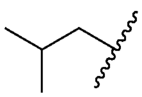 [SMILES: *CC(C)C] | iso-propyl | propyl |
| 19 | 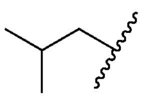 | cyclopropyl | propyl |
| 20 | 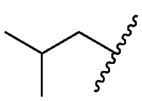 [SMILES: *CC(C)C] | cyclobutyl | propyl |
| 21 | 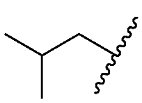 [SMILES: *CC(C)C] | ethyl | iso-propyl |
| 22 | 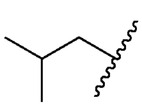 [SMILES: *CC(C)C] | propyl | iso-propyl |

TABLE 1-continued

| Cpd. No. | $R^1$ | $R^2$ | $R^3$ |
|---|---|---|---|
| 23 | 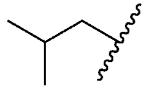 [SMILES: *CC(C)C] | iso-propyl | iso-propyl |
| 24 | 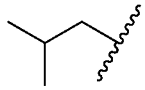 [SMILES: *CC(C)C] | cyclopropyl | iso-propyl |
| 25 | 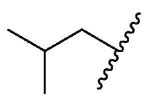 [SMILES: *CC(C)C] | cyclobutyl | iso-propyl |
| 26 | 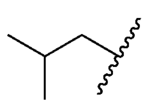 [SMILES: *CC(C)C] | ethyl | tert-butyl |
| 27 | 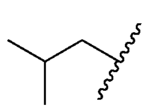 [SMILES: *CC(C)C] | propyl | tert-butyl |
| 28 | 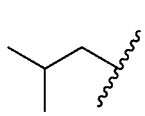 [SMILES: *CC(C)C] | iso-propyl | tert-butyl |
| 29 | 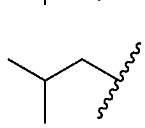 | cyclopropyl | tert-butyl |
| 30 | 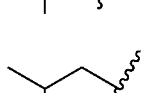 | cyclobutyl | tert-butyl |
| 31 | 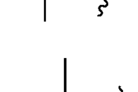 | ethyl | hydrogen |
| 32 | 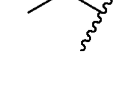 | propyl | hydrogen |
| 33 | 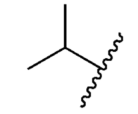 [SMILES: *C(C)C] | iso-propyl | hydrogen |
| 34 | 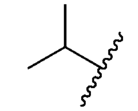 [SMILES: *C(C)C] | cyclopropyl | hydrogen |
| 35 | 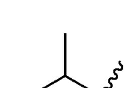 | cyclobutyl | hydrogen |

TABLE 1-continued

| Cpd. No. | $R^1$ | $R^2$ | $R^3$ |
|---|---|---|---|
| 36 | 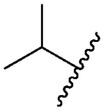 | ethyl | methyl |
| 37 | 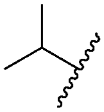 [SMILES: *C(C)C] | propyl | methyl |
| 38 | 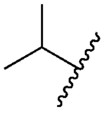 | iso-propyl | methyl |
| 39 | 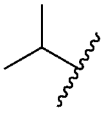 | cyclopropyl | methyl |
| 40 | 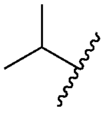 [SMILES: *C(C)C] | cyclobutyl | methyl |
| 41 | 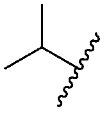 [SMILES: *C(C)C] | ethyl | ethyl |
| 42 | 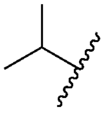 | propyl | ethyl |
| 43 | 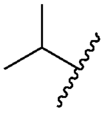 | iso-propyl | ethyl |
| 44 | 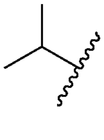 [SMILES: *C(C)C] | cyclopropyl | ethyl |
| 45 | 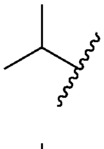 | cyclobutyl | ethyl |
| 46 | 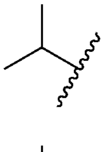 | ethyl | propyl |
| 47 | 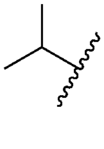 | propyl | propyl |

TABLE 1-continued

| Cpd. No. | $R^1$ | $R^2$ | $R^3$ |
|---|---|---|---|
| 48 | 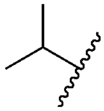 [SMILES: *C(C)C] | iso-propyl | propyl |
| 49 | 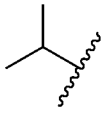 | cyclopropyl | propyl |
| 50 | 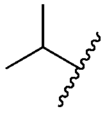 [SMILES: *C(C)C] | cyclobutyl | propyl |
| 51 | 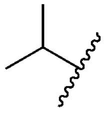 [SMILES: *C(C)C] | ethyl | iso-propyl |
| 52 | 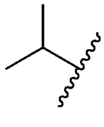 [SMILES: *C(C)C] | propyl | iso-propyl |
| 53 | 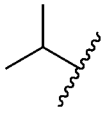 [SMILES: *C(C)C] | iso-propyl | iso-propyl |
| 54 | 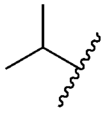 [SMILES: *C(C)C] | cyclopropyl | iso-propyl |
| 55 | 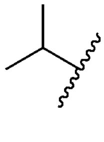 [SMILES: *C(C)C] | cyclobutyl | iso-propyl |
| 56 | 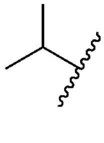 [SMILES: *C(C)C] | ethyl | tert-butyl |
| 57 | 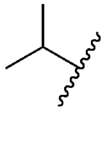 [SMILES: *C(C)C] | propyl | tert-butyl |
| 58 | 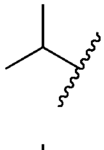 | iso-propyl | tert-butyl |
| 59 | 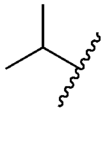  | cyclopropyl | tert-butyl |

TABLE 1-continued

| Cpd. No. | $R^1$ | $R^2$ | $R^3$ |
| --- | --- | --- | --- |
| 60 | 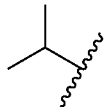 [SMILES: *C(C)C] | cyclobutyl | tert-butyl |
| 61 | 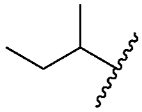 [SMILES: *C(C)CC] | ethyl | hydrogen |
| 62 | 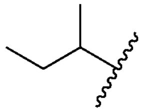 [SMILES: *C(C)CC] | propyl | hydrogen |
| 63 | 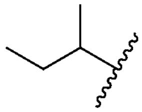 [SMILES: *C(C)CC] | iso-propyl | hydrogen |
| 64 | 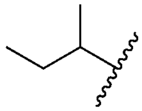 [SMILES: *C(C)CC] | cyclopropyl | hydrogen |
| 65 | 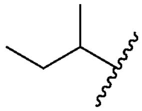 [SMILES: *C(C)CC] | cyclobutyl | hydrogen |
| 66 | 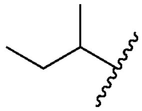 [SMILES: *C(C)CC] | ethyl | methyl |
| 67 | 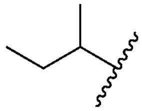 [SMILES: *C(C)CC] | propyl | methyl |
| 68 | 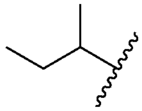 [SMILES: *C(C)CC] | iso-propyl | methyl |
| 69 | 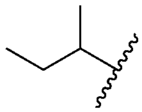 [SMILES: *C(C)CC] | cyclopropyl | methyl |
| 70 | 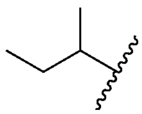 [SMILES: *C(C)CC] | cyclobutyl | methyl |
| 71 | 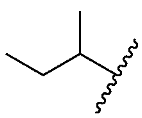 [SMILES: *C(C)CC] | ethyl | ethyl |

TABLE 1-continued

| Cpd. No. | $R^1$ | $R^2$ | $R^3$ |
| --- | --- | --- | --- |
| 72 | 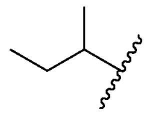 [SMILES: *C(C)CC] | propyl | ethyl |
| 73 | 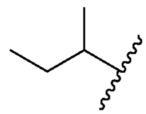 [SMILES: *C(C)CC] | iso-propyl | ethyl |
| 74 | 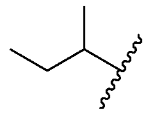 [SMILES: *C(C)CC] | cyclopropyl | ethyl |
| 75 | 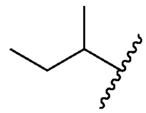 [SMILES: *C(C)CC] | cyclobutyl | ethyl |
| 76 | 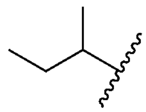 [SMILES: *C(C)CC] | ethyl | propyl |
| 77 | 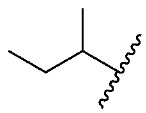 [SMILES: *C(C)CC] | propyl | propyl |
| 78 | 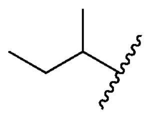 [SMILES: *C(C)CC] | iso-propyl | propyl |
| 79 | 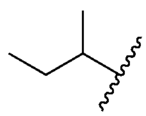 [SMILES: *C(C)CC] | cyclopropyl | propyl |
| 80 | 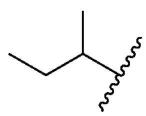 [SMILES: *C(C)CC] | cyclobutyl | propyl |
| 81 | 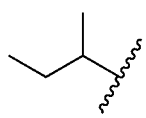 [SMILES: *C(C)CC] | ethyl | iso-propyl |
| 82 | 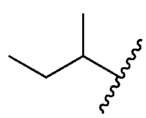 [SMILES: *C(C)CC] | propyl | iso-propyl |
| 83 | 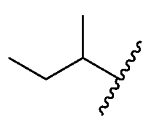 [SMILES: *C(C)CC] | iso-propyl | iso-propyl |

TABLE 1-continued

| Cpd. No. | $R^1$ | $R^2$ | $R^3$ |
|---|---|---|---|
| 84 | 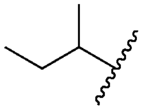 [SMILES: *C(C)CC] | cyclopropyl | iso-propyl |
| 85 | 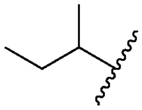 [SMILES: *C(C)CC] | cyclobutyl | iso-propyl |
| 86 | 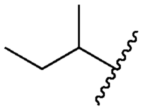 [SMILES: *C(C)CC] | ethyl | tert-butyl |
| 87 | 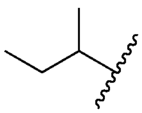 [SMILES: *C(C)CC] | propyl | tert-butyl |
| 88 | 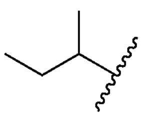 [SMILES: *C(C)CC] | iso-propyl | tert-butyl |
| 89 | 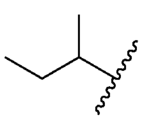 [SMILES: *C(C)CC] | cyclopropyl | tert-butyl |
| 90 | 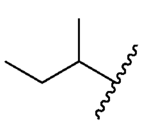 [SMILES: *C(C)CC] | cyclobutyl | tert-butyl |
| 91 | 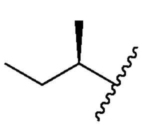 [SMILES: *[C@H](C)CC] | ethyl | hydrogen |
| 92 | 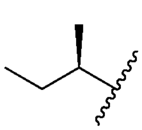 [SMILES: *[C@H](C)CC] | propyl | hydrogen |
| 93 | 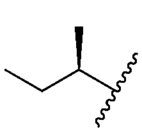 [SMILES: *[C@H](C)CC] | iso-propyl | hydrogen |
| 94 | 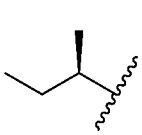 [SMILES: *[C@H](C)CC] | cyclopropyl | hydrogen |
| 95 | 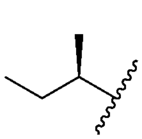 [SMILES: *[C@H](C)CC] | cyclobutyl | hydrogen |
| 96 | 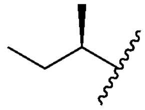 [SMILES: *[C@H](C)CC] | ethyl | methyl |
| 97 | 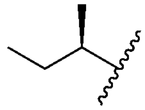 [SMILES: *[C@H](C)CC] | propyl | methyl |
| 98 | 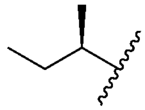 [SMILES: *[C@H](C)CC] | iso-propyl | methyl |
| 99 | 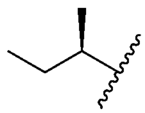 [SMILES: *[C@H](C)CC] | cyclopropyl | methyl |
| 100 | 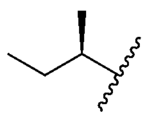 [SMILES: *[C@H](C)CC] | cyclobutyl | methyl |
| 101 | 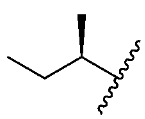 [SMILES: *[C@H](C)CC] | ethyl | ethyl |
| 102 | 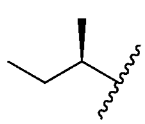 [SMILES: *[C@H](C)CC] | propyl | ethyl |
| 103 | 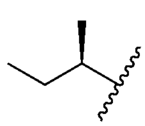 [SMILES: *[C@H](C)CC] | iso-propyl | ethyl |
| 104 | 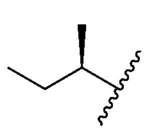 [SMILES: *[C@H](C)CC] | cyclopropyl | ethyl |
| 105 | 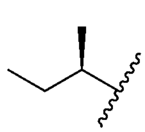 [SMILES: *[C@H](C)CC] | cyclobutyl | ethyl |
| 106 | 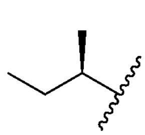 [SMILES: *[C@H](C)CC] | ethyl | propyl |
| 107 | 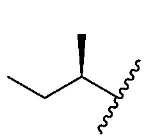 [SMILES: *[C@H](C)CC] | propyl | propyl |

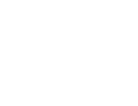

TABLE 1-continued

| Cpd. No. | $R^1$ | $R^2$ | $R^3$ |
|---|---|---|---|
| 108 | 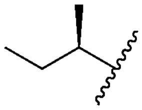 [SMILES: *[C@H](C)CC] | iso-propyl | propyl |
| 109 | 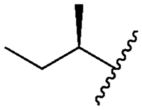 [SMILES: *[C@H](C)CC] | cyclopropyl | propyl |
| 110 | 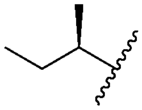 [SMILES: *[C@H](C)CC] | cyclobutyl | propyl |
| 111 | 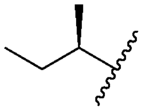 [SMILES: *[C@H](C)CC] | ethyl | iso-propyl |
| 112 | 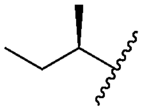 [SMILES: *[C@H](C)CC] | propyl | iso-propyl |
| 113 | 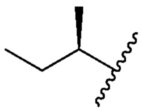 [SMILES: *[C@H](C)CC] | iso-propyl | iso-propyl |
| 114 | 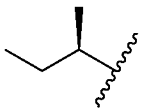 [SMILES: *[C@H](C)CC] | cyclopropyl | iso-propyl |
| 115 | 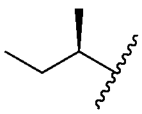 [SMILES: *[C@H](C)CC] | cyclobutyl | iso-propyl |
| 116 | 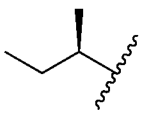 [SMILES: *[C@H](C)CC] | ethyl | tert-butyl |
| 117 | 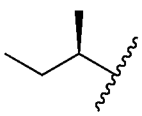 [SMILES: *[C@H](C)CC] | propyl | tert-butyl |
| 118 | 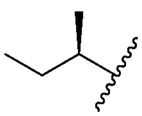 [SMILES: *[C@H](C)CC] | iso-propyl | tert-butyl |
| 119 | 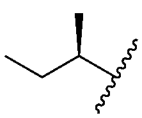 [SMILES: *[C@H](C)CC] | cyclopropyl | tert-butyl |

TABLE 1-continued

| Cpd. No. | $R^1$ | $R^2$ | $R^3$ |
|---|---|---|---|
| 120 | 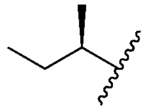 [SMILES: *[C@H](C)CC] | cyclobutyl | tert-butyl |
| 121 | 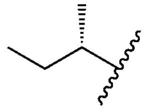 [SMILES: *[C@@H](C)CC] | ethyl | hydrogen |
| 122 | 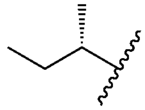 [SMILES: *[C@@H](C)CC] | propyl | hydrogen |
| 123 | 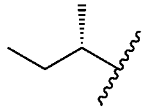 [SMILES: *[C@@H](C)CC] | iso-propyl | hydrogen |
| 124 | 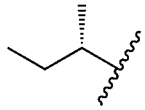 [SMILES: *[C@@H](C)CC] | cyclopropyl | hydrogen |
| 125 | 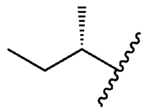 [SMILES: *[C@@H](C)CC] | cyclobutyl | hydrogen |
| 126 | 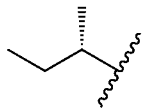 [SMILES: *[C@@H](C)CC] | ethyl | methyl |
| 127 | 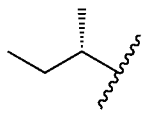 [SMILES: *[C@@H](C)CC] | propyl | methyl |
| 128 | 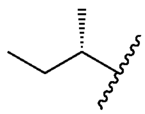 [SMILES: *[C@@H](C)CC] | iso-propyl | methyl |
| 129 | 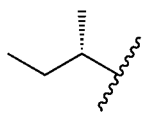 [SMILES: *[C@@H](C)CC] | cyclopropyl | methyl |
| 130 | 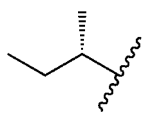 [SMILES: *[C@@H](C)CC] | cyclobutyl | methyl |
| 131 | 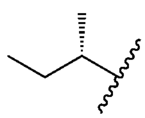 [SMILES: *[C@@H](C)CC] | ethyl | ethyl |

TABLE 1-continued

| Cpd. No. | $R^1$ | $R^2$ | $R^3$ |
|---|---|---|---|
| 132 | 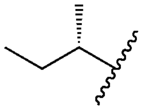 [SMILES: *[C@@H](C)CC] | propyl | ethyl |
| 133 | 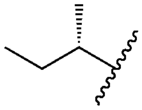 [SMILES: *[C@@H](C)CC] | iso-propyl | ethyl |
| 134 | 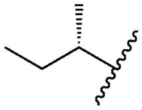 [SMILES: *[C@@H](C)CC] | cyclopropyl | ethyl |
| 135 | 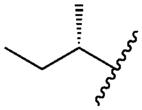 [SMILES: *[C@@H](C)CC] | cyclobutyl | ethyl |
| 136 | 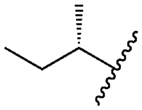 [SMILES: *[C@@H](C)CC] | ethyl | propyl |
| 137 | 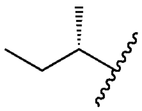 [SMILES: *[C@@H](C)CC] | propyl | propyl |
| 138 | 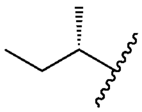 [SMILES: *[C@@H](C)CC] | iso-propyl | propyl |
| 139 | 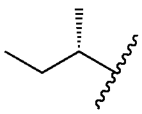 [SMILES: *[C@@H](C)CC] | cyclopropyl | propyl |
| 140 | 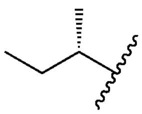 [SMILES: *[C@@H](C)CC] | cyclobutyl | propyl |
| 141 | 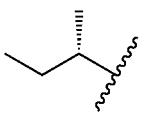 [SMILES: *[C@@H](C)CC] | ethyl | iso-propyl |
| 142 | 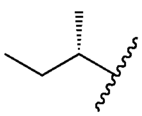 [SMILES: *[C@@H](C)CC] | propyl | iso-propyl |
| 143 | 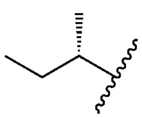 [SMILES: *[C@@H](C)CC] | iso-propyl | iso-propyl |
| 144 | 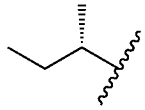 [SMILES: *[C@@H](C)CC] | cyclopropyl | iso-propyl |
| 145 | 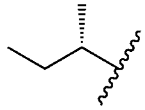 [SMILES: *[C@@H](C)CC] | cyclobutyl | iso-propyl |
| 146 | 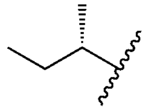 [SMILES: *[C@@H](C)CC] | ethyl | tert-butyl |
| 147 | 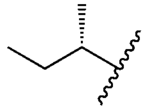 [SMILES: *[C@@H](C)CC] | propyl | tert-butyl |
| 148 | 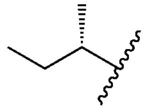 [SMILES: *[C@@H](C)CC] | iso-propyl | tert-butyl |
| 149 | 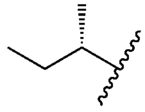 [SMILES: *[C@@H](C)CC] | cyclopropyl | tert-butyl |
| 150 | 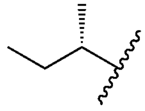 [SMILES: *[C@@H](C)CC] | cyclobutyl | tert-butyl |

In another embodiment, Compounds of the Disclosure are compounds of Formula II, or a pharmaceutically acceptable salt or solvate thereof, wherein $R^1$, $R^2$, and $R^3$ are as defined in Table 2.

TABLE 2

| Cpd. No. | $R^1$ | $R^2$ | $R^3$ |
|---|---|---|---|
| 151 | 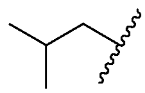 | ethyl | hydrogen |
| 152 | 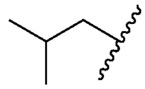 | propyl | hydrogen |
| 153 | 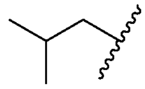 | iso-propyl | hydrogen |
| 154 | 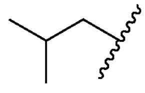 | cyclopropyl | hydrogen |

TABLE 2-continued

| Cpd. No. | $R^1$ | $R^2$ | $R^3$ |
| --- | --- | --- | --- |
| 155 | 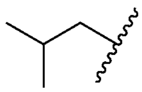 | cyclobutyl | hydrogen |
| 156 | 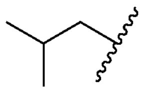 | ethyl | methyl |
| 157 | 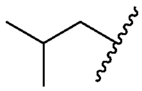 | propyl | methyl |
| 158 | 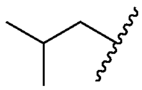 | iso-propyl | methyl |
| 159 | 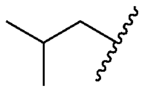 | cyclopropyl | methyl |
| 160 | 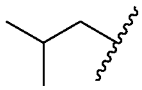 | cyclobutyl | methyl |
| 161 | 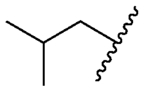 | ethyl | ethyl |
| 162 | 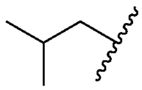 [SMILES: *CC(C)C] | propyl | ethyl |
| 163 | 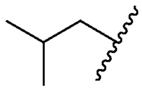 [SMILES: *CC(C)C] | iso-propyl | ethyl |
| 164 | 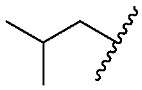 | cyclopropyl | ethyl |
| 165 | 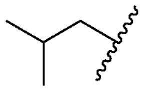 | cyclobutyl | ethyl |
| 166 | 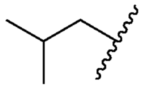 | ethyl | propyl |
| 167 | 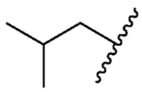 | propyl | propyl |
| 168 | 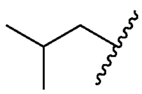 | iso-propyl | propyl |
| 169 | 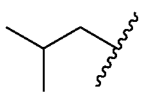 | cyclopropyl | propyl |

TABLE 2-continued

| Cpd. No. | $R^1$ | $R^2$ | $R^3$ |
| --- | --- | --- | --- |
| 170 | 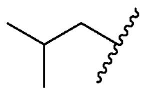 | cyclobutyl | propyl |
| 171 | 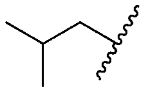 [SMILES: *CC(C)C] | ethyl | iso-propyl |
| 172 | 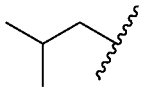 [SMILES: *CC(C)C] | propyl | iso-propyl |
| 173 | 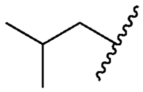 [SMILES: *CC(C)C] | iso-propyl | iso-propyl |
| 174 | 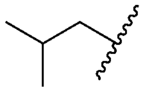 [SMILES: *CC(C)C] | cyclopropyl | iso-propyl |
| 175 | 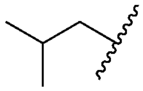 [SMILES: *CC(C)C] | cyclobutyl | iso-propyl |
| 176 | 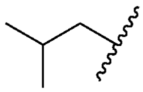 [SMILES: *CC(C)C] | ethyl | tert-butyl |
| 177 | 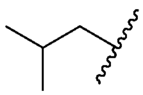 [SMILES: *CC(C)C] | propyl | tert-butyl |
| 178 | 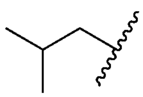 [SMILES: *CC(C)C] | iso-propyl | tert-butyl |
| 179 | 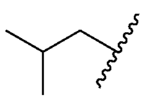 [SMILES: *CC(C)C] | cyclopropyl | tert-butyl |
| 180 | 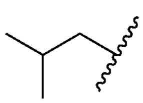 [SMILES: *CC(C)C] | cyclobutyl | tert-butyl |
| 181 | 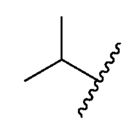 | ethyl | hydrogen |
| 182 | 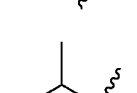 | propyl | hydrogen |
| 183 | 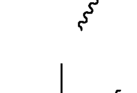 | iso-propyl | hydrogen |

TABLE 2-continued

| Cpd. No. | $R^1$ | $R^2$ | $R^3$ |
|---|---|---|---|
| 184 | 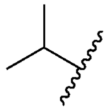 [SMILES: *C(C)C] | cyclopropyl | hydrogen |
| 185 | 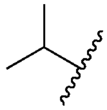 | cyclobutyl | hydrogen |
| 186 | 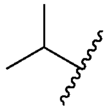 [SMILES: *C(C)C] | ethyl | methyl |
| 187 | 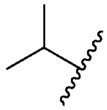 [SMILES: *C(C)C] | propyl | methyl |
| 188 | 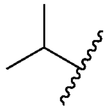 [SMILES: *C(C)C] | iso-propyl | methyl |
| 189 | 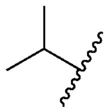 [SMILES: *C(C)C] | cyclopropyl | methyl |
| 190 | 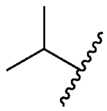 [SMILES: *C(C)C] | cyclobutyl | methyl |
| 191 | 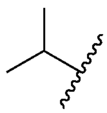 [SMILES: *C(C)C] | ethyl | ethyl |
| 192 | 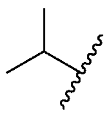 [SMILES: *C(C)C] | propyl | ethyl |
| 193 | 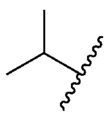 [SMILES: *C(C)C] | iso-propyl | ethyl |
| 194 | 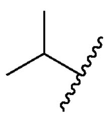 [SMILES: *C(C)C] | cyclopropyl | ethyl |
| 195 | 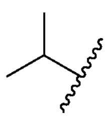 [SMILES: *C(C)C] | cyclobutyl | ethyl |

TABLE 2-continued

| Cpd. No. | $R^1$ | $R^2$ | $R^3$ |
|---|---|---|---|
| 196 | 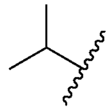 | ethyl | propyl |
| 197 | 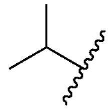 [SMILES: *C(C)C] | propyl | propyl |
| 198 | 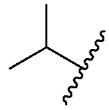 [SMILES: *C(C)C] | iso-propyl | propyl |
| 199 | 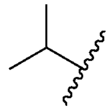 | cyclopropyl | propyl |
| 200 | 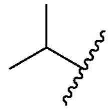 [SMILES: *C(C)C] | cyclobutyl | propyl |
| 201 | 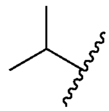 | ethyl | iso-propyl |
| 202 | 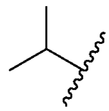 | propyl | iso-propyl |
| 203 | 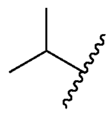 | iso-propyl | iso-propyl |
| 204 | 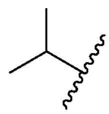 | cyclopropyl | iso-propyl |
| 205 | 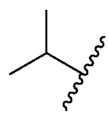 [SMILES: *C(C)C] | cyclobutyl | iso-propyl |
| 206 | 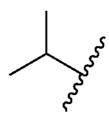 | ethyl | tert-butyl |
| 207 | 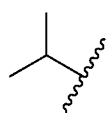 | propyl | tert-butyl |

TABLE 2-continued

| Cpd. No. | $R^1$ | $R^2$ | $R^3$ |
|---|---|---|---|
| 208 | 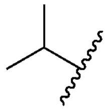 [SMILES: *C(C)C] | iso-propyl | tert-butyl |
| 209 | 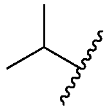 | cyclopropyl | tert-butyl |
| 210 | 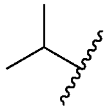 [SMILES: *C(C)C] | cyclobutyl | tert-butyl |
| 211 | 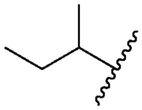 [SMILES: *C(C)CC] | ethyl | hydrogen |
| 212 | 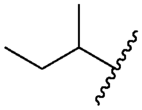 [SMILES: *C(C)CC] | propyl | hydrogen |
| 213 | 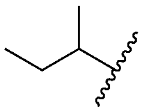 [SMILES: *C(C)CC] | iso-propyl | hydrogen |
| 214 | 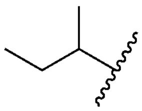 [SMILES: *C(C)CC] | cyclopropyl | hydrogen |
| 215 | 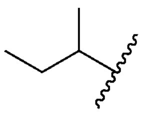 [SMILES: *C(C)CC] | cyclobutyl | hydrogen |
| 216 | 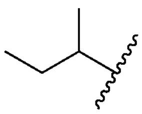 [SMILES: *C(C)CC] | ethyl | methyl |
| 217 | 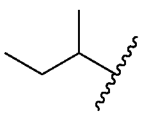 [SMILES: *C(C)CC] | propyl | methyl |
| 218 | 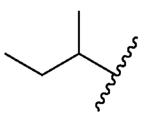 [SMILES: *C(C)CC] | iso-propyl | methyl |
| 219 | 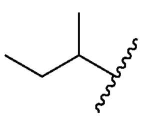 [SMILES: *C(C)CC] | cyclopropyl | methyl |

TABLE 2-continued

| Cpd. No. | $R^1$ | $R^2$ | $R^3$ |
|---|---|---|---|
| 220 | 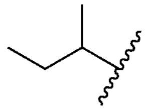 [SMILES: *C(C)CC] | cyclobutyl | methyl |
| 221 | 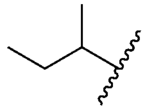 [SMILES: *C(C)CC] | ethyl | ethyl |
| 222 | 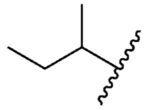 [SMILES: *C(C)CC] | propyl | ethyl |
| 223 | 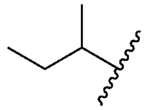 [SMILES: *C(C)CC] | iso-propyl | ethyl |
| 224 | 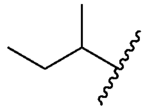 [SMILES: *C(C)CC] | cyclopropyl | ethyl |
| 225 | 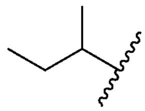 [SMILES: *C(C)CC] | cyclobutyl | ethyl |
| 226 | 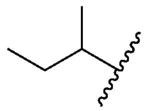 [SMILES: *C(C)CC] | ethyl | propyl |
| 227 | 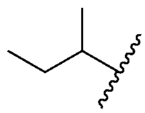 [SMILES: *C(C)CC] | propyl | propyl |
| 228 | 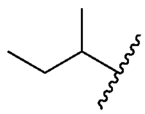 [SMILES: *C(C)CC] | iso-propyl | propyl |
| 229 | 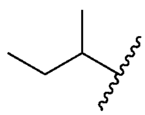 [SMILES: *C(C)CC] | cyclopropyl | propyl |
| 230 | 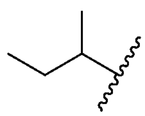 [SMILES: *C(C)CC] | cyclobutyl | propyl |
| 231 | 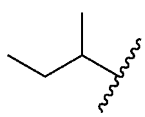 [SMILES: *C(C)CC] | ethyl | iso-propyl |

TABLE 2-continued

| Cpd. No. | $R^1$ | $R^2$ | $R^3$ |
|---|---|---|---|
| 232 | 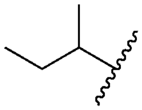 [SMILES: *C(C)CC] | propyl | iso-propyl |
| 233 | 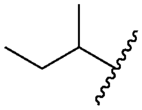 [SMILES: *C(C)CC] | iso-propyl | iso-propyl |
| 234 | 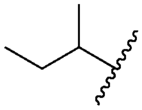 [SMILES: *C(C)CC] | cyclopropyl | iso-propyl |
| 235 | 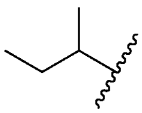 [SMILES: *C(C)CC] | cyclobutyl | iso-propyl |
| 236 | 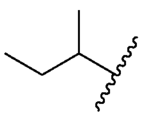 [SMILES: *C(C)CC] | ethyl | tert-butyl |
| 237 | 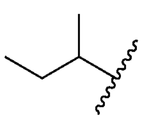 [SMILES: *C(C)CC] | propyl | tert-butyl |
| 238 | 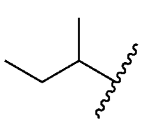 [SMILES: *C(C)CC] | iso-propyl | tert-butyl |
| 239 | 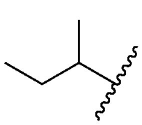 [SMILES: *C(C)CC] | cyclopropyl | tert-butyl |
| 240 | 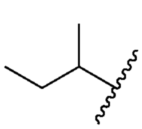 [SMILES: *C(C)CC] | cyclobutyl | tert-butyl |
| 241 | 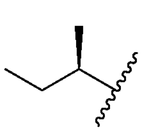 [SMILES: *[C@H](C)CC] | ethyl | hydrogen |
| 242 | 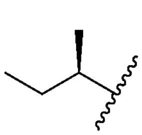 [SMILES: *[C@H](C)CC] | propyl | hydrogen |
| 243 | 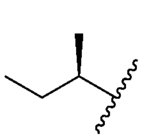 [SMILES: *[C@H](C)CC] | iso-propyl | hydrogen |

TABLE 2-continued

| Cpd. No. | $R^1$ | $R^2$ | $R^3$ |
|---|---|---|---|
| 244 | 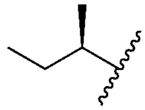 [SMILES: *[C@H](C)CC] | cyclopropyl | hydrogen |
| 245 | 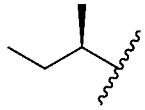 [SMILES: *[C@H](C)CC] | cyclobutyl | hydrogen |
| 246 | 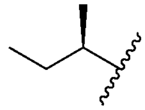 [SMILES: *[C@H](C)CC] | ethyl | methyl |
| 247 | 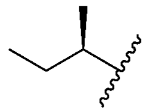 [SMILES: *[C@H](C)CC] | propyl | methyl |
| 248 | 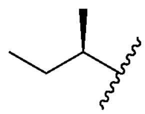 [SMILES: *[C@H](C)CC] | iso-propyl | methyl |
| 249 | 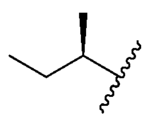 [SMILES: *[C@H](C)CC] | cyclopropyl | methyl |
| 250 | 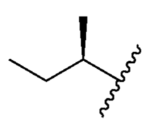 | cyclobutyl | methyl |
| 251 | 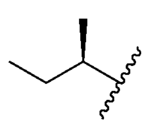 [SMILES: *[C@H](C)CC] | ethyl | ethyl |
| 252 | 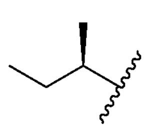 [SMILES: *[C@H](C)CC] | propyl | ethyl |
| 253 | 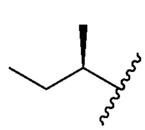 [SMILES: *[C@H](C)CC] | iso-propyl | ethyl |
| 254 | 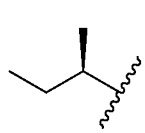 [SMILES: *[C@H](C)CC] | cyclopropyl | ethyl |
| 255 | 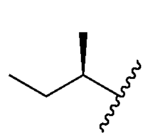 [SMILES: *[C@H](C)CC] | cyclobutyl | ethyl |

TABLE 2-continued

| Cpd. No. | R¹ | R² | R³ |
|---|---|---|---|
| 256 | 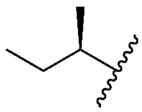 [SMILES: *[C@H](C)CC] | ethyl | propyl |
| 257 | 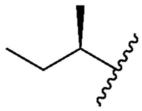 [SMILES: *[C@H](C)CC] | propyl | propyl |
| 258 | 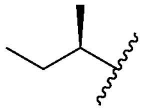 [SMILES: *[C@H](C)CC] | iso-propyl | propyl |
| 259 | 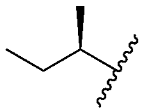 [SMILES: *[C@H](C)CC] | cyclopropyl | propyl |
| 260 | 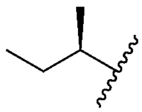 [SMILES: *[C@H](C)CC] | cyclobutyl | propyl |
| 261 | 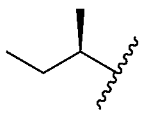 [SMILES: *[C@H](C)CC] | ethyl | iso-propyl |
| 262 | 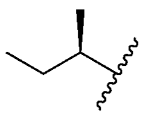 | propyl | iso-propyl |
| 263 | 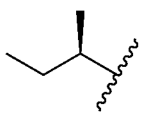 [SMILES: *[C@H](C)CC] | iso-propyl | iso-propyl |
| 264 | 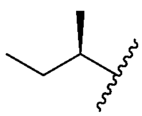 [SMILES: *[C@H](C)CC] | cyclopropyl | iso-propyl |
| 265 | 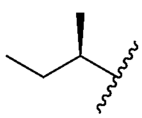 [SMILES: *[C@H](C)CC] | cyclobutyl | iso-propyl |
| 266 | 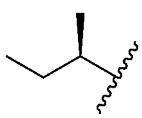 [SMILES: *[C@H](C)CC] | ethyl | tert-butyl |
| 267 | 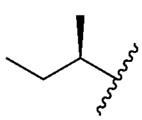 [SMILES: *[C@H](C)CC] | propyl | tert-butyl |

TABLE 2-continued

| Cpd. No. | R¹ | R² | R³ |
|---|---|---|---|
| 268 | 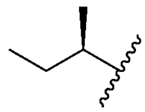 [SMILES: *[C@H](C)CC] | iso-propyl | tert-butyl |
| 269 | 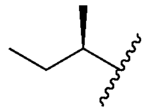 [SMILES: *[C@H](C)CC] | cyclopropyl | tert-butyl |
| 270 | 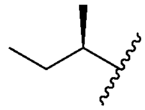 [SMILES: *[C@H](C)CC] | cyclobutyl | tert-butyl |
| 271 | 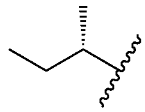 [SMILES: *[C@@H](C)CC] | ethyl | hydrogen |
| 272 | 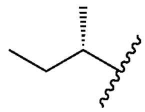 [SMILES: *[C@@H](C)CC] | propyl | hydrogen |
| 273 | 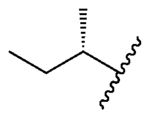 [SMILES: *[C@@H](C)CC] | iso-propyl | hydrogen |
| 274 | 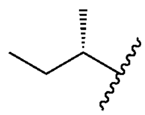 | cyclopropyl | hydrogen |
| 275 | 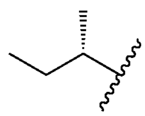 [SMILES: *[C@@H](C)CC] | cyclobutyl | hydrogen |
| 276 | 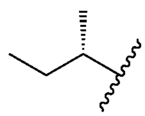 [SMILES: *[C@@H](C)CC] | ethyl | methyl |
| 277 | 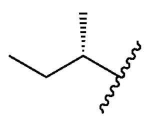 [SMILES: *[C@@H](C)CC] | propyl | methyl |
| 278 | 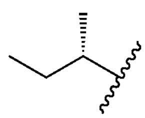 [SMILES: *[C@@H](C)CC] | iso-propyl | methyl |
| 279 | 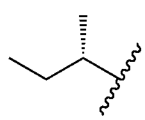 [SMILES: *[C@@H](C)CC] | cyclopropyl | methyl |

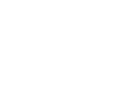

TABLE 2-continued

| Cpd. No. | $R^1$ | $R^2$ | $R^3$ |
|---|---|---|---|
| 280 | 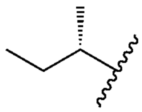 [SMILES: *[C@@H](C)CC] | cyclobutyl | methyl |
| 281 | 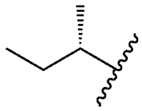 | ethyl | ethyl |
| 282 | 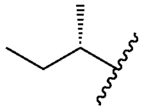 [SMILES: *[C@@H](C)CC] | propyl | ethyl |
| 283 | 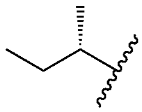 [SMILES: *[C@@H](C)CC] | iso-propyl | ethyl |
| 284 | 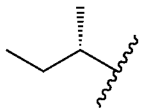 [SMILES: *[C@@H](C)CC] | cyclopropyl | ethyl |
| 285 | 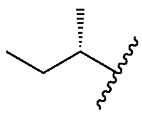 [SMILES: *[C@@H](C)CC] | cyclobutyl | ethyl |
| 286 | 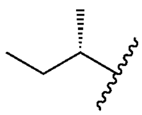 | ethyl | propyl |
| 287 | 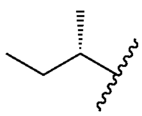 [SMILES: *[C@@H](C)CC] | propyl | propyl |
| 288 | 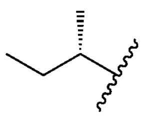 [SMILES: *[C@@H](C)CC] | iso-propyl | propyl |
| 289 | 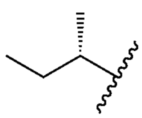 [SMILES: *[C@@H](C)CC] | cyclopropyl | propyl |
| 290 | 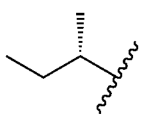 [SMILES: *[C@@H](C)CC] | cyclobutyl | propyl |
| 291 | 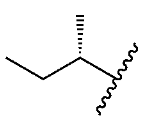 [SMILES: *[C@@H](C)CC] | ethyl | iso-propyl |
| 292 | 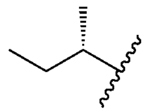 [SMILES: *[C@@H](C)CC] | propyl | iso-propyl |
| 293 | 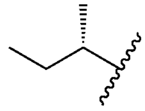 [SMILES: *[C@@H](C)CC] | iso-propyl | iso-propyl |
| 294 | 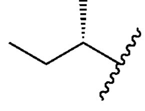 [SMILES: *[C@@H](C)CC] | cyclopropyl | iso-propyl |
| 295 | 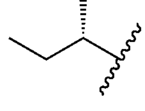 | cyclobutyl | iso-propyl |
| 296 | 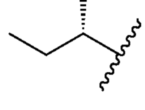 | ethyl | tert-butyl |
| 297 | 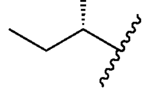 | propyl | tert-butyl |
| 298 | 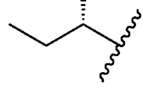 | iso-propyl | tert-butyl |
| 299 | 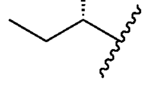 | cyclopropyl | tert-butyl |
| 300 | 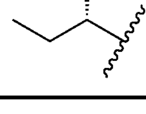 | cyclobutyl | tert-butyl |

In another embodiment, Compounds of the Disclosure are compounds of Formula III, or a pharmaceutically acceptable salt or solvate thereof, wherein $R^1$, $R^2$, and $R^3$ are as defined in Table 3.

TABLE 3

| Cpd. No. | $R^1$ | $R^2$ | $R^3$ |
|---|---|---|---|
| 301 | 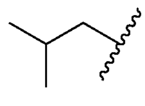 [SMILES: *CC(C)C] | ethyl | hydrogen |
| 302 | 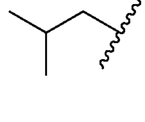 | propyl | hydrogen |

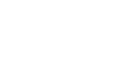

TABLE 3-continued

| Cpd. No. | $R^1$ | $R^2$ | $R^3$ |
|---|---|---|---|
| 303 | 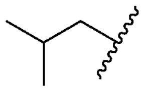 [SMILES: *CC(C)C] | iso-propyl | hydrogen |
| 304 | 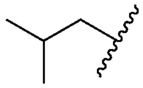 | cyclopropyl | hydrogen |
| 305 | 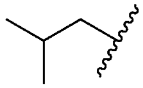 | cyclobutyl | hydrogen |
| 306 | 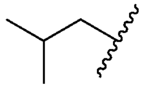 | ethyl | methyl |
| 307 | 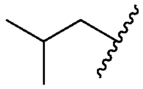 | propyl | methyl |
| 308 | 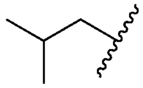 | iso-propyl | methyl |
| 309 | 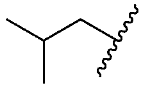 | cyclopropyl | methyl |
| 310 | 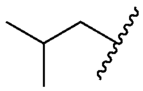 | cyclobutyl | methyl |
| 311 | 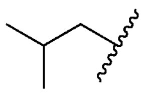 | ethyl | ethyl |
| 312 | 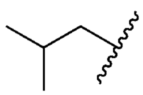 | propyl | ethyl |
| 313 | 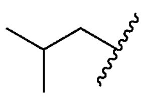 | iso-propyl | ethyl |
| 314 | 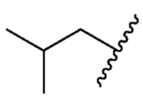 | cyclopropyl | ethyl |
| 315 | 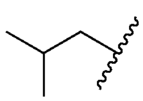 | cyclobutyl | ethyl |
| 316 | 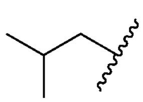 | ethyl | propyl |
| 317 | 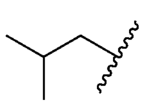 | propyl | propyl |

TABLE 3-continued

| Cpd. No. | $R^1$ | $R^2$ | $R^3$ |
|---|---|---|---|
| 318 | 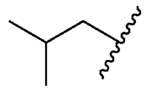 [SMILES: *CC(C)C] | iso-propyl | propyl |
| 319 | 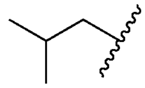 | cyclopropyl | propyl |
| 320 | 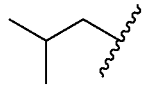 [SMILES: *CC(C)C] | cyclobutyl | propyl |
| 321 | 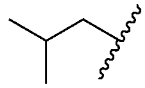 [SMILES: *CC(C)C] | ethyl | iso-propyl |
| 322 | 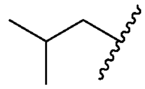 [SMILES: *CC(C)C] | propyl | iso-propyl |
| 323 | 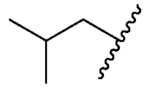 | iso-propyl | iso-propyl |
| 324 | 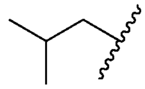 | cyclopropyl | iso-propyl |
| 325 | 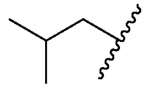 [SMILES: *CC(C)C] | cyclobutyl | iso-propyl |
| 326 | 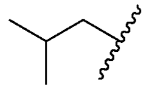 [SMILES: *CC(C)C] | ethyl | tert-butyl |
| 327 | 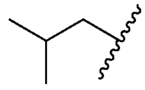 | propyl | tert-butyl |
| 328 | 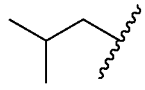 | iso-propyl | tert-butyl |
| 329 | 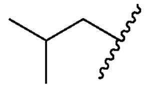 [SMILES: *CC(C)C] | cyclopropyl | tert-butyl |
| 330 | 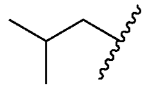 [SMILES: *CC(C)C] | cyclobutyl | tert-butyl |
| 331 | 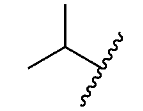 [SMILES: *C(C)C] | ethyl | hydrogen |
| 332 | 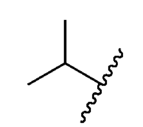 [SMILES: *C(C)C] | propyl | hydrogen |

TABLE 3-continued

| Cpd. No. | $R^1$ | $R^2$ | $R^3$ |
|---|---|---|---|
| 333 | 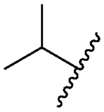 [SMILES: *C(C)C] | iso-propyl | hydrogen |
| 334 | 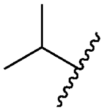 [SMILES: *C(C)C] | cyclopropyl | hydrogen |
| 335 | 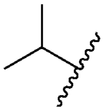 | cyclobutyl | hydrogen |
| 336 | 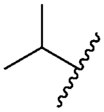 [SMILES: *C(C)C] | ethyl | methyl |
| 337 | 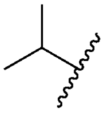 | propyl | methyl |
| 338 | 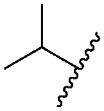 | iso-propyl | methyl |
| 339 | 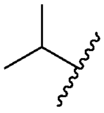 [SMILES: *C(C)C] | cyclopropyl | methyl |
| 340 | 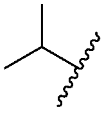 [SMILES: *C(C)C] | cyclobutyl | methyl |
| 341 | 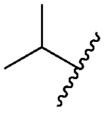 | ethyl | ethyl |
| 342 | 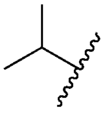 | propyl | ethyl |
| 343 | 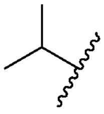 [SMILES: *C(C)C] | iso-propyl | ethyl |
| 344 | 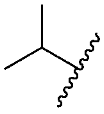 | cyclopropyl | ethyl |

TABLE 3-continued

| Cpd. No. | $R^1$ | $R^2$ | $R^3$ |
|---|---|---|---|
| 345 | 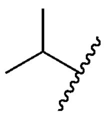 | cyclobutyl | ethyl |
| 346 | 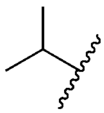 [SMILES: *C(C)C] | ethyl | propyl |
| 347 | 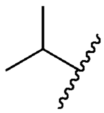 [SMILES: *C(C)C] | propyl | propyl |
| 348 | 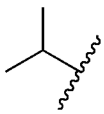 [SMILES: *C(C)C] | iso-propyl | propyl |
| 349 | 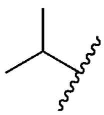 [SMILES: *C(C)C] | cyclopropyl | propyl |
| 350 | 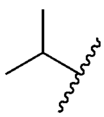 | cyclobutyl | propyl |
| 351 | 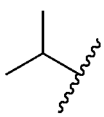 [SMILES: *C(C)C] | ethyl | iso-propyl |
| 352 | 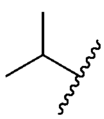 | propyl | iso-propyl |
| 353 | 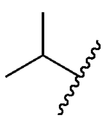 | iso-propyl | iso-propyl |
| 354 | 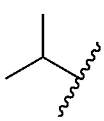 [SMILES: *C(C)C] | cyclopropyl | iso-propyl |
| 355 | 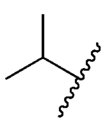 | cyclobutyl | iso-propyl |
| 356 | 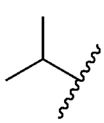 | ethyl | tert-butyl |

TABLE 3-continued

| Cpd. No. | $R^1$ | $R^2$ | $R^3$ |
|---|---|---|---|
| 357 | 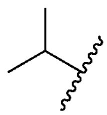 [SMILES: *C(C)C] | propyl | tert-butyl |
| 358 | 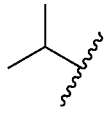 | iso-propyl | tert-butyl |
| 359 | 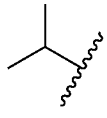 | cyclopropyl | tert-butyl |
| 360 | 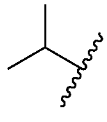 [SMILES: *C(C)C] | cyclobutyl | tert-butyl |
| 361 | 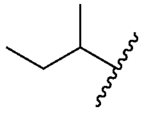 [SMILES: *C(C)CC] | ethyl | hydrogen |
| 362 | 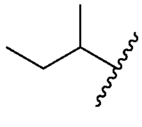 [SMILES: *C(C)CC] | propyl | hydrogen |
| 363 | 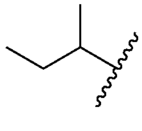 [SMILES: *C(C)CC] | iso-propyl | hydrogen |
| 364 | 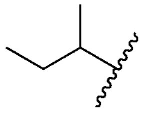 [SMILES: *C(C)CC] | cyclopropyl | hydrogen |
| 365 | 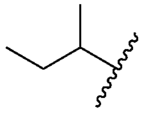 [SMILES: *C(C)CC] | cyclobutyl | hydrogen |
| 366 | 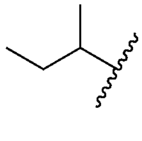 [SMILES: *C(C)CC] | ethyl | methyl |
| 367 | 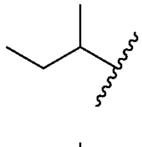 | propyl | methyl |
| 368 | 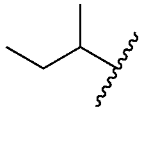 [SMILES: *C(C)CC] | iso-propyl | methyl |
| 369 | 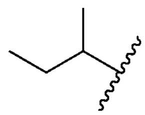 [SMILES: *C(C)CC] | cyclopropyl | methyl |
| 370 | 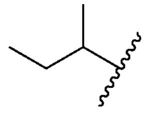 [SMILES: *C(C)CC] | cyclobutyl | methyl |
| 371 | 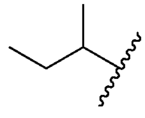 [SMILES: *C(C)CC] | ethyl | ethyl |
| 372 | 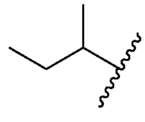 [SMILES: *C(C)CC] | propyl | ethyl |
| 373 | 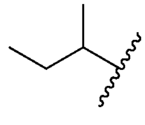 [SMILES: *C(C)CC] | iso-propyl | ethyl |
| 374 | 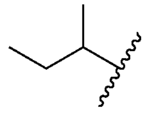 [SMILES: *C(C)CC] | cyclopropyl | ethyl |
| 375 | 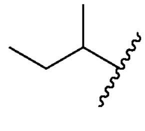 [SMILES: *C(C)CC] | cyclobutyl | ethyl |
| 376 | 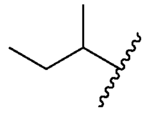 [SMILES: *C(C)CC] | ethyl | propyl |
| 377 | 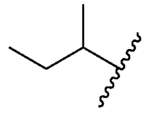 [SMILES: *C(C)CC] | propyl | propyl |
| 378 | 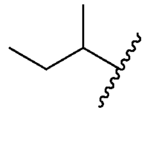 [SMILES: *C(C)CC] | iso-propyl | propyl |
| 379 | 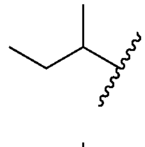 | cyclopropyl | propyl |
| 380 | 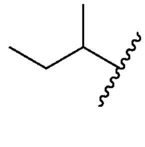 [SMILES: *C(C)CC] | cyclobutyl | propyl |

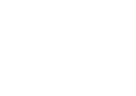

TABLE 3-continued

| Cpd. No. | $R^1$ | $R^2$ | $R^3$ |
|---|---|---|---|
| 381 | 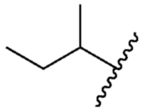 [SMILES: *C(C)CC] | ethyl | iso-propyl |
| 382 | 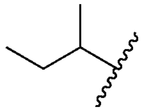 [SMILES: *C(C)CC] | propyl | iso-propyl |
| 383 | 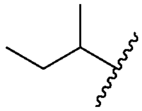 [SMILES: *C(C)CC] | iso-propyl | iso-propyl |
| 384 | 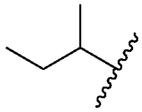 [SMILES: *C(C)CC] | cyclopropyl | iso-propyl |
| 385 | 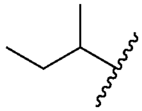 [SMILES: *C(C)CC] | cyclobutyl | iso-propyl |
| 386 | 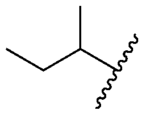 [SMILES: *C(C)CC] | ethyl | tert-butyl |
| 387 | 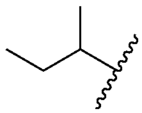 [SMILES: *C(C)CC] | propyl | tert-butyl |
| 388 | 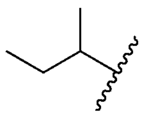 [SMILES: *C(C)CC] | iso-propyl | tert-butyl |
| 389 | 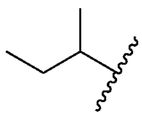 [SMILES: *C(C)CC] | cyclopropyl | tert-butyl |
| 390 | 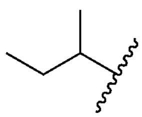 [SMILES: *C(C)CC] | cyclobutyl | tert-butyl |
| 391 | 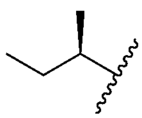 [SMILES: *[C@H](C)CC] | ethyl | hydrogen |
| 392 | 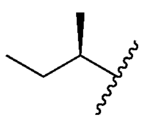 [SMILES: *[C@H](C)CC] | propyl | hydrogen |

TABLE 3-continued

| Cpd. No. | $R^1$ | $R^2$ | $R^3$ |
|---|---|---|---|
| 393 | 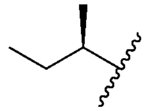 [SMILES: *[C@H](C)CC] | iso-propyl | hydrogen |
| 394 | 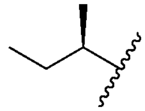 [SMILES: *[C@H](C)CC] | cyclopropyl | hydrogen |
| 395 | 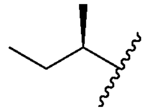 [SMILES: *[C@H](C)CC] | cyclobutyl | hydrogen |
| 396 | 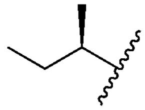 [SMILES: *[C@H](C)CC] | ethyl | methyl |
| 397 | 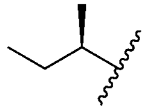 [SMILES: *[C@H](C)CC] | propyl | methyl |
| 398 | 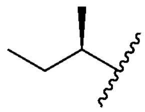 [SMILES: *[C@H](C)CC] | iso-propyl | methyl |
| 399 | 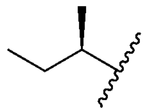 [SMILES: *[C@H](C)CC] | cyclopropyl | methyl |
| 400 | 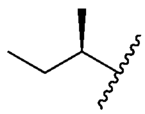 [SMILES: *[C@H](C)CC] | cyclobutyl | methyl |
| 401 | 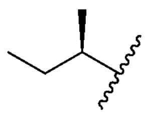 [SMILES: *[C@H](C)CC] | ethyl | ethyl |
| 402 | 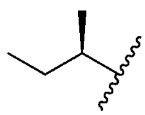 [SMILES: *[C@H](C)CC] | propyl | ethyl |
| 403 | 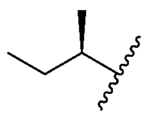 [SMILES: *[C@H](C)CC] | iso-propyl | ethyl |
| 404 | 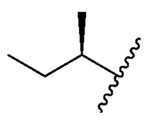 [SMILES: *[C@H](C)CC] | cyclopropyl | ethyl |

TABLE 3-continued

| Cpd. No. | $R^1$ | $R^2$ | $R^3$ |
|---|---|---|---|
| 405 | 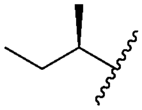 [SMILES: *[C@H](C)CC] | cyclobutyl | ethyl |
| 406 | 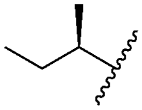 [SMILES: *[C@H](C)CC] | ethyl | propyl |
| 407 | 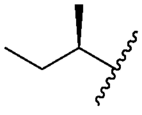 [SMILES: *[C@H](C)CC] | propyl | propyl |
| 408 | 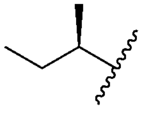 [SMILES: *[C@H](C)CC] | iso-propyl | propyl |
| 409 | 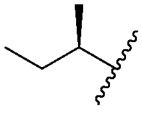 [SMILES: *[C@H](C)CC] | cyclopropyl | propyl |
| 410 | 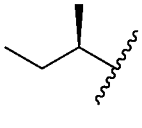 [SMILES: *[C@H](C)CC] | cyclobutyl | propyl |
| 411 | 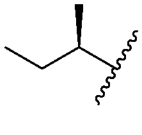 [SMILES: *[C@H](C)CC] | ethyl | iso-propyl |
| 412 | 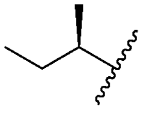 [SMILES: *[C@H](C)CC] | propyl | iso-propyl |
| 413 | 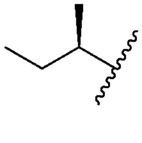 [SMILES: *[C@H](C)CC] | iso-propyl | iso-propyl |
| 414 | 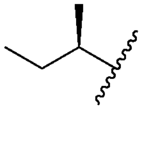 [SMILES: *[C@H](C)CC] | cyclopropyl | iso-propyl |
| 415 | 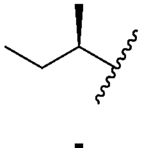 | cyclobutyl | iso-propyl |
| 416 | 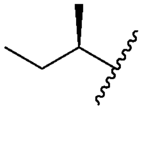 [SMILES: *[C@H](C)CC] | ethyl | tert-butyl |

TABLE 3-continued

| Cpd. No. | $R^1$ | $R^2$ | $R^3$ |
|---|---|---|---|
| 417 | 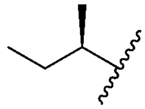 [SMILES: *[C@H](C)CC] | propyl | tert-butyl |
| 418 | 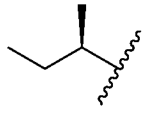 [SMILES: *[C@H](C)CC] | iso-propyl | tert-butyl |
| 419 | 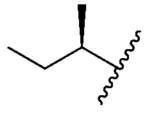 [SMILES: *[C@H](C)CC] | cyclopropyl | tert-butyl |
| 420 | 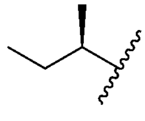 [SMILES: *[C@H](C)CC] | cyclobutyl | tert-butyl |
| 421 | 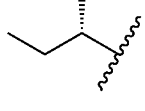 | ethyl | hydrogen |
| 422 | 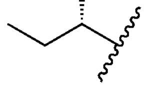 | propyl | hydrogen |
| 423 | 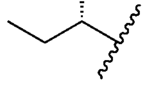 | iso-propyl | hydrogen |
| 424 | 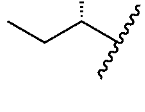 | cyclopropyl | hydrogen |
| 425 | 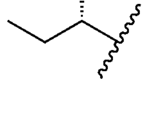 | cyclobutyl | hydrogen |
| 426 | 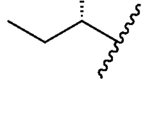 | ethyl | methyl |
| 427 | 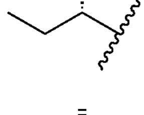 | propyl | methyl |
| 428 | 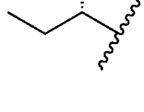 | iso-propyl | methyl |

TABLE 3-continued

| Cpd. No. | $R^1$ | $R^2$ | $R^3$ |
|---|---|---|---|
| 429 | 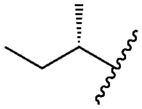 [SMILES: *[C@@H](C)CC] | cyclopropyl | methyl |
| 430 | 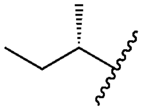 [SMILES: *[C@@H](C)CC] | cyclobutyl | methyl |
| 431 | 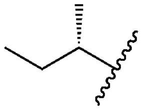 [SMILES: *[C@@H](C)CC] | ethyl | ethyl |
| 432 | 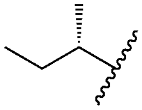 [SMILES: *[C@@H](C)CC] | propyl | ethyl |
| 433 | 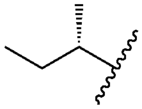 [SMILES: *[C@@H](C)CC] | iso-propyl | ethyl |
| 434 | 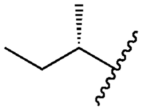 [SMILES: *[C@@H](C)CC] | cyclopropyl | ethyl |
| 435 | 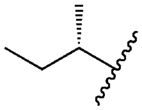 [SMILES: *[C@@H](C)CC] | cyclobutyl | ethyl |
| 436 | 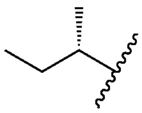 [SMILES: *[C@@H](C)CC] | ethyl | propyl |
| 437 | 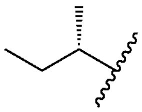 [SMILES: *[C@@H](C)CC] | propyl | propyl |
| 438 | 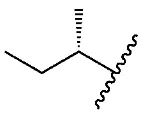 [SMILES: *[C@@H](C)CC] | iso-propyl | propyl |
| 439 | 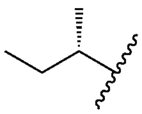 [SMILES: *[C@@H](C)CC] | cyclopropyl | propyl |
| 440 | 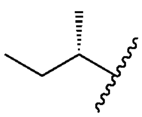 [SMILES: *[C@@H](C)CC] | cyclobutyl | propyl |
| 441 | 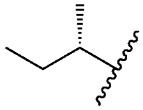 [SMILES: *[C@@H](C)CC] | ethyl | iso-propyl |
| 442 | 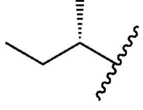 [SMILES: *[C@@H](C)CC] | propyl | iso-propyl |
| 443 | 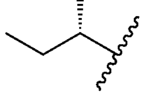 | iso-propyl | iso-propyl |
| 444 | 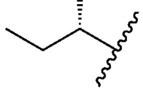 | cyclopropyl | iso-propyl |
| 445 | 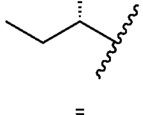 | cyclobutyl | iso-propyl |
| 446 | 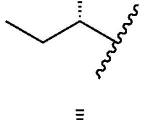 | ethyl | tert-butyl |
| 447 | 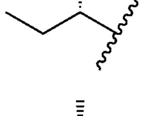 | propyl | tert-butyl |
| 448 | 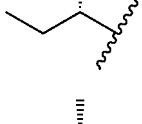 | iso-propyl | tert-butyl |
| 449 | 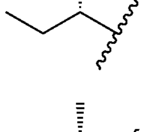 | cyclopropyl | tert-butyl |
| 450 | 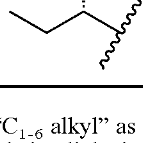 | cyclobutyl | tert-butyl |

The term "$C_{1-6}$ alkyl" as used herein refers to a straight- or branched-chain aliphatic hydrocarbon containing one to six carbon atoms. Non-limiting exemplary $C_{1-6}$ alkyl groups include methyl, ethyl, propyl, iso-propyl, butyl, sec-butyl, tert-butyl, iso-butyl, 3-pentyl, and hexyl. In one embodiment, the $C_{1-6}$ alkyl is methyl. In another embodiment, the $C_{1-6}$ alkyl is ethyl. In another embodiment, the $C_{1-6}$ alkyl is propyl. In another embodiment, the $C_{1-6}$ alkyl is iso-propyl. In another embodiment, the $C_{1-6}$ alkyl is tert-butyl.

The term "$C_{2-6}$ alkyl" as used herein refers to a straight- or branched-chain aliphatic hydrocarbon containing two to six carbon atoms. Non-limiting exemplary $C_{2-6}$ alkyl groups include ethyl, propyl, iso-propyl, butyl, sec-butyl, tert-butyl, iso-butyl, 3-pentyl, and hexyl. In one embodiment, the $C_{2-6}$ alkyl is ethyl. In another embodiment, the $C_{2-6}$ alkyl is propyl. In another embodiment, the $C_{2-6}$ alkyl is iso-propyl. In another embodiment, the $C_{2-6}$ alkyl is tert-butyl.

The term "$C_{3-6}$ cycloalkyl" as used herein refers to a monocyclic aliphatic hydrocarbon containing three to six carbon atoms. In one embodiment, the $C_{3-6}$ cycloalkyl is cyclopropyl. In another embodiment, the $C_{3-6}$ cycloalkyl is cyclobutyl. In another embodiment, the $C_{3-6}$ cycloalkyl is cyclopentyl, In another embodiment, the $C_{3-6}$ cycloalkyl is cyclohexyl.

As used herein, the term "stereoisomers" is a general term for all isomers of an individual molecule that differ only in the orientation of their atoms in space. It includes enantiomers and isomers of compounds with more than one chiral center that are not mirror images of one another (diastereomers).

The term "chiral center" or "asymmetric carbon atom" refers to a carbon atom to which four different groups are attached.

The terms "enantiomer" and "enantiomeric" refer to a molecule that cannot be superimposed on its mirror image and hence is optically active wherein the enantiomer rotates the plane of polarized light in one direction and its mirror image compound rotates the plane of polarized light in the opposite direction.

The term "racemic" refers to a mixture of equal parts of enantiomers and which mixture is optically inactive.

The term "absolute configuration" refers to the spatial arrangement of the atoms of a chiral molecular entity (or group) and its stereochemical description, e.g., R or S.

The stereochemical terms and conventions used in the specification are meant to be consistent with those described in *Pure & Appl. Chem* 68:2193 (1996), unless otherwise indicated.

The term "enantiomeric excess" or "ee" refers to a measure for how much of one enantiomer is present compared to the other. For a mixture of R and S enantiomers, the percent enantiomeric excess is defined as $|R-S|*100$, where R and S are the respective mole or weight fractions of enantiomers in a mixture such that R+S=1. With knowledge of the optical rotation of a chiral substance, the percent enantiomeric excess is defined as $([\alpha]_{obs}/[\alpha]_{max})*100$, where $[\alpha]_{obs}$ is the optical rotation of the mixture of enantiomers and $[\alpha]_{max}$ is the optical rotation of the pure enantiomer. Determination of enantiomeric excess is possible using a variety of analytical techniques, including NMR spectroscopy, chiral column chromatography, or optical polarimetry.

Salts and solvates, e.g., hydrates, of the Compounds of the Disclosure can also be used in the methods disclosed herein.

The present disclosure encompasses the preparation and use of salts of Compounds of the Disclosure. As used herein, a "pharmaceutically acceptable salt" refers to salts or zwitterionic forms of Compounds of the Disclosure. Salts of Compounds of the Disclosure can be prepared during the final isolation and purification of the compounds or separately by reacting the compound with an acid having a suitable cation. The pharmaceutically acceptable salts of Compounds of the Disclosure can be acid addition salts formed with pharmaceutically acceptable acids. Examples of acids which can be employed to form pharmaceutically acceptable salts include inorganic acids such as nitric, boric, hydrochloric, hydrobromic, sulfuric, and phosphoric, and organic acids such as oxalic, maleic, succinic, and citric. Non-limiting examples of salts of compounds of the disclosure include, but are not limited to, the hydrochloride, hydrobromide, hydroiodide, sulfate, bisulfate, 2-hydroxyethansulfonate, phosphate, hydrogen phosphate, acetate, adipate, alginate, aspartate, benzoate, bisulfate, butyrate, camphorate, camphorsulfonate, digluconate, glycerolphosphate, hemisulfate, heptanoate, hexanoate, formate, succinate, fumarate, maleate, ascorbate, isethionate, salicylate, methanesulfonate, mesitylenesulfonate, naphthylenesulfonate, nicotinate, 2-naphthalenesulfonate, oxalate, pamoate, pectinate, persulfate, 3-phenylproprionate, picrate, pivalate, propionate, trichloroacetate, trifluoroacetate, phosphate, glutamate, bicarbonate, paratoluenesulfonate, undecanoate, lactate, citrate, tartrate, gluconate, methanesulfonate, ethanedisulfonate, benzene sulfonate, and p-toluenesulfonate salts. In addition, available amino groups present in the compounds of the disclosure can be quaternized with methyl, ethyl, propyl, and butyl chlorides, bromides, and iodides; dimethyl, diethyl, dibutyl, and diamyl sulfates; decyl, lauryl, myristyl, and steryl chlorides, bromides, and iodides; and benzyl and phenethyl bromides. In light of the foregoing, any reference to Compounds of the Disclosure appearing herein is intended to include Compounds of the Disclosure as well as pharmaceutically acceptable salts, hydrates, or solvates thereof.

The present disclosure encompasses the preparation and use of solvates of Compounds of the Disclosure. Solvates typically do not significantly alter the physiological activity or toxicity of the compounds, and as such may function as pharmacological equivalents. The term "solvate" as used herein is a combination, physical association and/or solvation of a compound of the present disclosure with a solvent molecule such as, e.g., a disolvate, monosolvate or hemisolvate, where the ratio of solvent molecule to compound of the present disclosure is about 2:1, about 1:1 or about 1:2, respectively. This physical association involves varying degrees of ionic and covalent bonding, including hydrogen bonding. In certain instances, the solvate can be isolated, such as when one or more solvent molecules are incorporated into the crystal lattice of a crystalline solid. Thus, "solvate" encompasses both solution-phase and isolatable solvates. Compounds of the Disclosure can be present as solvated forms with a pharmaceutically acceptable solvent, such as water, methanol, and ethanol, and it is intended that the disclosure includes both solvated and unsolvated forms of Compounds of the Disclosure.

One type of solvate is a hydrate. A "hydrate" relates to a particular subgroup of solvates where the solvent molecule is water. Solvates typically can function as pharmacological equivalents. Preparation of solvates is known in the art. See, for example, M. Caira et al, *J. Pharmaceut. Sci.,* 93(3):601-611 (2004), which describes the preparation of solvates of fluconazole with ethyl acetate and with water. Similar preparation of solvates, hemisolvates, hydrates, and the like are described by van Tonder et al., *AAPS Pharm. Sci. Tech.,* 5(1): Article 12 (2004), and A. L. Bingham et al., *Chem. Commun.* 603-604 (2001). A typical, non-limiting, process of preparing a solvate would involve dissolving a Compound of the Disclosure in a desired solvent (organic, water, or a mixture thereof) at temperatures above 20° C. to about 25° C., then cooling the solution at a rate sufficient to form crystals, and isolating the crystals by known methods, e.g., filtration. Analytical techniques such as infrared spectroscopy can be used to confirm the presence of the solvent in a crystal of the solvate.

The use of the terms "a", "an", "the", and similar referents in the context of describing the disclosure (especially in the context of the claims) are to be construed to cover both the singular and the plural, unless otherwise indicated. Recitation of ranges of values herein merely are intended to serve as a shorthand method of referring individually to each separate value falling within the range, unless otherwise indicated herein, and each separate value is incorporated into the specification as if it were individually recited herein. The use of any and all examples, or exemplary language (e.g., "such as") provided herein, is intended to better illustrate the disclosure and is not a limitation on the scope of the disclosure unless otherwise claimed. No language in the specification should be construed as indicating any non-claimed element as essential to the practice of the disclosure.

The term "prodrug" as used herein refers to a Compound of the Disclosure that is metabolized, i.e., converted within the body, to produce a pharmacologically active drug, i.e., a branched-chain amino acid. Instead of administering the branched-chain amino acid directly, the corresponding prodrug can be used to improve how the branched-chain amino acid is absorbed, distributed, metabolized, and/or excreted. Prodrugs of the present disclosure may have intrinsic pharmacological activity, or may be pharmacologically inactive. In one embodiment, the prodrugs of the present disclosure have intrinsic pharmacological activity. In another embodiment, the prodrugs of the present disclosure are pharmacologically inactive and thus must be metabolized to produce a pharmacologically active drug.

Pharmaceutical Compositions

In another embodiment, the disclosure provides a pharmaceutical composition comprising a Compound of the Disclosure, or a pharmaceutically acceptable salt or solvate thereof, and a pharmaceutically acceptable carrier and/or excipient.

Compounds of the Disclosure typically are administered in admixture with a pharmaceutical excipient selected with regard to the intended route of administration and standard pharmaceutical practice. Pharmaceutical compositions for use in accordance with the present disclosure are formulated in a conventional manner using one or more physiologically acceptable carriers comprising excipients and/or auxiliaries that facilitate processing of Compounds of the Disclosure.

These pharmaceutical compositions can be manufactured, for example, by conventional mixing, dissolving, granulating, dragee-making, emulsifying, encapsulating, entrapping, or lyophilizing processes. Proper formulation is dependent upon the route of administration chosen. When a therapeutically effective amount of the Compound of the Disclosure is administered orally, the composition typically is in the form of a tablet, capsule, powder, solution, or elixir. When administered in tablet form, the composition additionally can contain a solid carrier, such as a gelatin or an adjuvant. The tablet, capsule, and powder contain about 0.01% to about 95%, e.g., from about 1% to about 50%, of a Compound of the Disclosure. When administered in liquid form, a liquid carrier, such as water, petroleum, or oils of animal or plant origin, can be added. The liquid form of the composition can further contain physiological saline solution, dextrose or other saccharide solutions, or glycols. When administered in liquid form, the composition contains about 0.1% to about 90%, e.g., about 1% to about 50%, by weight, of a Compound of the Disclosure.

When a therapeutically effective amount of a Compound of the Disclosure is administered by intravenous, cutaneous, or subcutaneous injection, the composition is in the form of a pyrogen-free, parenterally acceptable aqueous solution. The preparation of such parenterally acceptable solutions, having due regard to pH, isotonicity, stability, and the like, is within the skill in the art. A composition for intravenous, cutaneous, or subcutaneous injection typically contains an isotonic vehicle.

Compounds of the Disclosure can be readily combined with pharmaceutically acceptable carriers and excipients well-known in the art. Standard pharmaceutical carriers and excipients are described in Remington's Pharmaceutical Sciences, Mack Publishing Co., Easton, PA, 19th ed. 1995. Such carriers enable the active agents to be formulated as tablets, pills, dragees, capsules, liquids, gels, syrups, slurries, suspensions and the like, for oral ingestion by a subject to be treated. Pharmaceutical preparations for oral use can be obtained by adding the Compound of the Disclosure to a solid excipient, optionally grinding the resulting mixture, and processing the mixture of granules, after adding suitable auxiliaries, if desired, to obtain tablets or dragee cores. Suitable excipients include, for example, fillers and cellulose preparations. If desired, disintegrating agents can be added.

Compound of the Disclosure can be formulated for parenteral administration by injection, e.g., by bolus injection or continuous infusion. Formulations for injection can be presented in unit dosage form, e.g., in ampules or in multidose containers, with an added preservative. The compositions can take such forms as suspensions, solutions, or emulsions in oily or aqueous vehicles, and can contain formulatory agents such as suspending, stabilizing, and/or dispersing agents.

Pharmaceutical compositions for parenteral administration include aqueous solutions of the active agent in water-soluble form. Additionally, suspensions of a Compound of the Disclosure can be prepared as appropriate oily injection suspensions. Suitable lipophilic solvents or vehicles include fatty oils or synthetic fatty acid esters. Aqueous injection suspensions can contain substances which increase the viscosity of the suspension. Optionally, the suspension also can contain suitable stabilizers or agents that increase the solubility of the compounds and allow for the preparation of highly concentrated solutions. Alternatively, a present composition can be in powder form for constitution with a suitable vehicle, e.g., sterile pyrogen-free water, before use.

Compounds of the Disclosure also can be formulated in rectal compositions, such as suppositories or retention enemas, e.g., containing conventional suppository bases. In addition to the formulations described previously, the Compound of the Disclosure also can be formulated as a depot preparation. Such long-acting formulations can be administered by implantation (for example, subcutaneously or intramuscularly) or by intramuscular injection. Thus, for example, the Compound of the Disclosure can be formulated with suitable polymeric or hydrophobic materials (for example, as an emulsion in an acceptable oil) or ion exchange resins.

In particular, the Compounds of the Disclosure can be administered orally, buccally, or sublingually in the form of tablets containing excipients, such as starch or lactose, or in capsules or ovules, either alone or in admixture with excipients, or in the form of elixirs or suspensions containing flavoring or coloring agents. Such liquid preparations can be prepared with pharmaceutically acceptable additives, such as suspending agents. Compound of the Disclosure also can be injected parenterally, for example, intravenously, intramuscularly, subcutaneously, or intracoronarily. For parenteral administration, the Compound of the Disclosure are typically used in the form of a sterile aqueous solution which can contain other substances, for example, salts or monosaccharides, such as mannitol or glucose, to make the solution isotonic with blood.

In one embodiment, the pharmaceutically acceptable carrier is a solid, and the composition is in the form of a powder or tablet. A solid pharmaceutically acceptable carrier may include one or more substances which may also act as flavouring agents, buffers, lubricants, stabilisers, solubilisers, suspending agents, wetting agents, emulsifiers, dyes, fillers, glidants, compression aids, inert binders, sweeteners, preservatives, dyes, coatings, or tablet-disintegrating agents. The carrier may also be an encapsulating material. In powders, the carrier is a finely divided solid that is in admixture with the finely divided active agents according to the invention. In tablets, the active agent may be mixed with a carrier having the necessary compression properties in suitable proportions and compacted in the shape and size desired. The powders and tablets may contain up to 99% of the active agents. Suitable solid carriers include, for example, calcium phosphate, magnesium stearate, talc, sugars, lactose, dextrin, starch, gelatin, cellulose, polyvinylpyrrolidine, low melting waxes and ion exchange resins. In another embodiment, the pharmaceutically acceptable carrier may be a gel and the composition may be in the form of a cream or the like.

The carrier may include one or more excipients or diluents. Examples of such excipients are gelatin, gum arabicum, lactose, microcrystalline cellulose, starch, sodium starch glycolate, calcium hydrogen phosphate, magnesium stearate, talcum, colloidal silicon dioxide and the like.

In another embodiment, the pharmaceutically acceptable carrier is a liquid, and the pharmaceutical composition is in the form of a solution. Liquid carriers are used in preparing solutions, suspensions, emulsions, syrups, elixirs and pressurized compositions. A Compound of the Disclosure may be dissolved or suspended in a pharmaceutically acceptable liquid carrier such as water, an organic solvent, a mixture of both or pharmaceutically acceptable oils or fats. The liquid carrier may contain other suitable pharmaceutical additives such as solubilisers, emulsifiers, buffers, preservatives, sweeteners, flavouring agents, suspending agents, thickening agents, colors, viscosity regulators, stabilizers or osmo-regulators. Suitable examples of liquid carriers for oral and parenteral administration include water (partially containing additives as above, e.g. cellulose derivatives, preferably sodium carboxymethyl cellulose solution), alcohols (including monohydric alcohols and polyhydric alcohols, e.g. glycols) and their derivatives, and oils (e.g. fractionated coconut oil and *Arachis* oil). For parenteral administration, the carrier can also be an oily ester such as ethyl oleate and isopropyl myristate. Sterile liquid carriers are useful in sterile liquid form compositions for parenteral administration. The liquid carrier for pressurized compositions can be a halogenated hydrocarbon or other pharmaceutically acceptable propellant.

Liquid pharmaceutical compositions, which are sterile solutions or suspensions, can be utilized by, for example, intramuscular, intrathecal, epidural, intraperitoneal, intravenous and particularly subcutaneous injection. The active agent may be prepared as a sterile solid composition that may be dissolved or suspended at the time of administration using sterile water, saline, or other appropriate sterile injectable medium.

The Compounds of the Disclosure and their compositions may be administered orally in the form of a sterile solution or suspension containing other solutes or suspending agents (for example, enough saline or glucose to make the solution isotonic), bile salts, acacia, gelatin, sorbitan monoleate, polysorbate 80 (oleate esters of sorbitol and its anhydrides copolymerized with ethylene oxide) and the like.

Compounds of the Disclosure and their compositions can also be administered orally either in liquid or solid composition form. Compositions suitable for oral administration include solid forms, such as pills, capsules, granules, tablets, and powders, and liquid forms, such as solutions, syrups, elixirs, and suspensions. Forms useful for parenteral administration include sterile solutions, emulsions, and suspensions.

Compounds of the Disclosure and their compositions may alternatively be administered by inhalation (e.g. intranasally). Compositions may also be formulated for topical use. For instance, creams or ointments may be applied to the skin.

Compounds of the Disclosure and their compositions may be incorporated within a slow- or delayed-release device. Such devices may, for example, be inserted on or under the skin, and the medicament may be released over weeks or even months. Such devices may be particularly advantageous when long-term treatment with a Compound of the Disclosure is required and which would normally require frequent administration (e.g. at least daily administration).

In another embodiment, the pharmaceutical composition is in the form of a tablet suitable for oral administration. In tablets, the Compound of the Disclosure may be mixed with a vehicle having the necessary compression properties in suitable proportions and compacted in the shape and size desired. The tablets may contain up to 99% by weight of the Compound of the Disclosure.

Pharmaceutical formulations in solid oral dosage form, such as tablets, may be prepared by any method known in the art of pharmacy. Pharmaceutical formulations are usually prepared by mixing a Compound of the Disclosure, or a pharmaceutically acceptable salt thereof, with conventional pharmaceutically acceptable carriers, diluents or excipients.

Methods of Use

In another embodiment, the disclosure provides a method of treating or delaying the progression of a lysosomal storage disorder, the method comprising administering to a subject in need thereof a therapeutically effective amount of a Compound of the Disclosure.

In another embodiment, the disclosure provides a method of providing neuroprotection in a subject having a lysosomal storage disorder, the method comprising administering to a subject in need thereof a therapeutically effective amount of a Compound of the Disclosure.

In another embodiment, the disclosure provides a method of treating or delaying the progression of a neurodegenerative disease, the method comprising administering to a subject in need thereof a therapeutically effective amount of a Compound of the Disclosure.

In another embodiment, the disclosure provides a method of treating or delaying the progression of a neurodegenerative disease associated with defects in lysosomal storage, the method comprising administering to a subject in need thereof a therapeutically effective amount of a Compound of the Disclosure.

In another embodiment, the disclosure provides a method of treating or preventing a migraine, and the symptoms associated therewith, the method comprising administering to a subject in need thereof a therapeutically effective amount of a Compound of the Disclosure.

In another aspect, the disclosure provides a method of improving mobility and/or cognitive function, the method comprising administering to a subject in need thereof a therapeutically effective amount of a Compound of the Disclosure.

In another aspect, the disclosure provides a method of treating or preventing restless legs syndrome, the method comprising administering to a subject in need thereof a therapeutically effective amount of a Compound of the Disclosure.

In another aspect, the disclosure provides a method of treating or preventing vertigo, the method comprising administering to a subject in need thereof a therapeutically effective amount of a Compound of the Disclosure.

The disclosure also provides the following particular embodiments.

Embodiment I. A method of treating or delaying the progression of a lysosomal storage disorder, the method comprising administering to a patient in need thereof a therapeutically effective amount of a Compound of the Disclosure having Formula I, see above, or a pharmaceutically acceptable salt or solvate thereof, wherein:

$R^1$ is selected from the group consisting of:

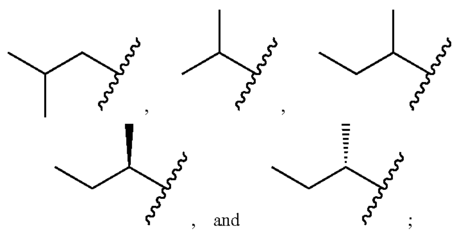

$R^2$ is selected from the group consisting of $C_2$-$C_6$ alkyl and $C_3$-$C_6$ cycloalkyl; and $R^3$ is selected from the group consisting of hydrogen, $C_1$-$C_6$ alkyl, and $C_3$-$C_6$ cycloalkyl.

Embodiment II. A method of providing neuroprotection in a subject having a lysosomal storage disorder, treating or delaying the progression of a neurodegenerative disease, or treating or delaying the progression of a neurodegenerative disease associated with defects in lysosomal storage, treating or preventing a migraine, and the symptoms associated therewith, treating or preventing restless legs syndrome, and the symptoms associated therewith, treating or preventing vertigo, and the symptoms associated therewith, or improving mobility and/or cognitive function, the method comprising administering to a subject in need thereof a therapeutically effective amount of a Compound of the Disclosure having Formula I, see above, or a pharmaceutically acceptable salt or solvate thereof, wherein:

$R^1$ is selected from the group consisting of:

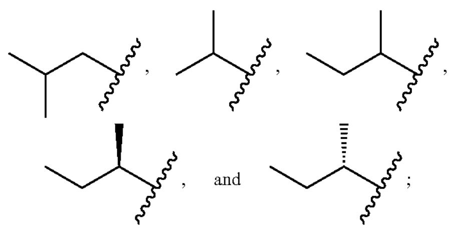

$R^2$ is selected from the group consisting of $C_3$-$C_6$ alkyl and $C_3$-$C_6$ cycloalkyl; and $R^3$ is selected from the group consisting of hydrogen, $C_1$-$C_6$ alkyl, and $C_3$-$C_6$ cycloalkyl.

Embodiment III. The method of Embodiments I or II, wherein the compound having Formula I is optically active.

Embodiment IV. The method of Embodiment III, wherein the optically active compound having Formula I is a compound having Formula II, see above.

Embodiment V. The method of Embodiment III, wherein the optically active compound having Formula I is a compound having Formula III, see above.

Embodiment VI. The method of any one of Embodiments I-V, wherein $R^1$ is:

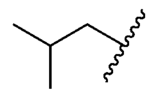

Embodiment VII. The method of any one of Embodiments I-V, wherein $R^1$ is:

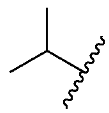

Embodiment VIII. The method of any one of Embodiments I-V, wherein $R^1$ is:

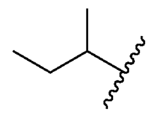

Embodiment IX. The method of any one of Embodiments I-V, wherein $R^1$ is:

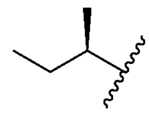

Embodiment X. The method of any one of Embodiments I-V, wherein $R^1$ is:

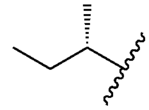

Embodiment XI. The method of any one of Embodiments I-X, wherein $R^2$ is selected from the group consisting of ethyl, propyl, iso-propyl, butyl, iso-butyl, sec-butyl, and tert-butyl.

Embodiment XII. The method of any one of Embodiments I-X, wherein $R^2$ is selected from the group consisting of cyclopropyl, cyclobutyl, cyclopentyl, and cyclohexyl.

Embodiment XIII. The method of any one of Embodiments I-XII, wherein $R^3$ is selected from the group consisting of methyl, ethyl, propyl, iso-propyl, butyl, iso-butyl, sec-butyl, and tert-butyl.

Embodiment XIV. The method of any one of Embodiments I-XII, wherein $R^3$ is selected from the group consisting of cyclopropyl, cyclobutyl, cyclopentyl, and cyclohexyl.

Embodiment XV. The method of any one of Embodiments I-XII, wherein $R^3$ is hydrogen.

Embodiment XVI. The method of any one of Embodiments I-III, wherein $R^1$, $R^2$, and $R^3$ are defined as in Table 1, see above.

Embodiment XVII. The method of Embodiment IV, wherein $R^1$, $R^2$, and $R^3$ are defined as in Table 2, see above.

Embodiment XVIII. The method of Embodiment V, wherein $R^1$, $R^2$, and $R^3$ are defined as in Table 3, see above.

Embodiment XIX. A Compound of the Disclosure having Formula I, see above, or a pharmaceutically acceptable salt or solvate thereof, wherein:

$R^1$ is selected from the group consisting of:

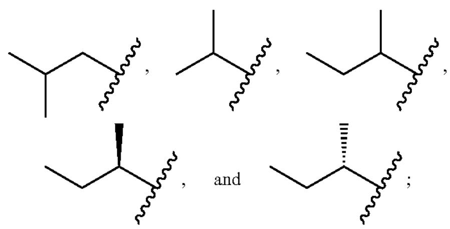

$R^2$ is selected from the group consisting of $C_2$-$C_6$ alkyl and $C_3$-$C_6$ cycloalkyl; and $R^3$ is selected from the group consisting of hydrogen, $C_1$-$C_6$ alkyl, and $C_3$-$C_6$ cycloalkyl, for use in a method of treating or delaying progression of a lysosomal storage disorder.

Embodiment XX. A Compound of the Disclosure having Formula I, see above, or a pharmaceutically acceptable salt or solvate thereof, wherein:

$R^1$ is selected from the group consisting of:

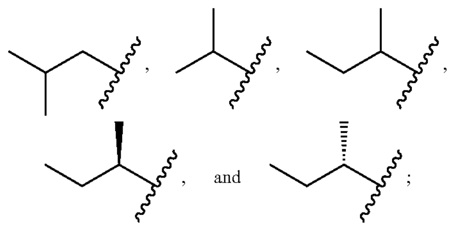

$R^2$ is selected from the group consisting of $C_2$-$C_6$ alkyl and $C_3$-$C_6$ cycloalkyl; and $R^3$ is selected from the group consisting of hydrogen, $C_1$-$C_6$ alkyl, and $C_3$-$C_6$ cycloalkyl, for use in providing neuroprotection in a subject having a lysosomal storage disorder, treating or delaying the progression of a neurodegenerative disease, or treating or delaying the progression of a neurodegenerative disease associated with defects in lysosomal storage, treating or preventing a migraine, and the symptoms associated therewith, treating or preventing restless legs syndrome, and the symptoms associated therewith, treating or preventing vertigo, and the symptoms associated therewith, or improving mobility and/or cognitive function.

Embodiment XXI. The compound for use of Embodiments XIX or XX, wherein the compound having Formula I is optically active.

Embodiment XXII. The compound for use of Embodiment XXI, wherein the optically active compound having Formula I is a compound having Formula II, see above.

Embodiment XXIII. The compound for use of Embodiment XXI, wherein the optically active compound having Formula I is a compound having Formula III, see above.

Embodiment XXIV. The compound for use of any one of Embodiments XIX-XXIII, wherein $R^1$ is:

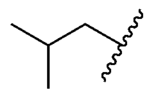

Embodiment XXV. The compound for use of any one of Embodiments XIX-XXIII, wherein $R^1$ is:

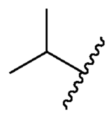

Embodiment XXVI. The compound for use of any one of Embodiments XIX-XXIII, wherein $R^1$ is:

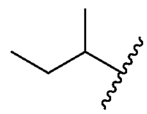

Embodiment XXVII. The compound for use of any one of Embodiments XIX-XXIII, wherein $R^1$ is:

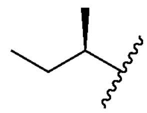

Embodiment XXVIII. The compound for use of any one of Embodiments XIX-XXIII, wherein $R^1$ is:

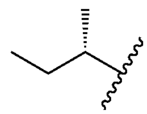

Embodiment XXIX. The compound for use of any one of Embodiments XIX-XXVIII, wherein $R^2$ is selected from the group consisting of ethyl, propyl, iso-propyl, butyl, iso-butyl, sec-butyl, and tert-butyl.

Embodiment XXX. The compound for use of any one of Embodiments XIX-XXVIII, wherein $R^2$ is selected from the group consisting of cyclopropyl, cyclobutyl, cyclopentyl, and cyclohexyl.

Embodiment XXXI. The compound for use of any one of Embodiments XIX-XXX, wherein $R^3$ is selected from the group consisting of methyl, ethyl, propyl, isopropyl, butyl, iso-butyl, sec-butyl, and tert-butyl.

Embodiment XXXII. The compound for use of any one of Embodiments XIX-XXX, wherein $R^3$ is selected from the group consisting of cyclopropyl, cyclobutyl, cyclopentyl, and cyclohexyl.

Embodiment XXXIII. The compound for use of any one of Embodiments XIX-XXX, wherein $R^3$ is hydrogen.

Embodiment XXXIV. The compound for use of any one of Embodiments XIX-XXI, wherein $R^1$, $R^2$, and $R^3$ are defined as in Table 1, see above.

Embodiment XXXV. The compound for use of Embodiment XXII, wherein $R^1$, $R^2$, and $R^3$ are defined as in Table 2, see above.

Embodiment XXXVI. The compound for use of Embodiment XXIII, wherein $R^1$, $R^2$, and $R^3$ are defined as in Table 3, see above.

Embodiment XXXVII. A Compound of the Disclosure having Formula I, see above, or a pharmaceutically acceptable salt or solvate thereof, wherein:

$R^1$ is selected from the group consisting of.

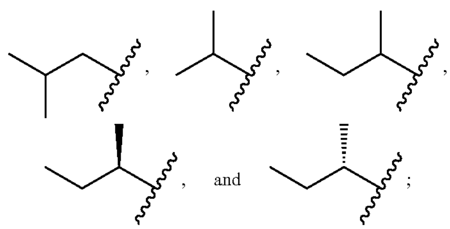

$R^2$ is selected from the group consisting of $C_2$-$C_6$ alkyl and $C_3$-$C_6$ cycloalkyl; and $R^3$ is selected from the group consisting of hydrogen, $C_1$-$C_6$ alkyl, and $C_3$-$C_6$ cycloalkyl, for use in manufacture of a medicament for treating or delaying progression of a lysosomal storage disorder.

Embodiment XXXVIII. A Compound of the Disclosure having Formula I, see above, or a pharmaceutically acceptable salt or solvate thereof, wherein:

$R^1$ is selected from the group consisting of:

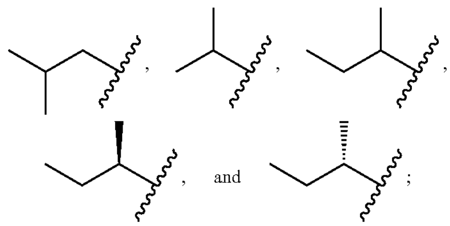

$R^2$ is selected from the group consisting of $C_2$-$C_6$ alkyl and $C_3$-$C_6$ cycloalkyl; and $R^3$ is selected from the group consisting of hydrogen, $C_1$-$C_6$ alkyl, and $C_3$-$C_6$ cycloalkyl, for use in manufacture of a medicament for providing neuroprotection in a subject having a lysosomal storage disorder, treating or delaying the progression of a neurodegenerative disease, or treating or delaying the progression of a neurodegenerative disease associated with defects in lysosomal storage, treating or preventing a migraine, and the symptoms associated therewith, treating or preventing restless legs syndrome, and the symptoms associated therewith, treating or preventing vertigo, and the symptoms associated therewith, or improving mobility and/or cognitive function.

Embodiment XXXIX. The use of Embodiments XXXVII or XXXVIII, wherein the compound having Formula I is optically active.

Embodiment XL. The use of Embodiment XXXIX, wherein the optically active compound having Formula I is a compound having Formula II, see above.

Embodiment XLI. The use of Embodiment XXXIX, wherein the optically active compound having Formula I is a compound having Formula III, see above.

Embodiment XLII. The use of any one of Embodiments XXXVII-XLI, wherein $R^1$ is:

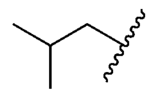

Embodiment XLIII. The use of any one of Embodiments XXXVII-XLI, wherein $R^1$ is:

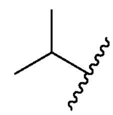

Embodiment XLIV. The use of any one of Embodiments XXXVII-XLI, wherein $R^1$ is:

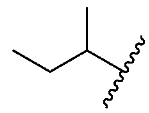

Embodiment XLV. The use of any one of Embodiments XXXVII-XLI, wherein $R^1$ is:

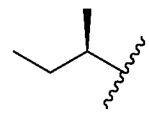

Embodiment XLVI. The use of any one of Embodiments XXXVII-XLI, wherein $R^1$ is:

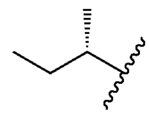 [SMILES: *[C@@H](C)CC]

Embodiment XLVII. The use of any one of Embodiments XXXVII-XLVI, wherein $R^2$ is selected from the group consisting of ethyl, propyl, iso-propyl, butyl, iso-butyl, sec-butyl, and tert-butyl.

Embodiment XLVIII. The use of any one of Embodiments XXXVII-XLVI, wherein $R^2$ is selected from the group consisting of cyclopropyl, cyclobutyl, cyclopentyl, and cyclohexyl.

Embodiment XLIX. The use of any one of Embodiments XXXVII-XLVIII, wherein $R^3$ is selected from the group consisting of methyl, ethyl, propyl, iso-propyl, butyl, iso-butyl, sec-butyl, and tert-butyl.

Embodiment L. The use of any one of Embodiments XXXVII-XLVIII, wherein $R^3$ is selected from the group consisting of cyclopropyl, cyclobutyl, cyclopentyl, and cyclohexyl.

Embodiment LI. The use of any one of Embodiments XXXVII-XLVIII, wherein $R^3$ is hydrogen.

Embodiment LII. The use of any one of Embodiments XXXVII-XXXIX, wherein $R^1$, $R^2$, and $R^3$ are defined as in Table 1, see above.

Embodiment LIII. The use of Embodiment XL, wherein $R^1$, $R^2$, and $R^3$ are defined as in Table 2, see above.

Embodiment LIV. The use of Embodiment XLI, wherein $R^1$, $R^2$, and $R^3$ are defined as in Table 3, see above.

Embodiment LV. A pharmaceutical composition comprising a Compound of the Disclosure having Formula I, see above, or a pharmaceutically acceptable salt or solvate thereof, wherein:

$R^1$ is selected from the group consisting of:

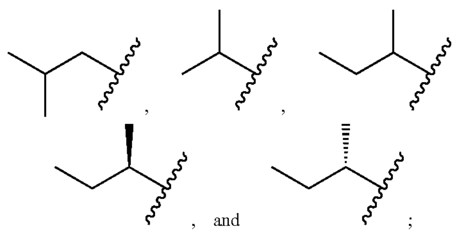

, , , , and ;

$R^2$ is selected from the group consisting of $C_3$-$C_6$ alkyl and $C_3$-$C_6$ cycloalkyl; and $R^3$ is selected from the group consisting of hydrogen, $C_1$-$C_6$ alkyl, and $C_3$-$C_6$ cycloalkyl, for use in a method of treating or delaying progression of a lysosomal storage disorder.

Embodiment LVI. A pharmaceutical composition comprising a Compound of the Disclosure having Formula I, see above, or a pharmaceutically acceptable salt or solvate thereof, wherein:

$R^1$ is selected from the group consisting of:

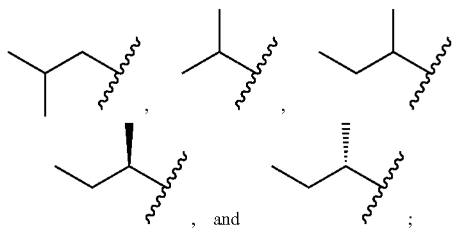

, , , , and ;

$R^2$ is selected from the group consisting of $C_2$-$C_6$ alkyl and $C_3$-$C_6$ cycloalkyl; and $R^3$ is selected from the group consisting of hydrogen, $C_1$-$C_6$ alkyl, and $C_3$-$C_6$ cycloalkyl, for use in providing neuroprotection in a subject having a lysosomal storage disorder, treating or delaying the progression of a neurodegenerative disease, or treating or delaying the progression of a neurodegenerative disease associated with defects in lysosomal storage, treating or preventing a migraine, and the symptoms associated therewith, treating or preventing restless legs syndrome, and the symptoms associated therewith, treating or preventing vertigo, and the symptoms associated therewith, or improving mobility and/or cognitive function.

Embodiment LVII. The pharmaceutical composition of Embodiments LV or LVI, wherein the compound having Formula I is optically active.

Embodiment LVIII. The pharmaceutical composition of Embodiment LVII, wherein the optically active compound having Formula I is a compound having Formula II, see above.

Embodiment LIX. The pharmaceutical composition of Embodiment LVII, wherein the optically active compound having Formula I is a compound having Formula III, see above.

Embodiment LX. The pharmaceutical composition of any one of Embodiments LV-LIX, wherein $R^1$ is:

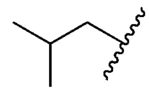

.

Embodiment LXI. The pharmaceutical composition of any one of Embodiments LV-LIX, wherein $R^1$ is:

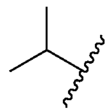

.

Embodiment LXII. The pharmaceutical composition of any one of Embodiments LV-LIX, wherein $R^1$ is:

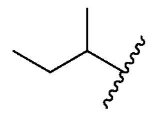

.

Embodiment LXIII. The pharmaceutical composition of any one of Embodiments LV-LIX, wherein $R^1$ is:

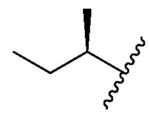

.

Embodiment LXIV. The pharmaceutical composition of any one of Embodiments LV-LIX, wherein $R^1$ is:

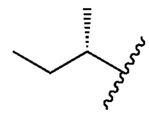

.

Embodiment LXV. The pharmaceutical composition of any one of Embodiments LV-LXIV, wherein $R^2$ is selected from the group consisting of ethyl, propyl, iso-propyl, butyl, iso-butyl, sec-butyl, and tert-butyl.

Embodiment LXVI. The pharmaceutical composition of any one of Embodiments LV-LXIV, wherein $R^2$ is selected from the group consisting of cyclopropyl, cyclobutyl, cyclopentyl, and cyclohexyl.

Embodiment LXVII. The pharmaceutical composition of any one of Embodiments LV-LXVI, wherein $R^3$ is selected from the group consisting of methyl, ethyl, propyl, iso-propyl, butyl, iso-butyl, sec-butyl, and tert-butyl.

Embodiment LXVIII. The pharmaceutical composition of any one of Embodiments LV-LXVI, wherein $R^3$ is selected from the group consisting of cyclopropyl, cyclobutyl, cyclopentyl, and cyclohexyl.

Embodiment LXIX. The pharmaceutical composition of any one of Embodiments LV-LXVI, wherein $R^3$ is hydrogen.

Embodiment LXX. The pharmaceutical composition of any one of Embodiments LV-LVII, wherein $R^1$, $R^2$, and $R^3$ are defined as in Table 1, see above.

Embodiment LXXI. The pharmaceutical composition of Embodiment LVIII, wherein $R^1$, $R^2$, and $R^3$ are defined as in Table 2, see above.

Embodiment LXXII. The pharmaceutical composition of Embodiment LIX, wherein $R^1$, $R^2$, and $R^3$ are defined as in Table 3, see above.

Embodiment LXXIII. A kit comprising a Compound of the Disclosure having Formula I, see above, or a pharmaceutically acceptable salt or solvate thereof, wherein:

$R^1$ is selected from the group consisting of:

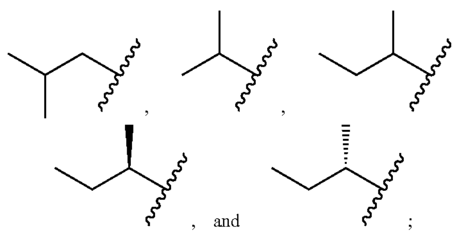

, , , and ;

$R^2$ is selected from the group consisting of $C_2$-$C_6$ alkyl and $C_3$-$C_6$ cycloalkyl; and $R^3$ is selected from the group consisting of hydrogen, $C_1$-$C_6$ alkyl, and $C_3$-$C_6$ cycloalkyl, and instructions for administering the compound to a subject to treat or delay progression of a lysosomal storage disorder, or for providing neuroprotection in a subject having a lysosomal storage disorder, or treat or delay the progression of a neurodegenerative disease, treating or delaying the progression of a neurodegenerative disease associated with defects in lysosomal storage, treating or preventing a migraine, and the symptoms associated therewith, treating or preventing restless legs syndrome, and the symptoms associated therewith, treating or preventing vertigo, and the symptoms associated therewith, or improving mobility and/or cognitive function.

Embodiment LXXIV. The kit of Embodiment LXXIII, wherein the compound having Formula I is optically active.

Embodiment LXXV. The kit of Embodiment LXXIV, wherein the optically active compound having Formula I is a compound having Formula II, see above.

Embodiment LXXVI. The kit of Embodiment LXXIV, wherein the optically active compound having Formula I is a compound having Formula III, see above.

Embodiment LXXVII. The kit of any one of Embodiments LXXIII-LXXVI, wherein $R^1$ is:

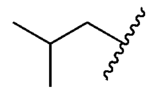

.

Embodiment LXXVIII. The kit of any one of Embodiments LXXIII-LXXVI, wherein $R^1$ is:

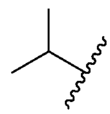

.

Embodiment LXXIX. The kit of any one of Embodiments LXXIII-LXXVI, wherein $R^1$ is:

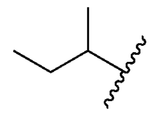

.

Embodiment LXXX. The kit of any one of Embodiments LXXIII-LXXVI, wherein $R^1$ is:

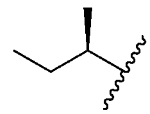

.

Embodiment LXXXI. The kit of any one of Embodiments LXXIII-LXXVI, wherein $R^1$ is:

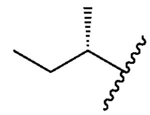

.

Embodiment LXXXII. The kit of any one of Embodiments LXXIII-LXXXI, wherein $R^2$ is selected from the group consisting of ethyl, propyl, iso-propyl, butyl, iso-butyl, sec-butyl, and tert-butyl.

Embodiment LXXXIII. The kit of any one of Embodiments LXXIII-LXXXI, wherein $R^2$ is selected from the group consisting of cyclopropyl, cyclobutyl, cyclopentyl, and cyclohexyl.

Embodiment LXXXIV. The kit of any one of Embodiments LXXIII-LXXXIII, wherein $R^3$ is selected from the group consisting of methyl, ethyl, propyl, iso-propyl, butyl, iso-butyl, sec-butyl, and tert-butyl.

Embodiment LXXXV. The kit of any one of Embodiments LXXIII-LXXXIII, wherein $R^3$ is selected from the group consisting of cyclopropyl, cyclobutyl, cyclopentyl, and cyclohexyl.

Embodiment LXXXVI. The kit of any one of Embodiments LXXIII-LXXXIII, wherein $R^3$ is hydrogen.

Embodiment LXXXVIII. The kit of Embodiment LXXIII or LXXIV, wherein $R^1$, $R^2$, and $R^3$ are defined as in Table 1, see above.

Embodiment LXXXIX. The kit of Embodiment LXXV, wherein $R^1$, $R^2$, and $R^3$ are defined as in Table 2, see above.

Embodiment XC. The kit of Embodiment LXXVII, wherein $R^1$, $R^2$, and $R^3$ are defined as in Table 3, see above.

In another embodiment, a Compound of the Disclosure is administered in combination with a second therapeutic agent useful in the treatment of a LSD, a neurodegenerative disease, or a migraine, restless legs syndrome, or vertigo, or useful for improving mobility and/or cognitive function. The second therapeutic agent is different from the Compound of the Disclosure. A Compound of the Disclosure and the second therapeutic agent can be administered simultaneously or sequentially to achieve the desired effect. In addition, the Compound of the Disclosure and second therapeutic agent can be administered from a single composition or two separate compositions.

The second therapeutic agent is administered in an amount to provide its desired therapeutic effect. The effective dosage range for each second therapeutic agent is typically known in the art, and the second therapeutic agent is administered to a subject in need thereof within such established ranges.

A Compound of the Disclosure and the second therapeutic agent can be administered together as a single-unit dose or separately as multi-unit doses, wherein the Compound of the Disclosure is administered before the second therapeutic agent or vice versa. One or more doses of the Compound of the Disclosure and/or one or more dose of the second therapeutic agent can be administered.

The term "subject" as used herein may be a vertebrate, mammal, or domestic animal. Hence, compositions according to the disclosure may be used to treat any mammal, for example livestock, e.g. a horse, cow, sheep or pig, pets, e.g. a cat, dog, rabbit or guinea pig, a laboratory animal, e.g. a mouse or rat, or may be used in other veterinary applications. In one embodiment, the subject is a human being.

The terms "treat," "treating," "treatment," and the like as used herein, unless otherwise indicated, refer to eliminating, reducing, or ameliorating a disease or condition, and/or symptoms associated therewith. Although not precluded, treating a disease or condition does not require that the disease, condition, or symptoms associated therewith be completely eliminated. The term "treat" and synonyms contemplate administering a therapeutically effective amount of a Compound of the Disclosure to a subject in need of such treatment. The treatment can be orientated symptomatically, for example, to suppress symptoms. It can be effected over a short period, be oriented over a medium term, or can be a long-term treatment, for example within the context of a maintenance therapy.

The terms "prevent," "preventing," and "prevention" as used herein refer to a method of preventing the onset of a disease or condition and/or its attendant symptoms or barring a subject from acquiring a disease. As used herein, "prevent," "preventing," and "prevention" also include delaying the onset of a disease and/or its attendant symptoms and reducing a subject's risk of acquiring a disease. The terms "prevent," "preventing" and "prevention" may include "prophylactic treatment," which refers to reducing the probability of redeveloping a disease or condition, or of a recurrence of a previously-controlled disease or condition, in a subject who does not have, but is at risk of or is susceptible to, redeveloping a disease or condition or a recurrence of the disease or condition.

The term "therapeutically effective amount" or "effective dose" as used herein refers to an amount of a Compound of the Disclosure that is sufficient, when administered by a method of the disclosure, to deliver the compound for the treatment of the condition or disease of interest to a subject in need thereof, and produces a desired effect in the subject. In the case of a LSD or a neurodegenerative disease, the therapeutically effective amount of a Compound of the Disclosure may, e.g., delay the time to appearance of a symptom of a LSD or a mark associated with a LSD or delay the time to appearance of a symptom of a neurodegenerative disease.

The term "lysosomal storage disorder" or "LSD" as used herein refers to any disorder that involves dysfunction or disruption in the late endosomal/lysosomal system. A LSD may involve an increased volume and/or pH of the endosomal/lysosomal system. A LSD may also involve increased storage of lipid or non-lipids.

The LSD may be a primary lysosomal hydrolase defect, a post-translational processing defect of lysosomal enzymes, a trafficking defect for lysosomal enzymes, a defect in lysosomal enzyme protection, a defect in soluble non-enzymatic lysosomal proteins, a transmembrane (non-enzyme) protein defect or an unclassified defect.

Primary lysosomal hydrolase defects include, but are not limited to, Gaucher disease (glucosylceramidase defect), GM1 gangliosidosis (GM1-β-galactosidase defect), Tay-Sachs disease (β-hexosaminidase A defect), Sandhoff disease (β-hexosaminidase A+B defect), Fabry disease (α-galactosidase A defect), Krabbe disease (β-galactosyl ceramidase defect), Niemann-Pick Type A and B (sphingomyelinase defect), metachromatic leukodystrophy (arylsulphatase A defect), MPS IH (Hurler syndrome; α-iduronidase defect), MPS IS (Scheie syndrome; α-iduronidase defect), MPS IH-S(Hurler-Scheie syndrome; α-iduronidase defect), MPS II (Hunter syndrome; iduronate sulphatase defect), MPS IIIA (Sanfilippo A syndrome; heparan sulphamidase defect), MPS IIIB (Sanfilippo B syndrome; acetyl α-glucosaminidase defect), MPS IIIC (Sanfilippo C syndrome; acetyl CoA: α-glucosaminide N-acetyltransferase defect), MPS IIID (Sanfilippo D syndrome; N-acetyl glucosamine-6-sulphatase defect), MPS IV A (Morquio A disease; acetyl galactosamine-6-sulphatase defect), MPS IVB (Morquio B disease; β-galactosidase defect), MPS V (redesignated MPS IS), MPS VI (Maroteaux Lamy Syndrome; acetyl galactosamine-4-sulphatase (arylsulphatase B) defect), MPS VII (Sly Syndrome; β-glucuronidase defect), MPS IX (hyaluronidase defect), Wolman disease (WD; acid lipase defect), Farber disease (acid ceramidase defect), cholesteryl ester storage disease (acid lipase defect), Pompe disease (Type II; a 1,4-glucosidase defect), aspartylglucosaminuria (glycosylasparaginase defect), fucosidosis (α-fucosidase defect), α-mannosidosis (α-mannosidase defect), β-mannosidosis (β-mannosidase defect), Schindler disease (N-acetylgalactosaminidase defect), sialidosis (α-neuraminidase defect), infantile neuronal ceroid lipofuscinoses (CLN1; palmitoyl protein thioesterase defect), late infantile neuronal ceroid lipofuscinoses (CLN2; carboxypeptidase defect), early infantile GM1 gangliosidosis, late infantile GM1 gangliosidosis, adult infantile GM1 gangliosidosis, Gaucher Disease Type 1 (Non-Neuronopathic), Gaucher Disease Type 2/3 (Neuronopathic), ML1 (MLI; Sialidosis, alpha-N-acetyl neuraminidase (sialidase) deficiency, ML2 (MLII, I-cell disease; N-acetyl glucosamine phosphoryl transferase defect) ML3 (MLIII, pseudo-Hurler polydystrophy; N-acetyl glucosamine phosphoryl transferase defect), ML4 (MLIV, Mucolipin 1 deficiency), Neuronal Ceroid Lipofuscinoses Type 4 (CLN4; Kufs disease; Adult NCL; palmotoyl-protein thioesterase-1 deficiency (Type A); Cathepsin F deficiency (Type B)), Neuronal Ceroid Lipofuscinoses Type 8—Northern Epilepsy (CLN8), Neuronal Ceroid Lipofuscinoses Type 8—Turkish Late Infantile (CLN8), Neuronal Ceroid Lipofuscinoses Type 9—German/Serbian Late Infantile (CLN9), Neuronal Ceroid Lipofuscinoses Type 10 (CLN10; Congenital Cathepsin D Deficiency), Pycnodysostosis (Cathepsin K defect), Infantile-Onset Pompe Disease, Late-Onset Pompe Disease, and Cholesteryl Ester Storage Disease.

Post-translational processing defects of lysosomal enzymes include, but are not limited to, mucosulphatidosis (MSD; multiple sulphatase defect).

Trafficking defects for lysosomal enzymes include, but are not limited to, mucolipidosis type II (I-cell disease; N-acetyl glucosamine phosphoryl transferase defect), mucolipidosis type IDA (pseudo-Hurler polydystrophy; N-acetyl glucosamine phosphoryl transferase defect) and mucolipidosis type IIIC.

Defects in lysosomal enzyme protection include, but are not limited to, galactosialidosis (protective protein cathepsin A (PPCA) defect), β-galactosidase defects and neuraminidase defects. Defects in soluble non-enzymatic lysosomal proteins include, but are not limited to, GM2 activator protein deficiency (variant AB), sphingolipid activator protein (SAP) deficiency and neuronal ceroid lipofuscinoses (NCL) (CLN5).

Transmembrane (non-enzyme) protein defects include, but are not limited to, Danon disease (lysosome-associated membrane protein 2 (LAMP2) defect), NPC (NPC1 and/or NPC2 defect), cystinosis (cystinosin defect), infantile free sialic acid storage disease (ISSD; sialin defect), Salla disease (free sialic acid storage; sialin defect), juvenile neuronal ceroid lipofuscinoses (CLN3, Batten disease), neuronal ceroid lipofuscinoses (NCL) (CLN6 and CLN8) and mucolipidosis type IV (mucolipin defect).

Unclassified defects include, but are not limited to, neuronal ceroid lipofuscinoses (NCL) (CLN4 and CLN7).

The LSD to be treated, delayed, or ameliorated by the compounds, compositions, and methods of the disclosure is any of NPC (NPC1 and/or NPC2 defect, primary or secondary), Smith-Lemli-Opitz Syndrome (SLOS), an inborn error of cholesterol synthesis, Tangier disease, Pelizaeus-Merzbacher disease, the neuronal ceroid lipofuscinoses, primary glycosphingolipidoses (i.e. Gaucher, Fabry, GM1, GM2 gangliosidoses, Krabbe and metachromatic leukodystrophy (MLD)), Farber disease and multiple sulphatase deficiency.

In some embodiments, LSDs having a significant central nervous system (CNS) involvement, such as NPC, Tay-Sachs disease, Sandhoff disease, GM1 gangliosidosis or Fabry disease are treated or delayed by Compounds of the Disclosure and the compositions and methods described herein.

Niemann-Pick diseases are a heterogeneous group of autosomal recessive LSDs. Common cellular features include abnormal sphingomyelin (SM) storage in mononuclear phagocytic cells and parenchymal tissues, as well as (hepato)splenomegaly. Among the three main subgroups (A-C), NPC (previously classified as NPC and NPD and now appreciated to be a single disease) is classified as a fatal neurovisceral LSD caused by abnormal intracellular cholesterol transport-induced accumulation of unesterified cholesterol in late endosome/lysosomal compartments.

Outside the CNS, the cellular characteristics of NPC include abnormal accumulation of unesterified cholesterol and other lipids (e.g. GSLs) within late endosome/lysosomal compartments. Conversely, there is no net elevation in cholesterol in the CNS (although it does have an altered distribution) but there are highly elevated levels of GSLs. Progressive neurodegeneration is particularly characterized by sequential degeneration of GABAergic Purkinje neurons in the cerebellum, which parallels the onset and progression of cerebellar ataxia and other aspects of neurological dysfunctions seen during the course of NPC. Genetic studies have shown that NPC disease is caused by mutations in either the Npc1 or Npc2 genes. The precise mechanistic link between these two genes remains unknown and the functional roles of these proteins remains enigmatic. NPC1 encodes a multimembrane spanning protein of the limiting membrane of the late endosome/lysosome, whereas NPC2 is a soluble cholesterol binding protein of the lysosome. When NPC1 is inactivated, sphingosine is the first lipid to be stored, suggesting that NPC1 plays a role in the transport of sphingosine from the lysosome, where it is normally generated as part of sphingolipid catabolism. Elevated sphingosine in turn causes a defect in calcium entry into acidic stores resulting in greatly reduced calcium release from this compartment. This then prevents late endosome-lysosome fusion, which is a calcium dependent process, and causes the secondary accumulation of lipids (cholesterol, sphingomyelin and glycosphingolipids) that are cargos in transit through the late endocytic pathway.

Other secondary consequences of inhibiting NPC1 function include defective endocytosis and failure to clear autophagic vacuoles. It has been shown that the NPC1/NPC2 cellular pathway is targeted by pathogenic mycobacteria to promote their survival in late endosomes. In one embodiment, the Niemann-Pick disease is a Niemann-Pick type A, B, C1 or C2 disease.

Tay-Sachs disease is a fatal hereditary disorder of lipid metabolism characterized especially in CNS tissue due to deficiency of the A (acidic) isozyme of β-hexosaminidase. Mutations in the HEXA gene, which encodes the a subunit of β-hexosaminidase, cause the A isozyme deficiency. Tay-Sachs is a prototype of a group of disorders, the GM2 gangliosidoses, characterized by defective GM2 ganglioside degradation. The GM2 ganglioside (monosialylated ganglioside 2) accumulates in the neurons beginning already in fetal life. In one embodiment, the Tay-Sachs disease is the Tay-Sachs AB variant.

Sandhoff disease results from a deficiency of both the A and B (basic) isozymes of β-hexosaminidase. Mutations in the HEXB gene, which encodes the β subunit of β-hexosaminidase, cause the B isozyme deficiency.

GM1 gangliosidosis is caused by a deficiency of β-galactosidase, which results in lysosomal storage of GM1 ganglioside (monosialylated ganglioside 1).

Fabry disease is caused by a deficiency of α-galactosidase, which results in lysosomal storage of a ceramide trihexoside.

The term “neurodegenerative disease”, as used herein, refers to any disorder that affects neurons and involves the progressive loss of neuronal structure, the progressive loss of neuronal function, or progressive neuron cell death.

Neurodegenerative diseases include, but are not limited to, alcoholism, Alexander's disease, Alper's disease, Alzheimer's Disease, amyotrophic lateral sclerosis (ALS), ataxia telangiectasia, neuronal ceroid lipofuscinoses, Batten disease, bovine spongiform encephalopathy (BSE), Canavan disease, cerebral palsy, Cockayne syndrome, corticobasal degeneration, Creutzfeldt-Jakob disease, frontotemporal lobar degeneration, Gaucher's disease, Huntington's disease, HIV-associated dementia, Kennedy's disease, Krabbe's disease, Lewy body dementia, lysosomal storage disorders, neuroborreliosis, Machado-Joseph disease, multiple system atrophy, multiple sclerosis, multiple sulfatase deficiency, mucolipidoses, narcolepsy, Niemann-Pick type C, Niemann Pick disease, Parkinson's Disease, lower body Parkinson's syndrome, Pelizaeus-Merzbacher Disease, Pick's disease, Pompe disease, primary lateral sclerosis, prion diseases, progressive supranuclear palsy, Refsum's disease, Sandhoff disease, Schilder's disease, subacute combined degeneration of spinal cord secondary to pernicious anaemia, Spielmeyer-Vogt-Sjogren-Ba 5 tten disease, cerebellar ataxia, spinocerebellar ataxia, spinal muscular atrophy, Steele-Richardson-Olszewski disease, Tabes *dorsalis*, Tay-Sachs disease, dentatorubral-pallidoluysian atrophy, Episodic Ataxia (EA) 1, Episodic Ataxia (EA) 2, Episodic Ataxia (EA) 3, Episodic Ataxia (EA) 4, Episodic Ataxia (EA) 5, Episodic Ataxia (EA) 6, Episodic Ataxia (EA) 7, Autosomal Recessive Spastic Ataxia of Charlevoix-Saguenay (ARSACS), Autosomal Recessive Cerebellar Ataxia Type 1 (Recessive Ataxia of Beauce (RAB)), Autosomal Recessive Cerebellar Ataxia Type 2 (spinocerebellar ataxia autosomal recessive 9, SCAR9), Ataxia with Oculomotor Apraxia Type 1 (AOA1), Ataxia with Oculomotor Apraxia Type 2 (AOA2), Ataxia with Vitamin E Deficiency (AVED), Freidreich's Ataxia (FRDA), mitochondrial recessive ataxia syndrome (MIRAS), Myclonic Epilepsy Myopathy Sensory Ataxia (MEMSA), Sensory Ataxic Neuropathy Dysarthria Opthalmoparesis (SANDO), ataxia with coenzyme Q10 deficiency, mitochondrial myopathy, encephalopathy, lactacidosis, stroke syndrome (MELAS), myoclonic epilepsy with ragged red fibers (MERRF), neurogenic muscle weakness, ataxia, and retinitis pigmentosa (NARP), Kearns-Sayre (KSS), Fragile X tremor/ataxia syndrome (FXTAS), Arts Syndrome, Christianson type X-linked syndromic mental retardation, X-linked sideroblastic anemia, Idiopathic Late-Onset Cerebellar Ataxia, Sporadic Adult-Onset Ataxia of Unknown Etiology (SAOA), transmissible mink encephalopathy, chronic wasting disease, feline spongiform encephalopathy, exotic ungulate encephalopathy, Kuru, variant Creutzfeldt-Jakob disease, Gerstmann-Straussler-Scheinker syndrome, fatal familial insomnia, hereditary motor and sensory neuropathy with proximal dominance, Wobbly Hedgehog Syndrome (WHS), progressive muscular atrophy (Duchenne-Aran muscular atrophy), progressive bulbar palsy, pseudobulbar palsy, HIV-associated neurocognitive disorders (HAND), parkinsonism, and scrapie.

In one embodiment, the spinocerebellar ataxia is infantile-onset spinocerebellar ataxia, Spinocerebellar Ataxia (SCA) 1, Spinocerebellar Ataxia (SCA) 2, Spinocerebellar Ataxia (SCA) 3 (Machado-Joseph disease), Spinocerebellar Ataxia (SCA) 4, Spinocerebellar Ataxia (SCA) 5 (Lincoln's Ataxia), Spinocerebellar Ataxia (SCA) 6, Spinocerebellar Ataxia (SCA) 7, Spinocerebellar Ataxia (SCA) 8, Spinocerebellar Ataxia (SCA) 10, Spinocerebellar Ataxia (SCA) 11, Spinocerebellar Ataxia (SCA) 12, Spinocerebellar Ataxia (SCA) 13, Spinocerebellar Ataxia (SCA) 14, Spinocerebellar Ataxia (SCA) 15/16, Spinocerebellar Ataxia (SCA) 17, Spinocerebellar Ataxia (SCA) 18 (sensory/motor neuropathy with ataxia), Spinocerebellar Ataxia (SCA) 19/22, Spinocerebellar Ataxia (SCA) 20, Spinocerebellar Ataxia (SCA) 21, Spinocerebellar Ataxia (SCA) 23, Spinocerebellar 5 Ataxia (SCA) 24, Spinocerebellar Ataxia (SCA) 25, Spinocerebellar Ataxia (SCA) 26, Spinocerebellar Ataxia (SCA) 27, Spinocerebellar Ataxia (SCA) 28 (spinocerebellar ataxia autosomal recessive type 4 (SCAR4); Spinocerebellar ataxia with saccadic intrusions), Spinocerebellar Ataxia (SCA) 29, Spinocerebellar Ataxia (SCA) 30, Spinocerebellar Ataxia (SCA) 31, Spinocerebellar Ataxia (SCA) 32, Spinocerebellar Ataxia (SCA) 35, Spinocerebellar Ataxia (SCA) 36, X-linked Spinocerebellar Ataxia 1, X-linked Spinocerebellar Ataxia 2, X-linked Spinocerebellar Ataxia 3, X-linked Spinocerebellar Ataxia 4 or X-linked Spinocerebellar Ataxia 5.

In one embodiment, the neurodegenerative disease is cerebellar ataxia. In one embodiment, the neurodegenerative disease is Niemann Pick disease. In one embodiment, the neurodegenerative disease is parkinsonism. In one embodiment, the neurodegenerative disease is neuronopathic Gaucher disease. In one embodiment, the neurodegenerative disease is Sandhoff's disease. In one embodiment, the neurodegenerative disease is Louis-Barr syndrome. In one embodiment, the neurodegenerative disease is Alzheimer's disease. In one embodiment, the neurodegenerative disease is Parkinson's disease. In one embodiment, the neurodegenerative disease is multiple systems atrophy. In one embodiment, the neurodegenerative disease is fronto-temporal dementia. In one embodiment, the neurodegenerative disease is lower body Parkinson's syndrome.

The main symptoms of Parkinson's Disease (PD) are rigidity, tremor, and slow movement. There are other diseases in which these symptoms are prevalent. These diseases, and PD itself, fall under the umbrella term Parkinsonism. PD can be referred to as Primary Parkinsonism. Other examples of Parkinsonisms include: Multiple System Atrophy; Progressive Supranuclear Palsy; Normal pressure hydrocephalus; and Vascular or arteriosclerotic parkinsonism. Those diseases that can be classed as Parkinsonisms, but are not PD, can also be referred to as "Parkinson-Plus Syndromes." Unlike PD patients, individuals with Parkinson-Plus Syndromes do not respond to LDopa. The term "parkinsonism" as used herein may refer to a motor syndrome whose main symptoms are tremor at rest, stiffness, slowing of movement and postural instability. Parkinsonian syndromes can be divided into four subtypes, according to their origin: primary or idiopathic; secondary or acquired; hereditary parkinsonism; and Parkinson plus syndromes or multiple system degeneration.

In one embodiment, the parkinsonism is a Parkinson plus syndrome or multiple system degeneration. In one embodiment, the parkinsonism is vascular Parkinsonism (arteriosclerotic Parkinsonism; lower-body Parkinsonism), Multiple System Atrophy with predominant parkinsonism (MSA-P), Multiple System Atrophy with cerebellar features (MSA-C; Sporadic olivopontocerebellar atrophy (OPCA)), Shy-Drager syndrome, Progressive supranuclear Palsy (Steele-Richardson-Olszewski syndrome), Lewy body dementia, Pick's disease, or frontotemporal dementia and parkinsonism linked to chromosome 17.

The phrase "delay progression of a LSD" and the like as used herein means delaying the onset, i.e., increasing the time to appearance, of a symptom of a LSD or a mark associated with a LSD in a subject (compared to that typically observed). It may include substantially slowing, preventing, or even entirely preventing, the onset of the disease or of one or more symptoms and/or complications associated with the disease.

The phrase "delaying progression of a neurodegenerative disease" or "delaying progression of a neurodegenerative disease associated with defects in lysosomal storage" refer to delaying the onset, i.e., increasing the time to appearance, of a symptom of a neurodegenerative disease or neurodegenerative disease associated with defects in lysosomal storage, or a mark associated with a neurodegenerative disease or neurodegenerative disease associated with defects in lysosomal storage (compared to that typically observed). It may include substantially slowing, preventing, or even entirely preventing, the onset of the disease or of one or more symptoms and/or complications associated with the disease.

Delaying progression thus includes, but is not limited to, delaying or preventing symptoms and/or complications resulting from or associated with, e.g., a LSD, a neurodegenerative disease, or a neurodegenerative disease associated with defects in lysosomal storage. When provided prophylactically, acetyl-leucine is typically provided before the onset of a symptom of a LSD, a neurodegenerative disease, or a neurodegenerative disease associated with defects in lysosomal storage. Such prophylactic administration is typically to delay or prevent the onset of symptoms of the LSD, a neurodegenerative disease, or a neurodegenerative disease associated with defects in lysosomal storage.

A "symptom" of a LSD includes any clinical or laboratory manifestation associated with a LSD and is not limited to what the subject can feel or observe. Symptoms as described herein include neurological symptoms. Examples of neurological symptoms include ataxia, dystonia, vertical and horizontal supranuclear saccade/gaze palsy and dementia. Also included are psychiatric symptoms such as depression or psychosis. Most of the LSDs can be diagnosed based on the subject history, clinical findings, biochemical markers and genetic testing.

A "symptom" of a neurodegenerative disease, optionally associated with defects in lysosomal storage, includes any clinical or laboratory manifestation associated with a neurodegenerative disease and is not limited to what the subject can feel or observe. Symptoms as described herein include neurological symptoms.

Progression could be said to be delayed when the time to appearance of a symptom of a LSD or a mark associated with a LSD, or appearance of a symptom of a neurodegenerative disease takes at least 5% longer than that typically observed for a subject having a LSD or neurodegenerative disease. In some embodiments, an increase in time of at least 10%, at least 15%, at least 20%, at least 25%, at least 30%, at least 40%, at least 50%, at least 60%, at least 70%, at least 80%, at least 90% or at least 100% is observed.

Disease treatment or progression can be assessed using one or more of the following: the Scale for the Assessment and Rating of Ataxia (SARA), Spinocerebellar Ataxia Functional Index (SCAFI), the modified Disability Rating Scale (mDRS), EuroQol 5Q-5D-5L (EQ-5D-5L), the visual analogue scale (VAS), Wechsler Adult Intelligence Scale-Revised (WAIS-R), Wechsler Intelligence Scale for Children-IV (WISC-IV), or Montreal Cognitive Assessment (MoCA). For certain LSDs, such as NPC, particular scores have been developed and validated over the last decades, for instance the modified 6-Domain NP-C disability Scale (mDRS score). In this regard, certain scores in these tests are characteristic of symptomatic LSD or neurodegenerative subjects. Thus, "delaying progression of a LSD" or "delaying progression of a neurodegenerative disease" can mean increasing the time taken for a subject to reach a SARA, SCAFI, mDRS, EQ-5D-5L, VAS, WAIS-R, WISC-IV and/or MoCA score, or other relevant test, that is characteristic of a symptomatic LSD subject or neurodegenerative subject (compared to that typically observed).

"Treating a neurodegenerative disease," "treating a neurodegenerative disease associated with defects in lysosomal storage," or "treating a LSD" may be equated with an improvement in a SARA, SCAFI, mDRS, EQ-5D-5L, VAS, WAIS-R, WISC-IV and/or MoCA score, or result of another test suitable for characterizing a neurodegenerative disease or LSD subject. In some embodiments, treatment improves such as score from a value characteristic of a symptomatic subject to a value characteristic of a non-symptomatic subject.

Any change in LSD or neurodegenerative disease progression, for example, over time or through treatment, can be monitored by using one or more well-established tests, as discussed further herein, at two or more time points and comparing the results.

Thus, to evaluate overall neurological status, mDRS, a four-domain scale (ambulation, manipulation, language and swallowing), can be applied. Cerebellar function can be evaluated using SARA, an eight-item clinical rating scale (gait, stance, sitting, speech, fine motor function and taxis; range 0-40, where 0 is the best neurological status and 40 the worst), and SCAFI, comprising the 8-m-Walking-Time (8MW; performed by having subjects walking twice as quickly as possible from one line to another excluding turning), 9-Hole-Peg-Test (9HIPT) and the number of "PATA" repetitions over 10 s. Subjective impairment and quality of life can be evaluated using the EQ-5D-5L questionnaire and VAS. To assess ocular motor function, 3-dimensional videooculography (EyeSeeCam) can be used to measure the peak velocity of saccades, gain of smooth pursuit, peak slow phase velocity of gaze-evoked nystagmus (gaze-holding function), peak slow phase velocity of optokinetic nystagmus, and gain of horizontal vestibulo-ocular reflex. To evaluate the cognitive state, WAIS-R or WISC-IV, and MoCA, assessing different cognitive domains, including attention and concentration, executive functions, memory, language, visuoconstructional skills, conceptual thinking, calculations, and orientation with a maximum of 30 points and a cut-off score of 26, can be used. The skilled person will know how to perform such tests.

The term "treating a migraine," as used herein refers to reducing the frequency of, alleviating or eliminating migraines, or one or more symptoms related thereto.

The term "preventing a migraine," as used herein refers to preventing migraines, or one or more symptoms associated therewith. A Compound of the Disclosure may be used prophylactically.

The term "alleviating" as used herein means rendering migraines, or one or more symptoms associated therewith, less severe or less intense than in the absence of treatment.

As used herein, the term "reducing the frequency of a migraine" means reducing the occurrence of migraines, or one or more symptoms associated therewith, within a particular time frame relative to the occurrence in the absence of treatment.

In one embodiment, the Compound of the Disclosure reduces the frequency of, alleviates or eliminates one or more migraine symptoms selected from headache, tiredness, aura, nausea, vomiting, sensitivity to light, sensitivity to sound, sensitivity to smell, sweating, poor concentration, feeling hot or cold, abdominal pain and diarrhea.

As used herein, a symptom associated with migraine includes any clinical or laboratory manifestation associated with a migraine and is not limited to what the subject can feel or observe.

In another embodiment, the disclosure provides a Compound of the Disclosure for use in treating, or more preferably preventing, an aura, e.g., a visual aura.

In another embodiment, the disclosure provides a Compound of the Disclosure for use in treating or preventing a migraine associated with an aura (for example, a "classic migraine").

In another embodiment, the disclosure provides a Compound of the Disclosure for use in treating or preventing a migraine that is not associated with an aura (for example, a "common migraine").

In another embodiment, the disclosure provides a Compound of the Disclosure for use in treating or preventing an aura associated with a migraine headache.

In another embodiment, the disclosure provides a Compound of the Disclosure for use in treating or preventing an aura that is not associated with a migraine headache.

In another embodiment, the disclosure provides a Compound of the Disclosure for use in treating or preventing a hemiplegic migraine. For this embodiment, the migraine typically comprises a headache and an aura that are accompanied by motor weakness.

In another embodiment, the disclosure provides a Compound of the Disclosure for use in treating or preventing a sporadic hemiplegic migraine.

In another embodiment, the disclosure provides a Compound of the Disclosure for use in treating or preventing a vestibular migraine. Vestibular migraines can be defined according to diagnostic criteria set forth by the International Classification Committee of the Barany Society and are typically characterized by:

A. At least 5 episodes with vestibular symptoms (as defined by the Barany Society's Classification of Vestibular Symptoms) of moderate or severe intensity, lasting 5 minutes to 72 hours;

B. Current or previous history of migraine with or without aura according to the International Classification Headache Disorders (ICHD);

C. One or more migraine features with at least 50% of the vestibular episodes:

1. headache with at least two of the following characteristics: one sided location, pulsating quality, moderate or severe pain intensity, aggravation by routine physical activity;
2. photophobia and phonophobia;
3. visual aura;

D. Not better accounted for by another vestibular or ICHD diagnosis.

In another embodiment, the disclosure provides a Compound of the Disclosure for use in treating or preventing a basilar-type migraine. For this embodiment, the migraine typically comprises a headache and an aura that are accompanied by one or more of the following symptoms: difficulty speaking, world spinning, ringing in ears, and other brainstem-related symptoms.

In another embodiment, the disclosure provides a Compound of the Disclosure for use in treating or preventing a retinal migraine. For this embodiment, the retinal migraine typically includes headaches accompanied by visual disturbances or temporary blindness.

In another embodiment, the disclosure provides a Compound of the Disclosure for use in treating or preventing chronic migraine. As used herein, the term "chronic migraine" refers to a subject suffering more than fifteen headache days per month over a three month period of which more than eight are migrainous, in the absence of medication (as defined by The International Headache Society).

In another embodiment, the disclosure provides a Compound of the Disclosure for use in treating or preventing episodic migraine. As used herein, "episodic migraine" refers to a subject suffering less than fifteen headache days per month over a three month period, in the absence of medication (as defined by The International Headache Society).

In another embodiment, the disclosure provides a Compound of the Disclosure for use in treating or preventing acute migraine.

In another embodiment, the disclosure provides a Compound of the Disclosure for use in treating or preventing one or more prodromal symptoms associated with a migraine. Preferably, the prodromal symptoms are selected from one or more of altered mood, irritability, depression or euphoria, fatigue, craving for certain food(s), stiff muscles (especially in the neck), constipation, diarrhea, and sensitivity to smells and noise.

In another embodiment, the disclosure provides a Compound of the Disclosure for use in treating or preventing pain associated with a migraine.

In another embodiment, the disclosure provides a Compound of the Disclosure for use in treating or preventing one or more postdromal symptoms associated with a migraine. Preferably, the postdromal symptoms are selected from one or more of soreness in the area where the migraine was, impaired thinking, tiredness, head pain, cognitive difficulties, gastrointestinal symptoms, mood changes and weakness.

In another embodiment, the disclosure provides a Compound of the Disclosure that reduces, alleviates or eliminates migraine headaches.

In another embodiment, the disclosure provides a Compound of the Disclosure that alleviates or eliminates aura.

In another embodiment, the disclosure provides a Compound of the Disclosure that reduces the frequency of, alleviates or eliminates one or more symptoms selected from visual problems or visual disturbances, numbness or tingling, dizziness, balance problems, motor problems, speech difficulties and loss of consciousness.

In another embodiment, the disclosure provides a Compound of the Disclosure that prevents an aura from occurring, for example, by preventing one or more of the above-mentioned symptoms from occurring.

In one embodiment, the disclosure provides a Compound of the Disclosure for use in a method of improving cognitive function, mobility, or cognitive function and mobility in a subject.

In another embodiment, the disclosure provides a Compound of the Disclosure for use in a method of improving cognitive function in a subject.

In another embodiment, the disclosure provides a Compound of the Disclosure for use in a method of improving mobility in a subject.

In another embodiment, the subject is an elderly subject.

In another embodiment, the disclosure provides a Compound of the Disclosure for use in a method of improving mobility and/or cognitive function in an elderly subject.

In another embodiment, the disclosure provides a method of improving mobility and/or cognitive function in an elderly subject, the method comprising administering a therapeutically effective amount of a Compound of the Disclosure to the subject.

In another embodiment, the cognitive function is one or more selected from the group consisting of perception, memory, creation of imagery, awareness, reasoning, thinking and capacity for judgment.

According to the present disclosure, a Compound of the Disclosure may be used to treat an age-related decrease in cognitive function and/or mobility.

In another embodiment, the disclosure provides a Compound of the Disclosure for use in treating restless legs syndrome.

In another embodiment, the disclosure provides a Compound of the Disclosure for use in treating vertigo.

"Mobility" refers to the ability of a subject to move. Mobility may be assessed in the elderly using one or more simple tests. For example, the "get up and go" test is a simple test capable of measuring mobility. In this test, the speed of sit to stand and walking to a target point is analyzed.

For example, the test may begin with the subject sitting in a chair. At the start of the stop clock, the subject should rise unaided and walk to a target point. The target point may be 2-10 m away, optionally 4-6 m away. The stop clock should be stopped upon the subject reaching the target point. Any change in mobility, for example, over time or through treatment, can be monitored by using the "get up and go" test at two or more time points and comparing the results. Other suitable tests for measuring mobility include those used in the Elderly Mobility Scale (EMS), a 20-point validated assessment tool for the assessment of frail elderly subjects considering locomotion, balance and key position changes.

The phrase "improving mobility," as referred to herein, means a positive change in the ability of the subject to move. The positive change can be measured using any of the aforementioned tests on two or more occasions, for example, a first occasion to measure baseline mobility and a second occasion to measure mobility following a period of time (in which treatment may have been administered). The more confident the subject feels due to improved steadiness (with treatment, for example) the more rapidly he or she completes the test. Mobility could be said to be improved when at least a about 5% increase in performance in the relevant test, between two time points, is observed. For example, an increase in performance of at least about 10%, at least about 15%, at least about 20%, at least about 25%, at least about 30%, at least about 40%, at least about 50%, at least about 60%, at least about 70%, at least about 80%, at least about 90% or at least about 100% in the relevant test, between the two time points, is observed. Further for example, an increase in performance of at least 5%, at least 10%, at least 15%, at least 20%, at least 25%, at least 30%, at least 40%, at least 50%, at least 60%, at least 70%, at least 80%, at least 90% or at least 100% in the relevant test, between the two time points, is observed. The two time points may be one week apart, two weeks apart, three weeks apart, four weeks apart, two months apart, three months apart, four months apart, five months apart or even six months apart. Treatment may be administered during the intervening period. Thus, as an example, "improving mobility" can mean that the subject will demonstrate an at least about 5% increase in speed from a baseline measurement, as measured using the "get up and go" test as defined herein. For example, the subject may demonstrate an increase in speed in this test of at least about 10%, at least about 15%, at least about 20%, at least about 25%, at least about 30%, at least about 40%, at least about 50%, at least about 60%, at least about 70%, at least about 80%, at least about 90% or at least about 100%. Further for example, the subject may demonstrate an increase in speed in this test of at least 5%, at least 10%, at least 15%, at least 20%, at least 25%, at least 30%, at least 40%, at least 50%, at least 60%, at least 70%, at least 80%, at least 90% or at least 100%.

In one embodiment, the subject has a mobility disorder associated with ageing.

The term "mobility disorder associated with ageing" as used herein refers to an impairment in mobility that is a direct consequence of the ageing process; this is in contrast with an impairment in mobility that is not a direct consequence of the ageing process. Clinical presentation may differ between subjects with a mobility disorder associated with ageing and subjects with impairment in mobility that is not a direct consequence of the ageing process, for example subjects with ataxia. Ataxia may present as a subject slaloming during walking, while a mobility disorder associated with ageing may present as an increased propensity to falls. Thus, for example, cerebellar ataxia is not a mobility disorder associated with ageing.

In addition to the mobility assessments disclosed above, mobility in a subject having a mobility disorder associated with ageing may be tested, for example, using assessments of balance and/or through monitoring the number of falls experienced by the subject and/or using the "get up and go" test.

In another embodiment, the disclosure provides a Compound of the Disclosure for use to improve balance in a subject, wherein the subject has impaired balance associated with ageing. According to the present disclosure, the impaired balance associated with ageing is not vertigo.

According to the present disclosure, the subject may, for example, not have benign paroxysmal positional vertigo (BPPV); vestibular neuritis; vertigo related to Meniere's disease, Wallenberg's syndrome, cerebellar ischemia, perilymph fistula or acoustic neurinoma; or recurring vertigo of traumatic or toxic origin.

In another embodiment, the disclosure provides a Compound of the Disclosure for use to treat balance disorder associated with ageing.

In another embodiment, the disclosure provides a Compound of the Disclosure for use to increase a subject's stability, for example when standing and/or walking, wherein the subject has decreased stability associated with ageing.

In another embodiment, the disclosure provides a Compound of the Disclosure for use to reduce a subject's unsteadiness whilst walking, wherein the subject has increased unsteadiness associated with ageing.

In another embodiment, the disclosure provides a Compound of the Disclosure for use to treat a subject with impaired gait wherein the impaired gait is associated with ageing. The subject may have senile gait disorder.

In another embodiment, the disclosure provides a Compound of the Disclosure for use to increase gait velocity and or cadence in a subject wherein the subject has impaired gait velocity and or cadence associated with ageing.

In another embodiment, the disclosure provides a Compound of the Disclosure for use to treat a subject that has a pre-disposition to falls, wherein the pre-disposition to falls is associated with ageing.

"Cognitive function" can mean any mental process that involves a symbolic operation, for example, perception, memory, creation of imagery, awareness, reasoning, thinking and capacity for judgment. Measures of cognitive functioning include assessment tools designed to measure, for example: (a) general intelligence, (b) nonverbal intelligence, (c) achievement, (d) attention/executive functioning, (e)

memory and learning, (f) visual-motor and motor functioning and (g) language. Such assessment tools are well-known in the art and include, for example, Wechsler Adult Intelligence Scale and Woodcock-Johnson III Tests of Cognitive Abilities (both for assessing general intelligence), Raven Progressive Matrices (for assessing nonverbal intelligence), Wide Range Achievement Test and Woodcock-Johnson III Tests of Achievement (for assessing academic achievement), Conners' Continuous Performance Test II (for assessing attention/executive functioning), Wide Range Assessment of Memo:ry and Learning (for assessing memory and learning), Bender Visual-Motor Gestalt Test, Halstead-Reitan Grip Strength Test, Halstead-Reitan Finger Tapping Test and Lafayette Grooved Pegboard Task (all for assessing visual-motor and motor functioning) and Peabody Picture Vocabulary Test (for assessing language).

Cognitive function may also be assessed using reaction speed and/or alertness tests, such as the Psychomotor Vigilance Task (e.g. as disclosed in the Examples). This test assesses components including fine motor skills; psychomotor speed; lapses of attention; instability of alertness; and impulsivity induced by fatigue.

For example, the Psychomotor Vigilance Task (PVT) is a sustained-attention, reaction timed task that measures the speed with which subjects respond to a visual stimulus. The subject monitors a screen and presses the screen as quickly as possible upon the appearance of visual stimuli. The visual stimuli will then disappear and reappear (at irregular time intervals) e.g., 10 times over the course of the test, with the subject touching the screen as quickly as possible upon each reappearance. Test performance is quantified from an average of the e.g. 10 reaction times. Any change in cognitive function, for example, over time or through treatment, can be monitored by using one or more of these well-established tests at two or more time points and comparing the results.

The phrase "improving cognitive function," as referred to herein, means a positive change in the ability of the subject to perform a symbolic operation, for example, to perceive, remember, create a mental image, have clarity of thought, be aware, to reason, think or judge. The positive change can be measured using any of the aforementioned tests on two or more occasions, for example, a first occasion to measure baseline cognitive function and a second occasion to measure cognitive function following a period of time (in which treatment may have been administered). Cognitive function could be said to be improved when at least about a 5% increase in performance in the relevant test, between two time points, is observed. For example, an increase in performance of at least about 10%, at least about 15%, at least about 20%, at least about 2S %, at least about 30%, at least about 40%, at least about 50%, at least about 60%, at least about 70%, at least about 80%, at least about 90% or at least about 100% in the relevant test, between the two time points, is observed. Further for example, an increase in performance of at least 5%, at least 10%, at least 15%, at least 20%, at least 25%, at least 30%, at least 40%, at least 50%, at least 60%, at least 70%, at least 80%, at least 90% or at least 100% in the relevant test, between the two time points, is observed. The two time points may be one week apart, two weeks apart, three weeks apart, four weeks apart, two months apart, three months apart, four months apart, five months apart or even six months apart. Treatment may be administered during the intervening period. Thus, as an example, "improving cognitive function" can mean that the subject will demonstrate an at least about 5% increase in performance from a baseline measurement, as measured using the well-established Wechsler Adult Intelligence Scale. For example, the subject may demonstrate an increase in performance in this test of at least about 10%, at least about 15%, at least about 20%, at least about 25%, at least about 30%, at least about 40%, at least about 50%, at least about 60%, at least about 70%, at least about 80%, at least about 90% or at least about 100%. Further for example, the subject may demonstrate an increase in performance in this test of at least 5%, at least 10%, at least 15%, at least 20%, at least 25%, at least 30%, at least 40%, at least 50%, at least 60%, at least 70%, at least 80%, at least 90% or at least 100%.

In another embodiment, the disclosure provides a Compound of the Disclosure for use to increase reaction speed, for example the time in which a subject responds to a visual stimulus.

In one embodiment, the subject has a decrease in cognitive function associated with ageing.

The term "decrease in cognitive function associated with ageing" as used herein refers to a decrease in cognitive function that is a direct consequence of the ageing process; in contrast with a decrease in cognitive function that is not a direct consequence of the ageing process. Clinical presentation may differ between subjects with a decrease in cognitive function associated with ageing and subjects with decrease in cognitive function that is not a direct consequence of the ageing process.

The term "improving" when used in reference to mobility and/or cognitive function may encompass treating and/or ameliorating any impaired mobility and/or cognitive decline in the subject. An age-related decrease in mobility and/or cognitive function may thus be partially or wholly reversed using a Compound of the Disclosure as described herein.

The term "restless legs syndrome" or "RLS" as used herein includes any form of RLS, including primary RLS and secondary RLS. In one embodiment, the RLS is primary RLS. In another embodiment, the RLS is secondary RLS. In another embodiment, the RLS is secondary to a disease or medical condition. Examples of such diseases or medical conditions include iron deficiency, renal failure, uremia, peripheral neuropathy, varicose veins, a neurodegenerative disease, stress, sleep deprivation, fibromyalgia, hyper- or hypothyroidism, pregnancy, cigarette smoking, vitamin deficiency (e.g., vitamin B-12 deficiency), mineral deficiency (e.g., magnesium deficiency), amyloidosis, lyme disease, spinal nerve damage, rheumatoid arthritis, and Sjögren syndrome. In another embodiment, the RLS is secondary to a medication or substance. Examples of such medications or substances include alcohol, caffeine, anticonvulsant drugs (e.g., phenytoin), antidepressants (e.g., amitriptyline, paroxetine), medication for high blood pressure (e.g., beta-blockers), antipsychotics, and withdrawal from medication(s) (e.g., vasodilator drugs, sedatives, antidepressants). Examples of neurodegenerative diseases include Parkinson's Disease, Huntington's disease, hereditary spastic paraparesis, amyotrophic lateral sclerosis (ALS), Alzheimer's disease, frontotemporal dementia, dementia with Lewy bodies, multiple system atrophy, progressive supranuclear palsy, and corticobasal degeneration. In one embodiment, the neurodegenerative disease is a Motor Neuron Disease (e.g., progressive bulbar palsy (PBP), pseudobulbar palsy, primary lateral sclerosis (PLS), amyotrophic lateral sclerosis (ALS), progressive muscular atrophy (PMA), Huntington's disease, multiple sclerosis, Parkinson's Disease, Canavan disease, frontotemporal lobar degeneration, narcolepsy, Pelizaeus-Merzbacher disease, and spinal muscular atrophy). In one embodiment, the neurodegenerative disease is parkinsonism, including primary or idiopathic, secondary or acquired, hereditary parkinsonism, and Parkinson plus syndromes or multiple system degeneration. In another embodiment, the disease or medical condition is associated with dopaminergic system dysfunction, such as dopaminergic cell loss.

A symptom associated with RLS includes any clinical or laboratory manifestation associated with RLS. Symptoms of RLS are often, but need not be, manifestations associated with the disease that the subject can feel or observe. Symptoms associated with RLS include, but are not limited to, lower leg sensations, periodic limb movements of sleep (PLMS), unpleasant leg sensation, urge to move, restlessness, sleep disturbances, excessive daytime sleepiness and the like.

In another embodiment, a Compound of the Disclosure is used in a method for diminishing, inhibiting, or eliminating one or more symptoms associated with RLS in a subject in need thereof. The method comprises administering to the subject a therapeutically effective amount of the Compound of the Disclosure.

In another embodiment, the one or more symptoms are chosen from any one or combination of lower leg sensations, periodic leg movements of sleep, unpleasant leg sensations, urge to move, restlessness, excessive daytime sleepiness, and sleep disturbances.

The severity of RLS or one or more symptoms of RLS may be assessed, e.g., using a known scale, index, rating, or score. For example, the scale, index, rating, score, or other suitable test may correspond to the severity of the RLS overall or to the severity of one or more symptoms associated with RLS. In one embodiment, the treatment described herein improves such an assessment from a value or degree characteristic of a symptomatic subject to a value or degree characteristic of a non-symptomatic subject.

In one embodiment, the treatment described herein improves such an assessment compared to a baseline. The baseline may be, for example, the subject's condition before initiating any treatment for RLS or before initiating treatment for RLS with a Compound of the Disclosure. Alternatively, the baseline may be, for example, the subject's condition after a certain time period on treatment for RLS.

In one embodiment, treatment with a Compound of the Disclosure decreases the subject's International Restless Leg Syndrome Study Group Rating Scale ("IRLS") compared to a baseline. In one embodiment, the IRLS is reduced compared to baseline by at least 10%, at least 20%, at least 30%, at least 40%, or at least 50%. In one embodiment, the IRLS is reduced by at least 60%, at least 70%, at least 80%, at least 90%, or 100%.

The term "vertigo" as used herein includes any form of vertigo including, for example, benign paroxysmal positional vertigo (BPPV), vestibular neuritis; vertigo related to Meniere's disease, Wallenberg's syndrome, cerebellar ischemia, perilymph fistula or acoustic neurinoma, or recurring vertigo of traumatic or toxic origin.

A symptom of vertigo includes any clinical or laboratory manifestation associated with vertigo. Symptoms of vertigo include, but are not limited to, feeling nauseated, vomiting, abnormal or jerking eye movements (nystagmus), headache, sweating, ringing in the ears, and/or hearing loss.

In methods of the present disclosure, a therapeutically effective amount of a Compound of the Disclosure, typically formulated in accordance with pharmaceutical practice, is administered to a subject, e.g., a human being, in need thereof. Whether such a treatment is indicated depends on the individual case and is subject to medical assessment (diagnosis) that takes into consideration signs, symptoms, and/or malfunctions that are present, the risks of developing particular signs, symptoms and/or malfunctions, and other factors.

A Compound of the Disclosure can be administered by any suitable route, for example by oral, buccal, inhalation, sublingual, rectal, vaginal, intracisternal or intrathecal through lumbar puncture, transurethral, nasal, percutaneous, i.e., transdermal, or parenteral (including intravenous, intramuscular, subcutaneous, intracoronary, intradermal, intramammary, intraperitoneal, intraarticular, intrathecal, retrobulbar, intrapulmonary injection and/or surgical implantation at a particular site) administration. Parenteral administration can be accomplished using a needle and syringe or using a high-pressure technique.

Pharmaceutical compositions include those wherein a Compound of the Disclosure is administered in an effective amount to achieve its intended purpose. The exact formulation, route of administration, and dosage is determined by an individual physician in view of the diagnosed condition or disease. Dosage amount and interval can be adjusted individually to provide levels of a Compound of the Disclosure that is sufficient to maintain therapeutic effects.

Toxicity and therapeutic efficacy of the Compounds of the Disclosure can be determined by standard pharmaceutical procedures in cell cultures or experimental animals, e.g., for determining the maximum tolerated dose (MTD) of a compound, which defines as the highest dose that causes no toxicity in animals. The dose ratio between the maximum tolerated dose and therapeutic effects, e.g., delay progression of a LSD or neurodegenerative disease, is the therapeutic index. The dosage can vary within this range depending upon the dosage form employed, and the route of administration utilized. Determination of a therapeutically effective amount is well within the capability of those skilled in the art, especially in light of the detailed disclosure provided herein.

A therapeutically effective amount of a Compound of the Disclosure required for use in therapy varies with the nature of the condition being treated, the length of time that activity is desired, and the age and the condition of the subject, and ultimately is determined by the attendant physician. Dosage amounts and intervals can be adjusted individually to provide plasma levels that are sufficient to maintain the desired therapeutic effects. The desired dose conveniently can be administered in a single dose, or as multiple doses administered at appropriate intervals, for example as one, two, three, four or more subdoses per day. Multiple doses often are desired, or required. For example, a Compound of the Disclosure can be administered at a frequency of: four doses delivered as one dose per day at four-day intervals (q4d×4); four doses delivered as one dose per day at three-day intervals (q3d×4); one dose delivered per day at five-day intervals (qd×5); one dose per week for three weeks (qwk3); five daily doses, with two days rest, and another five daily doses (5/2/5); or, any dose regimen determined to be appropriate for the circumstance. In situations where chronic treatment is required, multiple doses per day may administered to the patient for extended periods of time, e.g., for about 3 months, about 6 months, about 1 year, about 2 years, about 3 years, about 5 years, about 10 years, or more.

A Compound of the Disclosure used in a method of the present disclosure can be administered in an amount of about 1 to about 5,000 milligrams (mg) per dose, about 100 to about 1,000 mg per dose, or about 250 to about 750 mg per dose. For example, a Compound of the Disclosure can be administered, per dose, in an amount of about 100, 150, 200, 250, 300, 350, 400, 450, 500, 550, 600, 650, 700, 750, 800, 850, 900, 950, or 1,000 mg, including all doses between 1 and 1000 mg.

A Compound of the Disclosure used in a method of the present disclosure can be administered to a subject at an amount of between 250 and 30,000 mg per day, between 250 and 15,000 mg per day between 500 and 10,000 mg per day, between 1,000 and 5,000 mg per day, or between 1,500 and 2,500 per day. For example, a Compound of the Disclosure can be administered to a subject, per day, in an amount of about 250 mg, about 500 mg, about 750 mg, about 1,000 mg, about 1,500 mg, about 2,000 mg, about 2,500 mg, about 3,000 mg, about 3,500 mg, about 4,000 mg, about 4,500 mg, about 5,000 mg, about 6,000 mg, about 7,000 mg, about 8,000 mg, about 9,000 mg, about 10,000 mg, about 11,000 mg, about 12,000 mg, about 13,000 mg, about 14,000 mg, or about 15,000 mg.

The total daily dose may be spread across multiple administrations, i.e., administration may be required two or more times a day to achieve the required dose. As an example, the required number of tablets to provide the total daily dose of a Compound of the Disclosure may be split across two administrations (for example, in the morning and evening) or three administrations (for example, in the morning, noon and evening).

The dosage of a composition containing a Compound of the Disclosure, or a composition containing the same, can be from about 1 ng/kg to about 200 mg/kg, about 1 μg/kg to about 100 mg/kg, or about 1 mg/kg to about 50 mg/kg. The dosage of a composition can be at any dosage including, but not limited to, about 1 μg/kg. The dosage of a composition may be at any dosage including, but not limited to, about 1 μg/kg, about 10 μg/kg, about 25 μg/kg, about 50 μg/kg, about 75 μg/kg, about 100 μg/kg, about 125 μg/kg, about 150 μg/kg, about 175 μg/kg, about 200 μg/kg, about 225 μg/kg, about 250 μg/kg, about 275 μg/kg, about 300 μg/kg, about 325 μg/kg, about 350 μg/kg, about 375 μg/kg, about 400 μg/kg, about 425 ag/kg, about 450 ag/kg, about 475 ag/kg, about 500 ag/kg, about 525 ag/kg, about 550 μg/kg, about 575 μg/kg, about 600 μg/kg, about 625 μg/kg, about 650 μg/kg, about 675 μg/kg, about 700 μg/kg, about 725 μg/kg, about 750 μg/kg, about 775 μg/kg, about 800 μg/kg, about 825 μg/kg, about 850 μg/kg, about 875 μg/kg, about 900 μg/kg, about 925 μg/kg, about 950 μg/kg, about 975 μg/kg, about 1 mg/kg, about 5 mg/kg, about 10 mg/kg, about 15 mg/kg, about 20 mg/kg, about 25 mg/kg, about 30 mg/kg, about 35 mg/kg, about 40 mg/kg, about 45 mg/kg, about 50 mg/kg, about 60 mg/kg, about 70 mg/kg, about 80 mg/kg, about 90 mg/kg, about 100 mg/kg, about 125 mg/kg, about 150 mg/kg, about 175 mg/kg, about 200 mg/kg, or more. The above dosages are exemplary of the average case, but there can be individual instances in which higher or lower dosages are merited, and such are within the scope of this disclosure. In practice, the physician determines the actual dosing regimen that is most suitable for an individual subject, which can vary with the age, weight, and response of the particular subject.

Kits

In another embodiment, the present disclosure provides kits which comprise a Compound of the Disclosure (or a composition comprising a Compound of the Disclosure) packaged in a manner that facilitates their use to practice methods of the present disclosure. In one embodiment, the kit includes a Compound of the Disclosure (or a composition comprising a Compound of the Disclosure) packaged in a container, such as a sealed bottle or vessel, with a label (and/or instructions) affixed to the container or included in the kit that describes use of the compound or composition to practice methods of the disclosure. In one embodiment, the compound or composition is packaged in a unit dosage form. The kit further can include a device suitable for administering the composition according to the intended route of administration.

The term "container" means any receptacle and closure therefore suitable for storing, shipping, dispensing, and/or handling a pharmaceutical product.

The term "insert" means information accompanying a pharmaceutical product that provides a description of how to administer the product, along with the safety and efficacy data required to allow the physician, pharmacist, and subject to make an informed decision regarding use of the product. The package insert generally is regarded as the "label" for a pharmaceutical product.

Personalized Medicine

In another embodiment, the disclosure provides procedures of personalized medicine for subjects having a LSD or neurodegenerative disease, a migraine, restless legs syndrome, or vertigo, and the symptoms associated therewith, or for subjects in need of improving mobility and/or cognitive function, and encompasses the selection of treatment options with the highest likelihood of successful outcome for individual subjects having a LSD or neurodegenerative disease, a migraine, restless legs syndrome, or vertigo, and the symptoms associated therewith, or for subjects in need of improving mobility and/or cognitive function. In another aspect, the disclosure relates to the use of an assay(s) to predict the treatment outcome, e.g., the likelihood of favorable responses or treatment success, in subjects having a LSD or neurodegenerative disease, a migraine, restless legs syndrome, or vertigo, and the symptoms associated therewith, or for subjects in need of improving mobility and/or cognitive function.

In another embodiment, the disclosure provides methods of selecting a subject, e.g., human subject for treatment of a LSD or neurodegenerative disease with a Compound of the Disclosure, comprising obtaining a biological sample, e.g., blood cells or cerebrospinal fluid, from the subject, testing a biological sample from the subject for the presence of a LSD-related biomarker or neurodegenerative disease-related biomarker, and selecting the subject for treatment if the biological sample contains the biomarker, e.g., an aberrant level of the biomarker in body fluids such as an accumulation or elevated level of the biomarker in body fluids or a depletion or decreased level of the biomarker in body fluids. In another embodiment, the methods further comprise administering a therapeutically effective amount of a Compound of the Disclosure to the subject if the biological sample contains the biomarker. In another embodiment, the same methods can be applied to subject for treatment of a migraine, restless legs syndrome, or vertigo, and the symptoms associated therewith, or for improving mobility and/or cognitive function.

In another embodiment, the disclosure provides methods for predicting treatment outcomes in a subject having a LSD or neurodegenerative disease, comprising obtaining a biological sample from the subject, testing the biological sample from the subject for the presence of a LSD-related biomarker or neurodegenerative disease-related biomarker, wherein the detection of the biomarker indicates the subject will respond favorably to administration of a therapeutically effective amount of a Compound of the Disclosure. Favorable responses include, but are not limited to, delaying the onset of symptoms that would normally be expected in a subject afflicted with a LSD or neurodegenerative disease. In another embodiment, the same methods for predicting treatment outcomes in a subject can be applied to a subject having a migraine, restless legs syndrome, or vertigo, and the symptoms associated therewith, or to a subject in need of improving mobility and/or cognitive function.

In another embodiment, the disclosure provides methods of treating a LSD or neurodegenerative disease, comprising administering a therapeutically effective amount of a Compound of the Disclosure to a subject, e.g., a human subject, with a LSD or neurodegenerative disease in whom the subject's cells contain a LSD-related biomarker or neurodegenerative disease-related biomarker. In one embodiment, the subject is selected for treatment with a Compound of the Disclosure after the subject's cells have been determined to contain a biomarker, e.g., an elevated level of a LSD-related biomarker or neurodegenerative disease-related biomarker, or a decreased level of a LSD-related biomarker or neurodegenerative disease-related biomarker. In another embodiment, the same methods can be applied to a subject for treatment of a migraine, restless legs syndrome, or vertigo, and the symptoms associated therewith, or for improving mobility and/or cognitive function.

In another embodiment, the method of treating a subject having a LSD or neurodegenerative disease comprises obtaining a biological sample from the subject, determining whether the biological sample contains an elevated level of a LSD-related biomarker or neurodegenerative disease-related biomarker, or a decreased level of a LSD-related biomarker or neurodegenerative disease-related biomarker, and administering to the subject a therapeutically effective amount a Compound of the Disclosure if the biological sample contains an elevated level or decreased level of the biomarker. In another embodiment, the same methods can be applied to a subject for treatment of a subject having a migraine, restless legs syndrome, or vertigo, and the symptoms associated therewith, or for improving mobility and/or cognitive function in a subject.

The term "biomarker" as used herein refers to any biological compound, such as a protein, a fragment of a protein, a peptide, a polypeptide, a nucleic acid, etc. that can be detected and/or quantified in a subject in vivo or in a biological sample obtained from a subject. Furthermore, a biomarker can be the entire intact molecule, or it can be a portion or fragment thereof. In one embodiment, the expression level of the biomarker is measured. The expression level of the biomarker can be measured, for example, by detecting the protein or RNA (e.g., mRNA) level of the biomarker. Biomarkers can also be measure by HPLC-MS/MS. In some embodiments, portions or fragments of biomarkers can be detected or measured, for example, by an antibody or other specific binding agent. In some embodiments, a measurable aspect of the biomarker is associated with a given state of the subject, such as a particular stage of a LSD. For biomarkers that are detected at the protein or RNA level, such measurable aspects may include, for example, the presence, absence, or concentration (i.e., expression level) of the biomarker in a subject, or biological sample obtained from the subject. For biomarkers that are detected at the nucleic acid level, such measurable aspects may include, for example, allelic versions of the biomarker or type, rate, and/or degree of mutation of the biomarker, also referred to herein as mutation status.

The term "LSD-related biomarker" as used herein refers to any biological compound, such as a protein, a fragment of a protein, a peptide, a polypeptide, a nucleic acid, etc. that accumulates or decreases in a subject as a consequence of the pathological enzyme defect or as a result of cytopathological process associated with a LSD. Examples of LSD-related biomarkers include, but are not limited to, globotriaosylceramide (Gb3), globotriaosylsphingosine (LysoGb3), LysoGb3 analogs, or methylated/non-methylated Gb3 isoforms in connection with Fabry disease; glucosylceramide, chitotriosidase (ChT), pulmonary and activation-regulated chemokine (CCL18/PARC), macrophage inflammatory protein 1-alpha and 1-beta (MIP-la and MIP-1(3), Cathepsin K, ganglioside, GM3/monosialodihexosylganglioside, glucosylsphingosine, or osteopontin in connection with Gaucher disease; galactosylceramide, galactosylsphingosine/psychosine in connection with Krabbe disease; dermatan sulfate, heparan sulfate, keratan sulfate, chondroitin-6-sulfate, chondroitin-4,6-sulfate, hyaluronic acid, glycosaminoglycan fragments, β-galactosidase, collagen Iα, fatty-acid-binding-protein 5, nidogen-1, cartilage oligomeric matrix protein, insulin-like growth factor binding protein 7, or protein HEG1 in connection with mucopolysaccharidoses; sphingomyelin, free cholesterol (in fibroblasts), lysosphingomyelin (Lyso-SPM), cholestane-3β,5α,6 β triol (C-triol), 7-ketocholesterol (7-KC), 24(S)-hydroxycholesterol, NPCBA1 (3β-hydroxy,7β-N-acetylglucosaminyl-5-cholenoic acid), NPCBA2 (probably 3β,5α,6β-trihydroxycholanoyl-glycine), Calbindin D, Lyso-sphingomyelin-509 in connection with Niemann-Pick disease; and/or glycogen, tetrasaccharide glucose (Glc4), myostatin, or insulin-like growth factor-I (IGF-I) in connection with Pompe disease. See, e.g., Labato et al., *Diseases* 4:40 (2016); Aerts et al., *J Inherit Metab Dis* 34:605-619 (2011); and Giese et al., *Orphanet Journal of Rare Diseases* 10:78 (2015) for LSD-related biomarkers.

The term "neurodegenerative disease-related biomarker" as used herein refers to any biological compound, such as a protein, a fragment of a protein, a peptide, a polypeptide, a nucleic acid, etc. that accumulates in a subject as a consequence of a neurodegenerative disease.

The term "migraine-related biomarker" as used herein refers to any biological compound, such as a protein, a fragment of a protein, a peptide, a polypeptide, a nucleic acid, etc. that accumulates or decreases in a subject as a consequence of a migraine.

The term "mobility-related biomarker" as used herein refers to any biological compound, such as a protein, a fragment of a protein, a peptide, a polypeptide, a nucleic acid, etc. that accumulates or decreases in a subject as a consequence of a decrease in mobility.

The term "cognitive function-related biomarker" as used herein refers to any biological compound, such as a protein, a fragment of a protein, a peptide, a polypeptide, a nucleic acid, etc. that accumulates or decreases in a subject as a consequence of a decrease or change in cognitive function.

In certain aspects of the disclosure, the biomarker is differentially present in a subject of one phenotypic status (e.g., a subject having a LSD) as compared with another phenotypic status (e.g., a normal undiseased subject).

In addition to individual biological compounds, the term "biomarker" as used herein is meant to include groups or sets of multiple biological compounds. For example, the combination of lyso-SM-509, lyso-Gb3, may comprise a biomarker. Thus, a "biomarker" may comprise one, two, three, four, five, six, seven, eight, nine, ten, fifteen, twenty, twenty-five, thirty, or more, biological compounds.

The determination of the plasma levels of a biomarker in a subject can be performed using any of the many methods known in the art, e.g., using HPLC-MS/MS or LysoTracker® technology. Any method known in the art for quantitating specific LSD-related biomarkers in a subject or a biological sample may be used in the methods of the disclosure.

The term "biological sample" as used herein refers any tissue or fluid from a subject that is suitable for detecting a biomarker, such as lyso-SM-509 plasma levels. Examples of useful biological samples include, but are not limited to, biopsied tissues and/or cells, e.g., solid tumor, lymph gland, inflamed tissue, tissue and/or cells involved in a condition or disease, blood, plasma, serous fluid, cerebrospinal fluid, saliva, urine, lymph, cerebral spinal fluid, and the like. Other suitable biological samples will be familiar to those of ordinary skill in the relevant arts. A biological sample can be analyzed for biomarker expression and/or mutation using any technique known in the art and can be obtained using techniques that are well within the scope of ordinary knowledge of a clinical practioner. In one embodiment of the disclosure, the biological sample comprises blood cells.

The present disclosure provides the following particular embodiments with respect to personalized medicine for subjects having a LSD:

Embodiment I: A method of treating a subject having a LSD, the method comprising administering a therapeutically effective amount of a Compound of the Disclosure to the subject, wherein cells of the subject contain an elevated concentration or a decreased concentration of a LSD-related biomarker.

Embodiment II: A method of treating a subject having a LSD, the method comprising:

(a) determining the concentration of a LSD-related biomarker in a biological sample from the subject, and when the concentration is determined to be higher than that of a control sample, e.g., a sample from a normal undiseased subject, or lower than that of a control sample; and (b) administering to the subject a therapeutically effective amount of a Compound of the Disclosure.

Embodiment III: A method for treating a LSD in a subject having an elevated concentration or decreased concentration of a LSD-related biomarker, the method comprising administering to the subject a therapeutically effective amount of a Compound of the Disclosure.

The present disclosure provides the following particular embodiments with respect to personalized medicine for subjects having a neurodegenerative disease:

Embodiment I: A method of treating a subject having a neurodegenerative disease, the method comprising administering a therapeutically effective amount of a Compound of the Disclosure to the subject, wherein cells of the subject contain an elevated concentration or a decreased concentration of a neurodegenerative disease-related biomarker.

Embodiment II: A method of treating a subject having a LSD, the method comprising:

(a) determining the concentration of a neurodegenerative disease-related biomarker in a biological sample from the subject, and when the concentration is determined to be higher than that of a control sample, e.g., a sample from a normal undiseased subject, or lower than that of a control sample; and (b) administering to the subject a therapeutically effective amount of a Compound of the Disclosure.

Embodiment III: A method for treating a neurodegenerative disease in a subject having an elevated concentration or decreased concentration of a neurodegenerative disease-related biomarker, the method comprising administering to the subject a therapeutically effective amount of a Compound of the Disclosure.

The present disclosure provides the following particular embodiments with respect to personalized medicine for subjects having a migraine, and the symptoms associated therewith:

Embodiment I: A method of treating a subject having a migraine, and the symptoms associated therewith, the method comprising administering a therapeutically effective amount of a Compound of the Disclosure to the subject, wherein cells of the subject contain an elevated concentration or a decreased concentration of a migraine-related biomarker.

Embodiment II: A method of treating a subject having a migraine, and the symptoms associated therewith, the method comprising:

(a) determining the concentration of a migraine-related biomarker in a biological sample from the subject, and when the concentration is determined to be higher than that of a control sample, e.g., a sample from a normal undiseased subject, or lower than that of a control sample; and (b) administering to the subject a therapeutically effective amount of a Compound of the Disclosure.

Embodiment III: A method for treating a migraine, and the symptoms associated therewith in a subject having an elevated concentration or decreased concentration of a migraine-related biomarker, the method comprising administering to the subject a therapeutically effective amount of a Compound of the Disclosure.

The present disclosure provides the following particular embodiments with respect to personalized medicine for subjects in need of improving mobility:

Embodiment I: A method of treating a subject in need of improving mobility, the method comprising administering a therapeutically effective amount of a Compound of the Disclosure to the subject, wherein cells of the subject contain an elevated concentration or a decreased concentration of a mobility-related biomarker.

Embodiment II: A method of treating a subject in need of improving mobility, the method comprising:

(a) determining the concentration of a mobility-related biomarker in a biological sample from the subject, and when the concentration is determined to be higher than that of a control sample, e.g., a sample from a normal undiseased subject, or lower than that of a control sample; and (b) administering to the subject a therapeutically effective amount of a Compound of the Disclosure.

Embodiment III: A method for improving mobility in a subject having an elevated concentration or a decreased concentration of a mobility-related biomarker, the method comprising administering to the subject a therapeutically effective amount of a Compound of the Disclosure.

The present disclosure provides the following particular embodiments with respect to personalized medicine for subjects in need of improving cognitive function:

Embodiment I: A method of treating a subject in need of improving cognitive function, the method comprising administering a therapeutically effective amount of a Compound of the Disclosure to the subject, wherein cells of the subject contain an elevated concentration or a decreased concentration of a cognitive function-related biomarker.

Embodiment II: A method of treating a subject in need of improving cognitive function, the method comprising:

(a) determining the concentration of a cognitive function-related biomarker in a biological sample from the subject, and when the concentration is determined to be higher than that of a control sample, e.g., a sample from a normal undiseased subject, or lower than that of a control sample; and (b) administering to the subject a therapeutically effective amount of a Compound of the Disclosure.

Embodiment III: A method for improving cognitive function in a subject having an elevated concentration or a decreased concentration of a cognitive function-related biomarker, the method comprising administering to the subject a therapeutically effective amount of a Compound of the Disclosure.

General Synthesis

Compounds of the Disclosure are prepared by reacting an amino acid ($R^3$=H) or ester ($R^3$=$C_1$-$C_6$ alkyl or $C_3$-$C_6$ cycloalkyl) starting material with an acyl chloride in aqueous sodium hydroxide according to the following general scheme with respect to Formula I:

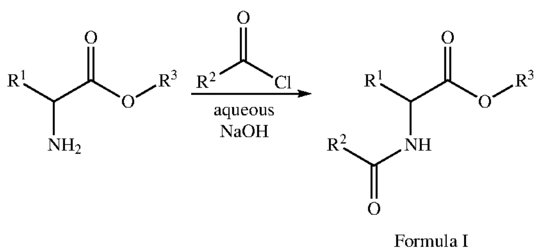

Formula I

EXAMPLES

Example 1

Human Solute Carrier (SLC) Transporter-Mediated Cellular Uptake and Inhibition

Human OAT1 (SLC22A6) and OAT3 (SLC22A8) overexpressing HEK-293 cells and control cells without transfected transporter (Corning® TransportoCells™) are plated to 24-well plates and cellular uptake of 10 to 100 μg/mL of a Compound of the Disclosure is measured in the absence and presence of transporter inhibitors. Uptake of a Compound of the Disclosure into control cells is measured only without chemical inhibitors. Positive control substrates are incubated in parallel to demonstrate presence of active transport in each transporter transfected cell line. Cells are grown in DMEM (Gibco 4196, high glucose, without sodium pyruvate) supplemented with MEM non-essential amino acids and 10% fetal bovine serum. Cells are re-fed with fresh medium after attachment (4-6 hours post-seeding). Cell are plated at a density of 4×105/well in 24-well plates coated with poly-D-lysine. Transporter assays are conducted in 400 μL of HBSS supplemented with 10 mM Hepes, pH 7.4.

The known probe substrates used as positive controls are 3 μM chlorothiazide for OAT1, 2 μM estrone-3-sulfate for OAT3, 10 μM gabapentin for LAT1, 50 μM Gly-Sar for PepT1, 500 μM thiophene-2-glyoxylic acid for MCT1. The known inhibitors used as controls for each transporter are 100 μM diclofenac for OAT1 and OAT3, 10 μM JPH203 for LAT1 and 200 μM losartan for PepT1. All incubations are in triplicate and contain 1% (OAT1 and OAT3) or 0.5% DMSO (LAT, PepT1 and MCT1. The duration of uptake is 5 min OAT1 and OAT3, 3 min for LAT and PepT1 and 1 min for MCT1. Assays are performed at 37° C. with no shaking, except MCT1 at room temperature. To terminate uptake the plate is placed on ice and cells washed twice with ice-cold transport buffer. To collect cells, they are detached with trypsin, and samples of cell suspension transferred into an equal volume of ice-cold acetonitrile. Samples are stored at −20° C. until analysis. In preparation for analysis, samples are centrifuged 20 min (4000 rpm) to separate the precipitated protein. Samples of supernatant are diluted 1:4 with phosphate buffered saline (OAT1, OAT3). Samples diluted with phosphate buffered saline are used for analysis of the Compounds of the Disclosure.

Example 2

Metabolism

A Compound of the Disclosure is incubated at 1 μM, 10 μM and 100 μM with pooled liver S9 fractions from human (mixed gender) and mouse (CD1) at 1.5 mg/mL in 300 μL buffer containing phosphate 100 mM, MgCl2 2 mM, pH 7.4 at 37° C. for 0, 10, 20, 40, 60 min. Reactions are terminated by addition of 2-fold volume of 75% acetonitrile and metabolites separated by liquid chromatography and quantified by mass spectroscopy using multiple reaction monitoring (Thermo Vantage UHPLC+Thermo TSQ Quantis triple quadrupole MS Waters HSS T3 (2.1×100 mm, 1.8 μm column with guard filter).

Liquid Chromatography-Mass Spectrometry

A Compound of the Disclosure, rosuvastatin, estrone-3-sulfate and chlorothiazide are separated and quantified using a Thermo Vanquish UPLC+Thermo Quantis triple quadrupole MS on a Waters Acquity HSS T3 (2.1×50 mm, 1.7 m) column with guard filter. A sample of 4 μL is injected and compounds are eluted at 35° C. with a flow of 0.65 mL/min using a gradient of solvent A=0.1% formic acid and solvent B=acetonitrile as follows (Time, A %): 0.0, 95; 0.5, 95; 2.5, 40; 3.5, 5; 4.5, 95.

Calculations

The $IC_{50}$ value for the test item is determined by fitting the Hill equation in the following form:

$$A\ \% = \frac{\text{Top} - \text{Bottom}}{1 + 10^{(Log[I] - Log IC_{50})}} + \text{Bottom}$$

where A % is the percent activity remaining (the mean cellular uptake observed in the solvent control sample set to 100% and the mean cellular uptake observed in the presence of the positive control inhibitor set to 0%), Top and Bottom are the upper and lower plateau of A %. [I] is the inhibitor concentration and $IC_{50}$ is the inhibitor concentration where the remaining activity is at the midpoint between the Top and Bottom. To obtain robust $IC_{50}$ fit with four test concentrations the Top and the Bottom levels are constrained to 100% and 0%, respectively.

Enzyme kinetic data for uptake and metabolism of a Compound of the Disclosure is analysed by fitting the Michaelis-Menten equation to the data. V0=Vmax[S]/Km+[S], where V0 is initial velocity, [S] is substrate concentration, Vmax is maximum velocity and Km is substrate concentration at half Vmax. All fitting is performed using GraphPad Prism 8.4 software (GraphPad Software Inc). No weighting scheme is applied.

Example 3

Acetylation Alters Physiochemical Properties that Alter Membrane Permeability

The physiochemical parameters of L-leucine were compared with N-acetyl-L-leucine. The physiochemical parameters are provided in FIG. 1(*a*). Both molecules possess similar physicochemical parameters, except for log P, log D and solubility. Log P is the octanol:water partition coefficient for the neutral form of a compound. In contrast, log D considers the ionization state of a molecule in aqueous (biological) solution resulting from basic groups gaining a proton and acidic groups losing a proton, and as such is better correlated with passive diffusion across membranes. For N-acetyl-L-leucine a log D of −2.54 predicts a low rate of passive diffusion across membranes in the neutral environment of the intestine and would require a carrier, as for short-chain fatty acids and acidic drugs such as acetylsalicylic acid.

Passive diffusion of N-acetyl-leucine could occur across membranes in acidic conditions such as the stomach, as shown in FIG. 1(*e*), but in environments with physiological and approximately neutral pH such as the intestine and tissues to which N-acetyl-leucine distributes, carrier-mediated transport is required. Moreover, pharmacokinetics following oral administration in mice revealed high levels of interference between the L- and D-enantiomers of N-acetyl-leucine, suggestive of a specific and saturable binding site and carrier-mediated uptake.

Candidate transporters for N-acetyl-leucine were investigated. Of the 450 possible transporters, plausible candidates were identified based on the physicochemical and steric effect of acetylation, see FIGS. 1*a-d*, reported structure-activity relationship, tissue and cell expression, and their kinetic parameters (low affinity and high capacity).

Example 4

Transport of N-acetyl-L-leucine by the Leucine Transporter LAT1

LAT1 was explored as a candidate for N-acetyl-L-leucine transport as it is the endogenous transporter for leucine, 8 of the 9 essential amino acids, and cysteine, as well as the amino acid-related drugs T3, T4, L-dopa, baclofen, melphalan, gabapentin and the dopamine precursor L-DOPA. Further, LAT1 is the best characterized transporter in terms of transport mechanism, substrate specificity and regulation, is ubiquitously expressed in all tissues, and is the rate-limiting step in leucine activation of mTORC1, which is responsible of cell growth and survival, and could explain mechanistic pharmacology of N-acetyl-L-leucine. It was found that N-acetyl-leucine was neither a substrate (FIG. 2(*a*)) nor an inhibitor of LAT1 (FIG. 2(*c*)), consistent with a previous study that used an indirect assay with radioactive leucine as a surrogate. Small molecules can act as inhibitors if they interact with the substrate binding site without being translocated across the membrane. This is a component in the kinetics of transport, where binding precedes the conformational change that catalyses translocation of the substrate across the membrane.

Example 5

Transport of N-acetyl-L-leucine by the Peptide Transporter PepT1

The effect of introducing an amide bond by acetylation (FIG. 1*d*), which sterically resembles the backbone of a di-peptide and transported by peptide transporters, was studied. PepT1 is a good transporter candidate because it is well characterized, has low affinity and high capacity, and is a popular target for the delivery of peptide-like prodrugs to improve oral absorption and bioavailability. N-acetyl-L-leucine was not a substrate (FIG. 2(*c*)) but was an inhibitor of the peptide transporter PepT1, with an $IC_{50}$ of 0.74 mM (FIG. 2(*d*)). As most substrate-like inhibitors bind to the same binding site the inhibition is competitive and given that di- and tri-peptides are present in the gut at high millimolar concentrations, this level of inhibition would not be of pharmacological consequence as dietary peptides would outcompete N-acetyl-L-leucine at PepT1.

Example 6

Transport of N-acetyl-L-leucine by the Organic Anion Transporter OAT

The hypothesis that the salient chemical feature for carrier-mediated uptake was conversion of leucine from a zwitterion to an anion (FIG. 1(*c*)) was investigated. Anion transporters are relevant in drug development for their roles in drug distribution, elimination and drug-drug interactions. The organic anion transporters (OATs) were investigated based on their structure-activity relationships, kinetics, pattern of tissue expression and role in the pharmacokinetics of many drugs. N-Acetyl-L-leucine was a substrate of OAT1 (FIG. 3(*a*)) and OAT3 (FIG. 3(*b*)). Based on the ability of N-acetyl-L-leucine to inhibit the uptake of the known substrates chlorothiazide and estrone sulfate (FIG. 3(*c*), FIG. 3(*d*)), it inhibited OAT1 with a $IC_{50}$ of 6.2 mM (FIG. 3(*c*)) and OAT3 with an $IC_{50}$ of 0.70 mM (FIG. 3(*d*)).

Example 7

Transport of N-acetyl-L-leucine by the Monocarboxylate Transporter MCT1

The monocarboxylate transporter (MCT) family has 14 members, of which MCT1-MCT4 are well characterized. MCT members are endogenously involved in the bidirectional movement (into and out of cells) of metabolites that perform signalling and energy/metabolic roles including ketone bodies and pyruvate, and uptake of small organic aliphatic acids produced by microbes from the gastrointestinal tract. MCTs play an essential role in the metabolism and pH regulation of cells by moving lactate into and out of cells. As these metabolites are present in the micromolar to millimolar range, the kinetics of these transporter feature low affinity and high capacity. MCTs are widely expressed at various tissues, including the intestine, brain, kidney and liver, delivering various substrates, and a potential target for oral drug delivery as it possesses high transport capacity. MCT1 is present in almost all tissues and is involved in several drugs and nutrients including salicylate, valproate, atorvastatin and γ-hydroxybutyrate, for both uptake and crossing the blood-brain barrier.

The results show that N-acetyl-L-leucine was a substrate of MCT1 with a $K_m$ of 3.0 mM (FIG. 4(*a*)) and an inhibitor of MCT1 (FIG. 3(*c*)) with an $IC_{50}$ of 15 mM. N-acetyl-leucine exhibits stereospecific effects for both its pharmacodynamics and pharmacokinetics, and thus transport of the D-enantiomer was also studied. N-acetyl-D-leucine was also a substrate, with a $K_m$ of 1.0 mM (FIG. 4(*b*)), and an inhibitor of MCT1 with an $IC_{50}$ of 11 mM (FIG. 4(*d*)). Assuming competitive inhibition, the Cheng-Prusoff equation yields an affinity ($K_i$) of 4.3 mM for the L-enantiomer and 1.6 mM for the D-enantiomer, similar to the respective $K_m$ values. This enantiomeric selectivity during transport by MCT1 provides a mechanistic explanation for the lower bioavailability of the L-enantiomer when administered as a racemate which impacts its therapeutic efficacy.

Example 8

Metabolism of N-acetyl-L-leucine to L-leucine Inside Cells

The metabolism of a deuterated N-acetyl-DL-leucine incubated with S9 microsome fraction from liver (FIG. 4(*e*)) was monitored using liquid chromatography and mass spectroscopy. The time course revealed that the disappearance of N-acetyl-DL-[$^2H_{10}$]leucine asymptotically approached 50% of the initial concentration and correlated well with the appearance of L-leucine for both human (FIG. 4(*f*)) and mouse (FIG. 4(*g*)) fractions. Kinetic data fit to the Michaelis-Menten equation yielded a $K_m$ values of 216 and 69 μM and Vmax values of 6.8 and 2.6 μmol/min/mg for human and mouse, respectively (FIG. 4(*b*)). Asymmetric metabolism of the L-enantiomer relative to the D-enantiomer is consistent with previous reports of deacetylation of L but not D amino acids. These metabolic results provide a mechanistic explanation for the faster clearance the L-enantiomer than the D-enantiomer after oral dosing of mice, and are consistent with N-acetyl-L-leucine acting as prodrug, in which both uptake and metabolism are components of its mechanism of action.

Without wishing to be bound by any particular theory with respect to the pharmacological mechanism of action of N-acetyl-leucine, N-acetyl-L-leucine is taken up and distributed by anion transporters, primarily MCTs. From the L-enantiomer, the L-leucine is trapped and utilized in the cell that deacetylates it, with the exception of the liver, which in contrast to all other amino acids does not metabolize leucine, but rather secretes it into the circulation for use by other tissues, particularly skeletal muscle and the central nervous system. MCT1-mediated uptake of N-acetyl-L-leucine provides a way to bypass the easily saturable uptake via LAT to deliver more leucine to tissues. Indeed, at the blood-brain barrier, LAT is not just limited by a low $K_m$ and saturation but also by competition by neural amino acids, which has implications for the availability of amino acids to the CNS that are precursors for neurotransmitters. In contrast to the LAT system that is saturated by amino acids at normal blood levels (total ~2.4 mM), MCT1 can deliver leucine via the prodrug N-acetyl-L-leucine without interference from, and disruption to, the uptake of other essential amino acids. Another advantage of transport by MCTs is that for uptake by LAT, leucine competes with other amino acids such as tyrosine and phenylalanine, which are precursors of neurotransmitters, and is thought to underlie the leucine toxicity in Maple Syrup Disease. MCT1 provides a mechanism to signal via leucine by bypassing the normal and limited uptake by LAT and activate intracellular leucine sensors and activate powerful processes such as mTORC1.

Example 9

Human MCT1-Mediated Transport

Representative Compounds of the Disclosure are tested in (i) MDCK-II cells expressing human transporter MCT1; and (ii) MDCK-II cells transfected with a control vector (GFP) as control cells for human transporter MCT1. 2-Thiophene-glyoxylic acid (TPGA) is the positive control for transport.

A. Test Articles

1. A stock solution is prepared with the test article (Compound of the Disclosure) in DMSO or in HBSS-Bis-Tris.
2. Final assay solutions of probe substrate or test article contain 0.5% (v/v) DMSO (vehicle control).
3. Test article concentrations are 10 μM, 30 μM, 100 μM, 300 μM, 1000 μM, 3000 μM, and 10000 μM. If solubility does not allow testing at 10000 μM, concentrations may be adjusted accordingly.

B. Materials

1. Hank's Balanced Salt Solution (HBSS), with $Ca^{2+}$ and $Mg^{2+}$, pH 7.4 without phenol red.
2. Hank's Balanced Salt Solution (HBSS) with Bis-Tris, pH 5.5, without phenol red.
3. Phosphate Buffered Solution (PBS).
4. Cell Extraction Solution: ACN:Water (50:50).
5. Dimethyl sulfoxide (DMSO).
6. Millipore MultiScreen Filter 96-well insert plate with permeable membrane, (PCF—0.4 μm).
7. Millipore MultiScreen Filter 96-well receiver tray.
8. 2-Thiophene-glyoxylic acid.
9. Test articles.

C. Cell Culture

MDCK-II cells are maintained in DMEM with low glucose and 10% FBS. Cells passages up to 40 are seeded at 60K±10K cells/well on 96-well, transwell membrane plates approximately 24 hours before transfection. Transport assays are carried out approximately 48 hours after transfection.

D. Transport Study for MCT1 (Apical)

1. Test system:
   a. Test system: 96-well cell culture plate with wells containing a monolayer of MDCK-II cells grown on a permeable support and a corresponding 96-well receiver tray. Cell plates are maintained at 37° C. in 5% $CO_2$ atmosphere prior to initiation of the transport experiment.
   b. Pre-incubation is conducted in HBSS, pH 7.4. Transport experiments are conducted in HBSS with Bis-Tris, pH 5.5, without phenol red. Pre-incubation and incubation are conducted at ambient temperatures.
   c. Each condition is run in triplicate wells.
   d. Identical transport studies are conducted using cells expressing the transporter of interest and control cells which do not express the transporter. The result from the control cells is used to correct for substrate permeation by routes other than the transporter being investigated in the study.

2. Prepare the 96-well plate as follows:
   a. Wash the basal side of the culture plate insert with HBSS three times. After the final wash, blot the basal side of the wells and keep this side dry.
   b. Wash the culture plate wells with HBSS three times. The wells of the culture plate serve as the apical compartment.
3. Aspirate the final wash from the culture plate. The wells of the culture plate serve as the apical compartment. Add 100 μL of HBSS pH 7.4 pre-incubation buffer containing vehicle to the apical compartments.
4. Incubate the plates with orbital shaking at approximately 60 RPM for the pre-incubation time specified in Table 1 of this protocol.
5. Aspirate the pre-incubation buffer from the apical compartment of the plates. Add 100 μL of the experimental buffer that is prepared as follows and maintained at ambient temperatures.
   a. For the probe substrate transport assay, the HBSS with Bis-Tris, pH 5.5 in each well contains the probe substrate at 500 μM (positive control for transport) and vehicle control.
   b. For the test article assays, the HBSS with Bis-Tris, pH 5.5 in each well contains the test article at 10 μM, 30 μM, 100 μM, 300 μM, 1000 μM, 3000 μM, and 10000 μM.
6. Incubate at ambient temperature with orbital shaking at approximately 60 RPM for the incubation time of 1 minute.
7. Wash both the apical and the basal side of the permeable support four times with ice cold PBS.
8. Add 60 μL cell extraction solution to the 96-well plate wells.
9. Agitate to mix the extract for approximately 15 minutes on an orbital shaker at approximately 120 rpm.
10. Collect a 30 μL sample of the extract.
11. Add 30 μL of internal standard (IS) before freezing the samples for further analysis by LC-MS/MS.

E. Analytical, Data Analysis

1. The amount of radiolabeled probe substrate will be quantified with radiometric detection on a 1450 Microbeta (Perkin-Elmer).
2. The amount of non-radiolabeled probe substrate or test article will be quantified by LC-MS/MS.
3. For transport study samples run in triplicate, the mean and standard deviation of the replicates will be reported.
4. For uptake assays, the net transporter-mediated uptake rate (V) of the substrate by each SLC transporter will be calculated as follows:

$$\text{Transporter-mediated uptake rate (pmol/min/cm}^2) = \frac{\text{(Cellular accumulation in cells expressing the transporter)} - \text{(Mean cellular accumulation in control cells)}}{\text{Surface area} * \text{Incumbation time}}$$

5. For transport kinetics assessment, $K_m$ and $V_{max}$ will be calculated by non-linear regression using the Michaelis-Menten equation.
6. All reported data are based on nominal concentration used unless otherwise stated.

Figure 5:
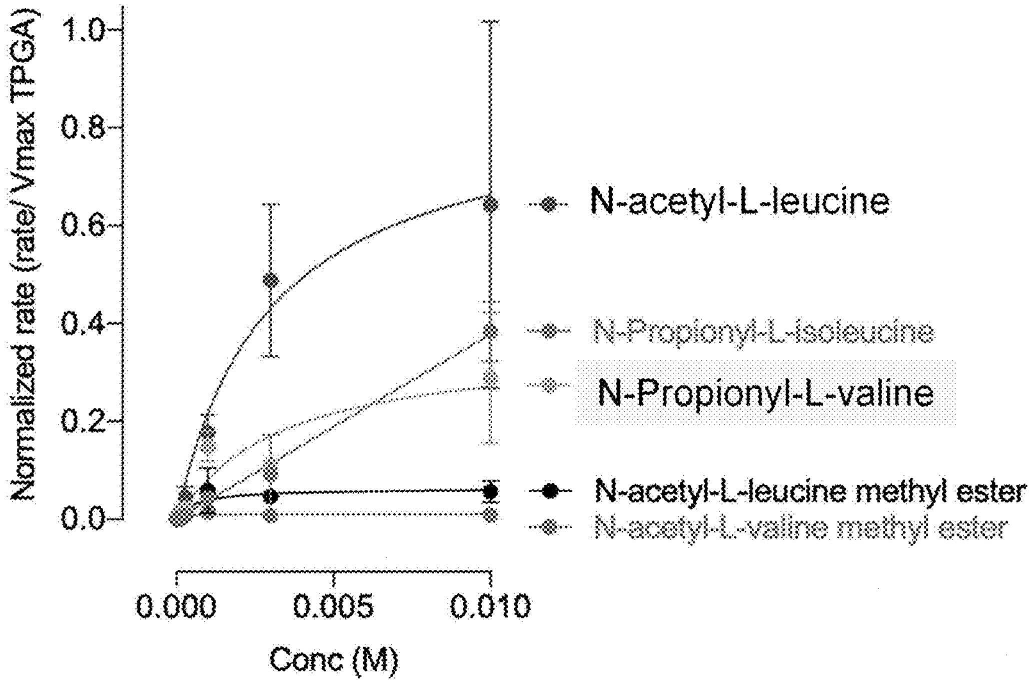
FIG. 5 is a line graph showing uptake mediated by the monocarboxylate transporter 1 (MCT1) of N-acetyl-L-leucine, N-propionyl-L-isoleucine, N-propionyl-L-valine, N-acetyl-L-leucine methyl ester, and N-acetyl-L-valine methyl ester. Data were fitted to the Michaelis-Menten equation using non-linear regression in GraphPad Prism. All data are normalized to the $V_{max}$ for the known substrate (positive control) thiophene-2-glyoxylic acid. Data show mean±standard error of the mean (n=3).

The structure-activity relationship for branched chain amino acid or acid ester uptake mediated by the monocarboxylate transporter 1 (MCT1) is shown in FIG. 5. All data are normalized to the $V_{max}$ for the known substrate (positive control) thiophene-2-glyoxylic acid. Data show mean± standard error of the mean (n=3).

N-acetyl-L-leucine, N-propionyl-L-isoleucine, and N-propionyl-L-valine are transported by MCT1. Esterification of N-acetyl-L-leucine and N-acetyl-L-valine to the methyl esters greatly reduced transport, suggesting that a negative charge on the carboxylate is required for activity.

Having now fully described the methods, compounds, and compositions herein, it will be understood by those of skill in the art that the same can be performed within a wide and equivalent range of conditions, formulations, and other parameters without affecting the scope of the methods, compounds, and compositions provided herein or any embodiment thereof. All patents, patent applications, and publications cited herein are fully incorporated by reference herein in their entirety.

REFERENCES

1. Neuzil, E., Ravaine, S. & Cousse, H. La N-acetyl-DL-leucine, medicament symptomatique de vertigineux. Bull Soc Pharm Bordx. *Bull. Soc. Pharm. Bordeaux* 141, 15-38 (2002).
2. Strupp, M. et al. Effects of acetyl-DL-leucine in patients with cerebellar ataxia: a case series. *J. Neurol.* 260, 2556-2561 (2013).
3. Feil, K. et al. Effects of acetyl-DL-leucine on cerebellar ataxia (ALCAT trial): study protocol for a multicenter, multinational, randomized, double-blind, placebo-controlled, crossover phase III trial. *BMC Neurol* 17, 7 (2017).
4. Schniepp, R. et al. Acetyl-DL-leucine improves gait variability in patients with cerebellar ataxia-a case series. *Cerebellum Ataxias* 3, 8 (2016).
5. Platt, F. & Strupp, M. An anecdotal report by an Oxford basic neuroscientist: effects of acetyl-DL-leucine on cognitive function and mobility in the elderly. *J. Neurol.* 263, 1239-1240 (2016).
6. Kalla, R. & Strupp, M. Aminopyridines and acetyl-DL-leucine: new therapies in cerebellar disorders. *Curr Neuropharmacol* 17, 7-13 (2019).
7. Bremova, T. et al. Acetyl-dl-leucine in Niemann-Pick type C: A case series. *Neurology* 85, 1368-1375 (2015).
8. Cortina-Borja, M. et al. Annual severity increment score as a tool for stratifying patients with Niemann-Pick disease type C and for recruitment to clinical trials. *Orphanet J Rare Dis* 13, 143 (2018).
9. Strupp, M., Bayer, O., Feil, K. & Straube, A. Prophylactic treatment of migraine with and without aura with acetyl-DL-leucine: a case series. *J. Neurol.* 266, 525-529 (2019).
10. Kaya, E. et al. Acetyl-leucine slows disease progression in lysosomal storage disorders. *Brain Commun* fcaa148, https://doi.org/10.1093/braincomms/fcaa148, (2020).
11. Kanai, Y. et al. Expression cloning and characterization of a transporter for large neutral amino acids activated by the heavy chain of 4F2 antigen (CD98). *J Biol Chem* 273, 23629-23632 (1998).
12. Halestrap, A. P. & Wilson, M. C. The monocarboxylate transporter family—role and regulation. *IUBMB Life* 64, 109-119 (2012).
13. Puri, S. & Juvale, K. Monocarboxylate transporter 1 and 4 inhibitors as potential therapeutics for treating solid tumours: A review with structure-activity relationship insights. *Eur J Med Chem* 199, 112393 (2020).

14. Churchill, G. C., Strupp, M., Galione, A. & Platt, F. M. Unexpected differences in the pharmacokinetics of N-acetyl-DL-leucine enantiomers after oral dosing and their clinical relevance. *PLoS One* 15, e0229585 (2020).
15. Nicklin, P. et al. Bidirectional transport of amino acids regulates mTOR and autophagy. *Cell* 136, 521-534 (2009).
16. Bröer, S. & Fairweather, S. J. Amino Acid Transport Across the Mammalian Intestine. *Compr Physiol* 9, 343-373 (2018).
17. Wang, G. et al. Intestinal OCTN2- and MCT1-targeted drug delivery to improve oral bioavailability. *Asian J Pharm Sci* 15, 158-173 (2020).
18. Kaya, E. et al. Beneficial effects of acetyl-DL-leucine (ADLL) in a mouse model of Sandhoff disease. *J Clin Med* 9, 1050 (2020).
19. Schoser, B., Schnautzer, F., Bremova, T. & Strupp, M. Treatment of restless legs syndrome with acetyl-DL-leucine—accidental findings and a small case series. *European Journal of Neurology* 26, 694: EP02251 (2019).
20. Fields, T. et al. A master protocol to investigate a novel therapy acetyl-L-leucine for three ultra-rare neurodegenerative diseases: Niemann-Pick type C, the GM2 Gangliosidoses, and Ataxia Telangiectasia. *Trials* In Press, (2020).
21. International Transporter Consortium et al. Membrane transporters in drug development. *Nat Rev Drug Discov* 9, 215-236 (2010).
22. Keogh, J. P. Membrane transporters in drug development. *Adv Pharmacol* 63, 1-42 (2012).
23. Missner, A. & Pohl, P. 110 years of the Meyer-Overton rule: predicting membrane permeability of gases and other small compounds. *Chemphyschem* 10, 1405-1414 (2009).
24. Camenisch, G., Folkers, G. & van de Waterbeemd, H. Review of theoretical passive drug absorption models: Historical background, recent developments and limitations. *Pharmaceutica Acta Helvetiae* 71, 309-327 (1996).
25. Gleeson, M. P., Hersey, A., Montanari, D. & Overington, J. Probing the links between in vitro potency, ADMET and physicochemical parameters. *Nat Rev Drug Discov* 10, 197-208 (2011).
26. Leeson, P. D. & Springthorpe, B. The influence of drug-like concepts on decision-making in medicinal chemistry. *Nat Rev Drug Discov* 6, 881-890 (2007).
27. Lipinski, C. A. Drug-like properties and the causes of poor solubility and poor permeability. *J Pharmacol Toxicol Methods* 44, 235-249 (2000).
28. Waring, M. J. Defining optimum lipophilicity and molecular weight ranges for drug candidates-Molecular weight dependent lower log D limits based on permeability. *Bioorg Med Chem Lett* 19, 2844-2851 (2009).
29. van de Waterbeemd, H., Camenisch, G., Folkers, G., Chretien, J. R. & Raevsky, O. A. Estimation of blood-brain barrier crossing of drugs using molecular size and shape, and H-bonding descriptors. *J Drug Target* 6, 151-165 (1998).
30. Walter, A. & Gutknecht, J. Monocarboxylic acid permeation through lipid bilayer membranes. *J Membr Biol* 77, 255-264 (1984).
31. Neuhoff, S., Ungell, A.-L., Zamora, I. & Artursson, P. pH-Dependent passive and active transport of acidic drugs across Caco-2 cell monolayers. *Eur J Pharm Sci* 25, 211-220 (2005).
32. Benard, P., Cousse, H., Bengone, T. & Germain, C. Autoradiography in brain of *Macaca fascicularis* monkeys after injection of acetyl-DL-leucine [2-14C] (Tanganil). *Eur J Drug Metab Pharmacokinet* 26, 71-76 (2001).
33. Sugano, K. et al. Coexistence of passive and carrier-mediated processes in drug transport. *Nat Rev Drug Discov* 9, 597-614 (2010).
34. Krehbiel, C. R. & Matthews, J. C. Absorption of Amino Acids and Peptides. in *Amino Acids in Animal Nutrition* (ed. D'Mello, J. P. F.) 41-70 (CABI Publishing, 2003).
35. Scalise, M., Galluccio, M., Console, L., Pochini, L. & Indiveri, C. The Human SLC7A5 (LAT1): The Intriguing Histidine/Large Neutral Amino Acid Transporter and Its Relevance to Human Health. *Front Chem* 6, 243 (2018).
36. Soares-da-Silva, P. & Serrão, M. P. High- and low-affinity transport of L-leucine and L-DOPA by the hetero amino acid exchangers LAT1 and LAT2 in LLC-PK1 renal cells. *Am J Physiol Renal Physiol* 287, F252-261 (2004).
37. del Amo, E. M., Urtti, A. & Yliperttula, M. Pharmacokinetic role of L-type amino acid transporters LAT1 and LAT2. *Eur J Pharm Sci* 35, 161-174 (2008).
38. Fagerberg, L. et al. Analysis of the Human Tissue-specific Expression by Genome-wide Integration of Transcriptomics and Antibody-based Proteomics. *Mol Cell Proteomics* 13, 397-406 (2014).
39. Pochini, L., Scalise, M., Galluccio, M. & Indiveri, C. Membrane transporters for the special amino acid glutamine: structure/function relationships and relevance to human health. *Front Chem* 2, 61 (2014).
40. Nagamori, S. et al. Structure-activity relations of leucine derivatives reveal critical moieties for cellular uptake and activation of mTORC1-mediated signaling. *Amino Acids* 48, 1045-1058 (2016).
41. Sawada, K., Terada, T., Saito, H., Hashimoto, Y. & Inui, K. I. Recognition of L-amino acid ester compounds by rat peptide transporters PEPT1 and PEPT2. *J Pharmacol Exp Ther* 291, 705-709 (1999).
42. Thompson, B. R., Shi, J., Zhu, H.-J. & Smith, D. E. Pharmacokinetics of gemcitabine and its amino acid ester prodrug following intravenous and oral administrations in mice. *Biochem Pharmacol* 180, 114127 (2020).
43. Brandsch, M., Knütter, I. & Leibach, F. H. The intestinal H+/peptide symporter PEPT1: structure-affinity relationships. *Eur J Pharm Sci* 21, 53-60 (2004).
44. Rubio-Aliaga, I. & Daniel, H. Peptide transporters and their roles in physiological processes and drug disposition. *Xenobiotica* 38, 1022-1042 (2008).
45. Koepsell, H. & Endou, H. The SLC22 drug transporter family. *Pflugers Arch* 447, 666-676 (2004).
46. Lin, L., Yee, S. W., Kim, R. B. & Giacomini, K. M. SLC transporters as therapeutic targets: emerging opportunities. *Nat Rev Drug Discov* 14, 543-560 (2015).
47. Nigam, S. K. et al. The organic anion transporter (OAT) family: a systems biology perspective. *Physiol Rev* 95, 83-123 (2015).

48. Enerson, B. E. & Drewes, L. R. Molecular features, regulation, and function of monocarboxylate transporters: implications for drug delivery. *J Pharm Sci* 92, 1531-1544 (2003).
49. Cheng, Y. & Prusoff, W. H. Relationship between the inhibition constant (K1) and the concentration of inhibitor which causes 50 percent inhibition (I50) of an enzymatic reaction. *Biochem Pharmacol* 22, 3099-3108 (1973).
50. Bloch, K. & Rittenberg, D. The metabolism of acetylamino acids. *J. Biol. Chem.* 169, 467-476 (1947).
51. Sheffner, A. L. et al. Metabolic studies with acetylcysteine. *Biochem Pharmacol* 15, 1523-1535 (1966).
52. Neuhäuser, M., Wandira, J. A., Göttmann, U., Bässler, K. H. & Langer, K. Utilization of N-acetyl-L-tyrosine and glycyl-L-tyrosine during long-term parenteral nutrition in the growing rat. *Am J Clin Nutr* 42, 585-596 (1985).
53. Im Haesook, A., Meyer Paul, D. & Stegink, L. D. N-Acetyl-L-Tyrosine as a Tyrosine Source during Total Parenteral Nutrition in Adult Rats. *Pediatric Research* 19, 514-518 (1985).
54. Birnbaum, S. M., Levintow, L., Kingsley, R. B. & Greenstein, J. P. Specificity of amino acid acylases. *J. Biol. Chem.* 194, 455-470 (1952).
55. Gregori-Puigjané, E. et al. Identifying mechanism-of-action targets for drugs and probes. *Proc Natl Acad Sci USA* 109, 11178-11183 (2012).
56. Kalogeropoulou, D., Lafave, L., Schweim, K., Gannon, M. C. & Nuttall, F. Q. Leucine, when ingested with glucose, synergistically stimulates insulin secretion and lowers blood glucose. *Metabolism* 57, 1747-1752 (2008).
57. Eriksson, T., Björkman, S. & Höglund, P. Clinical pharmacology of thalidomide. *Eur. J. Clin. Pharmacol.* 57, 365-376 (2001).
58. Smith, Q. R., Momma, S., Aoyagi, M. & Rapoport, S. I. Kinetics of neutral amino acid transport across the blood-brain barrier. *J Neurochem* 49, 1651-1658 (1987).
59. Ananieva, E. A., Powell, J. D. & Hutson, S. M. Leucine Metabolism in T Cell Activation: mTOR Signaling and Beyond. *Adv Nutr* 7, 798S-805S (2016).
60. Tighilet, B., Leonard, J., Bernard-Demanze, L. & Lacour, M. Comparative analysis of pharmacological treatments with N-acetyl-DL-leucine (Tanganil) and its two isomers (N-acetyl-L-leucine and N-acetyl-D-leucine) on vestibular compensation: Behavioral investigation in the cat. *Eur. J. Pharmacol.* 769, 342-349 (2015).
61. Vruchte, D. te, Galione, A., Strupp, M. & Mann, M. Effects of N-Acetyl-Leucine and its enantiomers in Niemann-Pick disease type C cells. *bioRxiv* 826222 (2019) doi:10.1101/826222.
62. Kennedy, B. E. et al. Adaptations of energy metabolism associated with increased levels of mitochondrial cholesterol in Niemann-Pick type C1-deficient cells. *J Biol Chem* 289, 16278-16289 (2014)
63. Jha, M. K. et al. Metabolic Connection of Inflammatory Pain: Pivotal Role of a Pyruvate Dehydrogenase Kinase-Pyruvate Dehydrogenase-Lactic Acid Axis. *J Neurosci* 35, 14353-14369 (2015).
64. Oláh, J. et al. Increased glucose metabolism and ATP level in brain tissue of Huntington's disease transgenic mice. *FEBS J* 275, 4740-4755 (2008).
65. Sun, S., Li, H., Chen, J. & Qian, Q. Lactic Acid: No Longer an Inert and End-Product of Glycolysis. *Physiology* (*Bethesda*) 32, 453-463 (2017).
66. Patet, C., Suys, T., Carteron, L. & Oddo, M. Cerebral Lactate Metabolism After Traumatic Brain Injury. *Curr Neurol Neurosci Rep* 16, 31 (2016).
67. Hashimoto, T., Hussien, R., Oommen, S., Gohil, K. & Brooks, G. A. Lactate sensitive transcription factor network in L6 cells: activation of MCT1 and mitochondrial biogenesis. *FASEB J* 21, 2602-2612 (2007).
68. Newington, J. T., Harris, R. A. & Cumming, R. C. Reevaluating Metabolism in Alzheimer's Disease from the Perspective of the Astrocyte-Neuron Lactate Shuttle Model. *J. Neurodegener. Dis.* 2013, 234572 (2013).
69. Sala, N. et al. Cerebral extracellular lactate increase is predominantly nonischemic in patients with severe traumatic brain injury. *J. Cereb. Blood Flow Metab.* 33, 1815-1822 (2013).
70. Fagan, T. The Lactic Acid Shuttle—It May Change How We Image the Brain (2004). At https://www.alzforum.org/news/research-news/lactic-acid-shuttle-it-may-change-how-we-image-brain (accessed 11/12/2020)
71. Izyumov, D. S. et al. "Wages of Fear": transient threefold decrease in intracellular ATP level imposes apoptosis. *Biochim. Biophys. Acta* 1658, 141-147 (2004).
72. Jha, M. K., Jeon, S., and Suk, K. Pyruvate Dehydrogenase Kinases in the Nervous System: Their Principal Functions in Neuronal-glial Metabolic Interaction and Neuro-metabolic Disorders. *Curr. Neuropharmacol.* 10, 393-403 (2012).

What is claimed is:

1. A method of treating a disease, disorder, or condition, or a symptom thereof, in a subject in need thereof, the method comprising administering to the subject a therapeutically effective amount of Formula I:

I

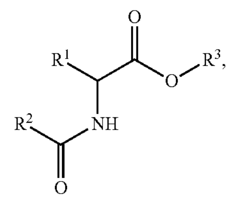

or a pharmaceutically acceptable salt or solvate thereof, wherein:

$R^1$ is selected from the group consisting of:

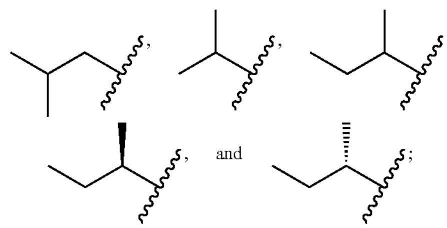

$R^2$ is selected from the group consisting of $C_2$-$C_6$ alkyl and $C_3$-$C_6$ cycloalkyl; and $R^3$ is selected from the group consisting of hydrogen, $C_1$-$C_6$ alkyl, and $C_3$-$C_6$ cycloalkyl, or a pharmaceutically acceptable salt or solvate thereof, wherein the disease, disorder, or condition is a lysosomal storage disorder, a neurodegenerative disease, a traumatic brain injury, or a migraine.

2. The method of claim 1, wherein the disease, disorder, or condition is a lysosomal storage disorder.

3. The method of claim 2, wherein the lysosomal storage disorder is a primary lysosomal hydrolase defect, a post-translational processing defect of lysosomal enzymes, a trafficking defect for lysosomal enzymes, a defect in lysosomal enzyme protection, a defect in soluble non-enzymatic lysosomal proteins, a transmembrane (non-enzyme) protein defect or an unclassified defect.

4. The method of claim 2, wherein the lysosomal storage disorder is Niemann-Pick disease, Tay-Sachs disease, Sandhoff disease, GM1 gangliosidosis, or Fabry disease.

5. The method of claim 1, wherein the disease, disorder, or condition is a neurodegenerative disease.

6. The method of claim 1, wherein the neurodegenerative disease is cerebellar ataxia, neuronopathic Gaucher disease, Louis-Barr syndrome, Alzheimer's disease, Parkinson's disease, multiple systems atrophy, fronto-temporal dementia, or lower body Parkinson's syndrome.

7. The method of claim 1, wherein the disease, disorder, or condition is a traumatic brain injury.

8. The method of claim 1, wherein the disease, disorder, or condition is a migraine.

* * * * *